(12) United States Patent
Graetzel et al.

(10) Patent No.: US 11,324,558 B2
(45) Date of Patent: May 10, 2022

(54) ELECTROMAGNETIC DISTORTION DETECTION AND COMPENSATION

(71) Applicant: Auris Health, Inc., Redwood City, CA (US)

(72) Inventors: Chauncey F. Graetzel, Palo Alto, CA (US); Subashini Srinivasan, San Carlos, CA (US); Yuriy Malinin, Palo Alto, CA (US); Shyamprasad Konduri, Belmont, CA (US)

(73) Assignee: Auris Health, Inc., Redwood City, CA (US)

(*) Notice: Subject to any disclaimer, the term of this patent is extended or adjusted under 35 U.S.C. 154(b) by 0 days.

(21) Appl. No.: 17/009,593

(22) Filed: Sep. 1, 2020

(65) Prior Publication Data
US 2021/0059766 A1 Mar. 4, 2021

Related U.S. Application Data

(60) Provisional application No. 62/895,272, filed on Sep. 3, 2019.

(51) Int. Cl.
*A61B 34/20* (2016.01)
*G16H 40/63* (2018.01)
(Continued)

(52) U.S. Cl.
CPC ............ *A61B 34/20* (2016.02); *G06N 20/00* (2019.01); *G16H 40/40* (2018.01); *G16H 40/63* (2018.01);
(Continued)

(58) Field of Classification Search
CPC ............ A61B 34/20; A61B 2034/105; A61B 2034/2051; A61B 2034/301;
(Continued)

(56) References Cited

U.S. PATENT DOCUMENTS 805,269 A 11/1905 Dorr
4,921,393 A 5/1990 Andeen et al.
(Continued)

FOREIGN PATENT DOCUMENTS

CN 106821498 A 6/2017
CN 109414287 B 4/2021
(Continued)

OTHER PUBLICATIONS

Search Report for appl No. WO20211044297, dated Mar. 11, 2021, 4 pages.
(Continued)

*Primary Examiner* — Brenda C Bernardi
(74) *Attorney, Agent, or Firm* — Chang & Hale LLP

(57) ABSTRACT

Systems and methods for electromagnetic (EM) distortion detection and compensation are disclosed. In one aspect, the system includes an instrument, the system configured to: determine a reference position of the distal end of the instrument at a first time based on EM location data, determine that the distal end of the instrument at a second time is static, and determine that the EM location data at the second time is indicative of a position of the distal end of the instrument having changed from the reference position by greater than a threshold distance. The system is further configured to: determine a current offset based on the distance between the position at the second time and the reference position at the first time, and determine a compensated position of the distal end of the instrument based on the EM location data and the current offset.

30 Claims, 38 Drawing Sheets

(51) Int. Cl.
  *G16H 70/20* (2018.01)
  *G16H 40/40* (2018.01)
  *G16H 20/00* (2018.01)
  *A61B 34/10* (2016.01)
  *A61B 34/30* (2016.01)
  *G06N 20/00* (2019.01)

(52) U.S. Cl.
  CPC ........ *G16H 70/20* (2018.01); *A61B 2034/105* (2016.02); *A61B 2034/2051* (2016.02); *A61B 2034/301* (2016.02); *A61B 2034/302* (2016.02); *A61B 2034/303* (2016.02)

(58) Field of Classification Search
  CPC ........ A61B 2034/302; A61B 2034/303; G16H 40/40; G16H 40/63; G16H 70/20; G06N 20/00
  See application file for complete search history.

(56) References Cited

U.S. PATENT DOCUMENTS

| | | | |
|---|---|---|---|
| 5,273,025 A | 12/1993 | Sakiyama et al. | |
| 5,375,588 A | 12/1994 | Yoon | |
| 5,402,801 A | 4/1995 | Taylor | |
| 5,526,812 A | 6/1996 | Dumoulin et al. | |
| 5,540,648 A | 7/1996 | Yoon | |
| 5,746,720 A | 5/1998 | Stouder, Jr. | |
| 5,831,614 A | 11/1998 | Tognazzini et al. | |
| 5,865,809 A | 2/1999 | Moenning et al. | |
| 5,935,075 A | 8/1999 | Casscells et al. | |
| 6,038,467 A | 3/2000 | Bliek et al. | |
| 6,047,080 A | 4/2000 | Chen et al. | |
| 6,059,718 A | 5/2000 | Taniguchi et al. | |
| 6,063,095 A | 5/2000 | Wang et al. | |
| 6,167,292 A | 12/2000 | Badano et al. | |
| 6,203,493 B1 | 3/2001 | Ben-Haim | |
| 6,246,784 B1 | 6/2001 | Summers et al. | |
| 6,246,898 B1 | 6/2001 | Vesely et al. | |
| 6,279,579 B1 | 8/2001 | Riaziat et al. | |
| 6,425,865 B1 | 7/2002 | Salcudean et al. | |
| 6,466,198 B1 | 10/2002 | Feinstein | |
| 6,522,906 B1 | 2/2003 | Salisbury et al. | |
| 6,665,554 B1 | 12/2003 | Charles et al. | |
| 6,690,964 B2 | 2/2004 | Bieger et al. | |
| 6,850,817 B1 | 2/2005 | Green | |
| 7,180,976 B2 | 2/2007 | Wink et al. | |
| 7,386,339 B2 | 6/2008 | Strommer et al. | |
| 7,699,855 B2 | 4/2010 | Anderson et al. | |
| 7,756,563 B2 | 7/2010 | Higgins et al. | |
| 7,805,269 B2 * | 9/2010 | Glossop ................ | A61B 34/20 702/94 |
| 8,190,238 B2 | 5/2012 | Moll et al. | |
| 8,394,054 B2 | 3/2013 | Wallace et al. | |
| 8,469,947 B2 | 6/2013 | Devengenzo et al. | |
| 8,491,597 B2 | 7/2013 | Russell et al. | |
| 8,506,555 B2 | 8/2013 | Morales | |
| 8,755,124 B2 | 6/2014 | Aschwanden et al. | |
| 8,821,376 B2 | 9/2014 | Tolkowsky | |
| 9,014,851 B2 | 4/2015 | Wong et al. | |
| 9,138,129 B2 | 9/2015 | Diolaiti | |
| 9,186,046 B2 | 11/2015 | Ramamurthy et al. | |
| 9,226,796 B2 | 1/2016 | Bowling et al. | |
| 9,289,578 B2 | 3/2016 | Walker et al. | |
| 9,333,047 B2 * | 5/2016 | Mucha ................... | A61B 34/30 |
| 9,459,087 B2 | 10/2016 | Dunbar et al. | |
| 9,480,534 B2 | 11/2016 | Bowling et al. | |
| 9,504,604 B2 | 11/2016 | Alvarez | |
| 9,561,083 B2 | 2/2017 | Yu et al. | |
| 9,622,827 B2 | 4/2017 | Yu et al. | |
| 9,629,682 B2 | 4/2017 | Wallace et al. | |
| 9,636,184 B2 | 5/2017 | Lee et al. | |
| 9,710,921 B2 | 7/2017 | Wong et al. | |
| 9,713,509 B2 | 7/2017 | Schuh et al. | |
| 9,727,963 B2 | 8/2017 | Mintz et al. | |
| 9,737,371 B2 | 8/2017 | Romo et al. | |
| 9,737,373 B2 | 8/2017 | Schuh | |
| 9,744,335 B2 | 8/2017 | Jiang | |
| 9,763,741 B2 | 9/2017 | Alvarez et al. | |
| 9,788,910 B2 | 10/2017 | Schuh | |
| 9,795,445 B2 | 10/2017 | Bowling | |
| 9,818,681 B2 | 11/2017 | Machida | |
| 9,820,818 B2 | 11/2017 | Malackowski et al. | |
| 9,844,412 B2 | 12/2017 | Bogusky et al. | |
| 9,867,635 B2 | 1/2018 | Alvarez et al. | |
| 9,918,681 B2 | 3/2018 | Wallace et al. | |
| 9,931,025 B1 | 4/2018 | Graetzel et al. | |
| 9,949,749 B2 | 4/2018 | Noonan et al. | |
| 9,955,986 B2 | 5/2018 | Shah | |
| 9,962,228 B2 | 5/2018 | Schuh et al. | |
| 9,980,785 B2 | 5/2018 | Schuh | |
| 9,993,313 B2 | 6/2018 | Schuh et al. | |
| 10,004,562 B2 | 6/2018 | Kostrzewski et al. | |
| 10,004,569 B2 | 6/2018 | Singh et al. | |
| 10,016,900 B1 | 7/2018 | Meyer et al. | |
| 10,022,192 B1 | 7/2018 | Ummalaneni | |
| 10,145,747 B1 | 12/2018 | Lin et al. | |
| 10,154,829 B2 | 12/2018 | Henderson et al. | |
| 10,159,532 B1 | 12/2018 | Ummalaneni | |
| 10,180,481 B2 | 1/2019 | Srinivasan et al. | |
| 10,299,870 B2 | 5/2019 | Connolly et al. | |
| 10,426,559 B2 | 10/2019 | Graetzel et al. | |
| 10,434,660 B2 | 10/2019 | Meyer et al. | |
| 10,464,209 B2 | 11/2019 | Ho et al. | |
| 10,470,830 B2 | 11/2019 | Hill et al. | |
| 10,482,599 B2 | 11/2019 | Mintz et al. | |
| 10,492,869 B2 | 12/2019 | Malinin et al. | |
| 10,517,692 B2 | 12/2019 | Eyre et al. | |
| 10,524,866 B2 | 1/2020 | Srinivasan et al. | |
| 10,539,478 B2 | 1/2020 | Lin et al. | |
| 10,684,344 B2 | 6/2020 | Daniel et al. | |
| 10,750,975 B2 | 8/2020 | Hill et al. | |
| 10,765,303 B2 | 9/2020 | Graetzel et al. | |
| 10,765,487 B2 | 9/2020 | Ho et al. | |
| 10,813,539 B2 | 10/2020 | Graetzel et al. | |
| 10,898,276 B2 | 1/2021 | Graetzel et al. | |
| 10,898,277 B2 | 1/2021 | Srinivasan et al. | |
| 10,898,286 B2 | 1/2021 | Srinivasan et al. | |
| 2001/0039421 A1 | 11/2001 | Heilbrun et al. | |
| 2002/0077533 A1 | 6/2002 | Bieger et al. | |
| 2002/0120188 A1 | 8/2002 | Brock et al. | |
| 2002/0193685 A1 | 12/2002 | Mate et al. | |
| 2003/0050558 A1 | 3/2003 | Bencini et al. | |
| 2003/0125622 A1 | 7/2003 | Schweikard et al. | |
| 2003/0195664 A1 | 10/2003 | Nowlin et al. | |
| 2004/0047044 A1 | 3/2004 | Dalton | |
| 2004/0078036 A1 | 4/2004 | Keidar | |
| 2004/0263535 A1 | 12/2004 | Birkenbach et al. | |
| 2005/0027397 A1 | 2/2005 | Niemeyer | |
| 2005/0060006 A1 | 3/2005 | Pflueger et al. | |
| 2005/0085714 A1 | 4/2005 | Foley et al. | |
| 2005/0143649 A1 | 6/2005 | Minai et al. | |
| 2005/0182295 A1 | 8/2005 | Soper et al. | |
| 2005/0193451 A1 | 9/2005 | Quistgaard et al. | |
| 2006/0004286 A1 | 1/2006 | Chang et al. | |
| 2006/0015096 A1 | 1/2006 | Hauck et al. | |
| 2006/0058643 A1 | 3/2006 | Florent et al. | |
| 2006/0079756 A1 | 4/2006 | Lloyd et al. | |
| 2006/0098851 A1 | 5/2006 | Shoham et al. | |
| 2006/0173290 A1 | 8/2006 | Lavallee et al. | |
| 2006/0184016 A1 | 8/2006 | Glossop | |
| 2006/0258938 A1 | 11/2006 | Hoffman et al. | |
| 2006/0270909 A1 | 11/2006 | Davis et al. | |
| 2007/0021738 A1 | 1/2007 | Hasser et al. | |
| 2007/0055128 A1 | 3/2007 | Glossop | |
| 2007/0123748 A1 | 5/2007 | Meglan | |
| 2007/0135886 A1 | 6/2007 | Maschke | |
| 2007/0144298 A1 | 6/2007 | Miller | |
| 2007/0208252 A1 | 9/2007 | Makower | |
| 2007/0244599 A1 | 10/2007 | Tsai et al. | |
| 2007/0253599 A1 | 11/2007 | White et al. | |
| 2008/0033282 A1 * | 2/2008 | Bar-Tal ................. | A61B 5/062 600/424 |
| 2008/0071140 A1 | 3/2008 | Gattani et al. | |

(56) References Cited

U.S. PATENT DOCUMENTS

| | | |
|---|---|---|
| 2008/0077158 A1 | 3/2008 | Haider et al. |
| 2008/0079421 A1 | 4/2008 | Jensen |
| 2008/0118118 A1 | 5/2008 | Berger |
| 2008/0119725 A1 | 5/2008 | Lloyd |
| 2008/0161681 A1 | 7/2008 | Hauck |
| 2008/0183064 A1 | 7/2008 | Chandonnet et al. |
| 2008/0183068 A1 | 7/2008 | Carls et al. |
| 2008/0183188 A1 | 7/2008 | Carls et al. |
| 2008/0201016 A1 | 8/2008 | Finlay |
| 2008/0212082 A1 | 9/2008 | Froggatt et al. |
| 2008/0218770 A1 | 9/2008 | Moll et al. |
| 2008/0243142 A1 | 10/2008 | Gildenberg |
| 2008/0287963 A1 | 11/2008 | Rogers et al. |
| 2008/0306490 A1 | 12/2008 | Lakin et al. |
| 2008/0312501 A1 | 12/2008 | Hasegawa et al. |
| 2009/0076476 A1 | 3/2009 | Barbagli et al. |
| 2009/0079426 A1 | 3/2009 | Anderson |
| 2009/0088634 A1 | 4/2009 | Zhao et al. |
| 2009/0099445 A1 | 4/2009 | Burger |
| 2009/0248036 A1 | 10/2009 | Hoffman et al. |
| 2009/0248037 A1 | 10/2009 | Prisco |
| 2009/0259230 A1 | 10/2009 | Khadem et al. |
| 2009/0259412 A1 | 10/2009 | Brogardh |
| 2009/0262109 A1 | 10/2009 | Markowitz et al. |
| 2009/0295797 A1 | 12/2009 | Sakaguchi |
| 2010/0039506 A1 | 2/2010 | Sarvestani et al. |
| 2010/0054536 A1 | 3/2010 | Huang et al. |
| 2010/0113852 A1 | 5/2010 | Sydora |
| 2010/0161022 A1 | 6/2010 | Tolkowsky |
| 2010/0161129 A1 | 6/2010 | Costa et al. |
| 2010/0225209 A1 | 9/2010 | Goldberg et al. |
| 2010/0234999 A1 | 9/2010 | Nakajima |
| 2010/0240989 A1 | 9/2010 | Stoianovici et al. |
| 2010/0292565 A1 | 11/2010 | Meyer et al. |
| 2010/0298641 A1 | 11/2010 | Tanaka |
| 2010/0328455 A1 | 12/2010 | Nam et al. |
| 2011/0040411 A1 | 2/2011 | Murayama et al. |
| 2011/0054303 A1 | 3/2011 | Barrick et al. |
| 2011/0060215 A1 | 3/2011 | Tupin, Jr. et al. |
| 2011/0144479 A1 | 6/2011 | Hastings et al. |
| 2011/0208355 A1 | 8/2011 | Tsusaka |
| 2011/0234780 A1 | 9/2011 | Ito et al. |
| 2011/0238082 A1 | 9/2011 | Wenderow et al. |
| 2011/0248987 A1 | 10/2011 | Mitchell |
| 2011/0268248 A1 | 11/2011 | Simon et al. |
| 2012/0046542 A1 | 2/2012 | Csavoy et al. |
| 2012/0056986 A1 | 3/2012 | Popovic |
| 2012/0065481 A1 | 3/2012 | Hunter et al. |
| 2012/0069167 A1 | 3/2012 | Liu et al. |
| 2012/0082351 A1 | 4/2012 | Higgins et al. |
| 2012/0165656 A1 | 6/2012 | Montag et al. |
| 2012/0172712 A1 | 7/2012 | Bar-tal |
| 2012/0191107 A1 | 7/2012 | Tanner et al. |
| 2012/0209069 A1 | 8/2012 | Popovic et al. |
| 2012/0219185 A1 | 8/2012 | Hu et al. |
| 2013/0041509 A1 | 2/2013 | Saito et al. |
| 2013/0060146 A1 | 3/2013 | Fang et al. |
| 2013/0076355 A1 | 3/2013 | Srinivasan et al. |
| 2013/0169423 A1 | 7/2013 | Iorgulescu et al. |
| 2013/0173058 A1 | 7/2013 | Seo et al. |
| 2013/0243153 A1 | 9/2013 | Sra et al. |
| 2013/0246334 A1 | 9/2013 | Ahuja et al. |
| 2013/0259315 A1 | 10/2013 | Angot et al. |
| 2013/0345718 A1 | 12/2013 | Crawford et al. |
| 2014/0039517 A1 | 2/2014 | Bowling et al. |
| 2014/0052154 A1 | 2/2014 | Griffiths et al. |
| 2014/0088763 A1 | 3/2014 | Hazan |
| 2014/0114180 A1 | 4/2014 | Jain |
| 2014/0142591 A1 | 5/2014 | Alvarez et al. |
| 2014/0148808 A1 | 5/2014 | Inkpen et al. |
| 2014/0180063 A1 | 6/2014 | Zhao et al. |
| 2014/0243849 A1 | 8/2014 | Saglam et al. |
| 2014/0257746 A1 | 9/2014 | Dunbar et al. |
| 2014/0276033 A1 | 9/2014 | Brannan et al. |
| 2014/0309527 A1 | 10/2014 | Namati et al. |
| 2014/0309649 A1 | 10/2014 | Alvarez et al. |
| 2014/0330114 A1 | 11/2014 | Navab |
| 2014/0350387 A1 | 11/2014 | Siewerdsen et al. |
| 2014/0354300 A1* | 12/2014 | Ramachandran ...... G01R 23/00 324/654 |
| 2014/0357953 A1 | 12/2014 | Roelle et al. |
| 2014/0357984 A1 | 12/2014 | Wallace et al. |
| 2014/0364870 A1 | 12/2014 | Alvarez et al. |
| 2014/0379000 A1 | 12/2014 | Romo et al. |
| 2015/0028195 A1 | 1/2015 | King et al. |
| 2015/0051482 A1 | 2/2015 | Liu et al. |
| 2015/0051592 A1 | 2/2015 | Kintz |
| 2015/0051732 A1 | 2/2015 | Grygorowicz et al. |
| 2015/0054929 A1 | 2/2015 | Ito et al. |
| 2015/0057507 A1 | 2/2015 | Koyrakh et al. |
| 2015/0066051 A1 | 3/2015 | Kwon et al. |
| 2015/0073266 A1 | 3/2015 | Brannan et al. |
| 2015/0101442 A1 | 4/2015 | Romo |
| 2015/0119638 A1 | 4/2015 | Yu et al. |
| 2015/0141858 A1 | 5/2015 | Razavi et al. |
| 2015/0164594 A1 | 6/2015 | Romo et al. |
| 2015/0164596 A1 | 6/2015 | Romo et al. |
| 2015/0223725 A1 | 8/2015 | Engel et al. |
| 2015/0223902 A1 | 8/2015 | Walker et al. |
| 2015/0239121 A1 | 8/2015 | Takeda |
| 2015/0248121 A1 | 9/2015 | Nilsson |
| 2015/0265368 A1 | 9/2015 | Chopra et al. |
| 2015/0271718 A1 | 9/2015 | Gopal et al. |
| 2015/0287192 A1 | 10/2015 | Sasaki |
| 2015/0289941 A1 | 10/2015 | Bowling et al. |
| 2015/0297864 A1 | 10/2015 | Kokish et al. |
| 2015/0313503 A1 | 11/2015 | Seibel et al. |
| 2015/0323398 A1 | 11/2015 | Lauzier et al. |
| 2015/0328771 A1 | 11/2015 | Yuelai et al. |
| 2015/0335480 A1 | 11/2015 | Alvarez et al. |
| 2015/0374446 A1 | 12/2015 | Malackowski et al. |
| 2016/0000520 A1 | 1/2016 | Lachmanovich et al. |
| 2016/0001038 A1 | 1/2016 | Romo et al. |
| 2016/0022189 A1 | 1/2016 | Pouteau et al. |
| 2016/0030768 A1 | 2/2016 | Ennis et al. |
| 2016/0031083 A1 | 2/2016 | Embon et al. |
| 2016/0074117 A1 | 3/2016 | Mohr |
| 2016/0100896 A1 | 4/2016 | Yu |
| 2016/0111192 A1 | 4/2016 | Suzara |
| 2016/0124220 A1 | 5/2016 | Bueeler et al. |
| 2016/0144509 A1 | 5/2016 | Gulhar et al. |
| 2016/0158601 A1 | 6/2016 | Lee et al. |
| 2016/0213432 A1 | 7/2016 | Flexman et al. |
| 2016/0221189 A1 | 8/2016 | Nilsson et al. |
| 2016/0228032 A1 | 8/2016 | Walker et al. |
| 2016/0258782 A1* | 9/2016 | Sadjadi ................ G01D 18/008 |
| 2016/0270865 A1 | 9/2016 | Landey et al. |
| 2016/0279405 A1 | 9/2016 | Riley et al. |
| 2016/0287279 A1 | 10/2016 | Bovay et al. |
| 2016/0296294 A1 | 10/2016 | Moll et al. |
| 2016/0313427 A1 | 10/2016 | Ennis et al. |
| 2016/0354925 A1 | 12/2016 | Shimodaira et al. |
| 2016/0360947 A1 | 12/2016 | Iida et al. |
| 2016/0367168 A1 | 12/2016 | Malinin et al. |
| 2016/0374541 A1 | 12/2016 | Agrawal et al. |
| 2017/0007336 A1 | 1/2017 | Tsuboi et al. |
| 2017/0007337 A1 | 1/2017 | Dan |
| 2017/0007342 A1 | 1/2017 | Kasai et al. |
| 2017/0055851 A1 | 3/2017 | Al-Ali |
| 2017/0079725 A1 | 3/2017 | Hoffman et al. |
| 2017/0079726 A1 | 3/2017 | Hoffman et al. |
| 2017/0100199 A1 | 4/2017 | Yu et al. |
| 2017/0119413 A1 | 5/2017 | Romo |
| 2017/0119481 A1 | 5/2017 | Romo et al. |
| 2017/0164870 A1 | 6/2017 | Byrd et al. |
| 2017/0165011 A1 | 6/2017 | Bovay et al. |
| 2017/0165834 A1 | 6/2017 | Hares |
| 2017/0172673 A1 | 6/2017 | Yu et al. |
| 2017/0172680 A1 | 6/2017 | Bowling et al. |
| 2017/0202627 A1 | 7/2017 | Sramek et al. |
| 2017/0209073 A1 | 7/2017 | Sramek et al. |
| 2017/0238807 A9 | 8/2017 | Vertikov |
| 2017/0245955 A1 | 8/2017 | Bowling et al. |
| 2017/0258366 A1 | 9/2017 | Tupin, Jr. et al. |

(56) References Cited

U.S. PATENT DOCUMENTS

| | | |
|---|---|---|
| 2017/0258529 A1 | 9/2017 | Winne et al. |
| 2017/0274530 A1 | 9/2017 | Mottram et al. |
| 2017/0290631 A1 | 10/2017 | Lee et al. |
| 2017/0325896 A1 | 11/2017 | Donhowe et al. |
| 2017/0333679 A1 | 11/2017 | Jiang |
| 2017/0340396 A1 | 11/2017 | Romo et al. |
| 2017/0360418 A1 | 12/2017 | Wong et al. |
| 2017/0363669 A1 | 12/2017 | Marvast et al. |
| 2017/0365055 A1 | 12/2017 | Mintz et al. |
| 2017/0367782 A1 | 12/2017 | Schuh et al. |
| 2018/0025666 A1 | 1/2018 | Ho et al. |
| 2018/0116732 A1 | 5/2018 | Lin et al. |
| 2018/0177383 A1 | 6/2018 | Noonan et al. |
| 2018/0177556 A1 | 6/2018 | Noonan |
| 2018/0177561 A1 | 6/2018 | Mintz et al. |
| 2018/0184988 A1 | 7/2018 | Walker et al. |
| 2018/0214011 A1 | 8/2018 | Graetzel et al. |
| 2018/0221038 A1 | 8/2018 | Noonan et al. |
| 2018/0221039 A1 | 8/2018 | Shah |
| 2018/0250083 A1 | 9/2018 | Schuh et al. |
| 2018/0271616 A1 | 9/2018 | Schuh et al. |
| 2018/0279852 A1 | 10/2018 | Rafii-Tari et al. |
| 2018/0280660 A1 | 10/2018 | Landey et al. |
| 2018/0289243 A1 | 10/2018 | Landey et al. |
| 2018/0289431 A1 | 10/2018 | Draper et al. |
| 2018/0325499 A1 | 11/2018 | Landey et al. |
| 2018/0333044 A1 | 11/2018 | Jenkins |
| 2018/0360435 A1 | 12/2018 | Romo |
| 2019/0000559 A1 | 1/2019 | Berman et al. |
| 2019/0000560 A1* | 1/2019 | Berman ............... A61B 34/35 |
| 2019/0000566 A1 | 1/2019 | Graetzel et al. |
| 2019/0000568 A1 | 1/2019 | Connolly et al. |
| 2019/0000576 A1 | 1/2019 | Mintz et al. |
| 2019/0083183 A1 | 3/2019 | Moll et al. |
| 2019/0105776 A1 | 4/2019 | Ho et al. |
| 2019/0105785 A1 | 4/2019 | Meyer et al. |
| 2019/0107454 A1 | 4/2019 | Lin et al. |
| 2019/0110839 A1 | 4/2019 | Rafii-Tari et al. |
| 2019/0110843 A1 | 4/2019 | Ummalaneni |
| 2019/0151148 A1 | 5/2019 | Alvarez et al. |
| 2019/0167366 A1 | 6/2019 | Ummalaneni et al. |
| 2019/0175009 A1 | 6/2019 | Mintz et al. |
| 2019/0175062 A1 | 6/2019 | Rafii-Tari et al. |
| 2019/0175287 A1 | 6/2019 | Hill et al. |
| 2019/0175799 A1 | 6/2019 | Hsu et al. |
| 2019/0183585 A1 | 6/2019 | Rafii-Tari et al. |
| 2019/0183587 A1 | 6/2019 | Rafii-Tari et al. |
| 2019/0216548 A1 | 7/2019 | Ummalaneni |
| 2019/0216576 A1 | 7/2019 | Eyre et al. |
| 2019/0223974 A1 | 7/2019 | Romo et al. |
| 2019/0228525 A1 | 7/2019 | Mintz et al. |
| 2019/0231168 A1 | 8/2019 | Hunter et al. |
| 2019/0246882 A1* | 8/2019 | Graetzel ............ A61B 1/0002 |
| 2019/0262086 A1 | 8/2019 | Connolly et al. |
| 2019/0269468 A1 | 9/2019 | Hsu et al. |
| 2019/0274764 A1 | 9/2019 | Romo |
| 2019/0290109 A1 | 9/2019 | Agrawal et al. |
| 2019/0298160 A1* | 10/2019 | Ummalaneni ......... A61B 34/30 |
| 2019/0298460 A1 | 10/2019 | Al-Jadda et al. |
| 2019/0298465 A1 | 10/2019 | Chin et al. |
| 2019/0328213 A1 | 10/2019 | Landey et al. |
| 2019/0336238 A1 | 11/2019 | Yu et al. |
| 2019/0343421 A1* | 11/2019 | Yanof ................. A61B 5/746 |
| 2019/0365209 A1 | 12/2019 | Ye et al. |
| 2019/0365479 A1 | 12/2019 | Rafii-Tari |
| 2019/0365486 A1 | 12/2019 | Srinivasan et al. |
| 2019/0365491 A1 | 12/2019 | Yu |
| 2019/0374297 A1 | 12/2019 | Wallace et al. |
| 2019/0375383 A1 | 12/2019 | Auer |
| 2019/0380787 A1 | 12/2019 | Ye et al. |
| 2019/0380797 A1 | 12/2019 | Yu et al. |
| 2020/0000530 A1 | 1/2020 | DeFonzo et al. |
| 2020/0000533 A1 | 1/2020 | Schuh et al. |
| 2020/0022767 A1 | 1/2020 | Hill et al. |
| 2020/0038123 A1 | 2/2020 | Graetzel et al. |
| 2020/0121401 A1 | 4/2020 | Malinin et al. |
| 2020/0138330 A1 | 5/2020 | Thompson et al. |
| 2020/0138334 A1 | 5/2020 | Hill et al. |
| 2020/0138525 A1 | 5/2020 | Hill et al. |
| 2020/0337783 A1* | 10/2020 | Bono .................... A61B 34/30 |
| 2020/0352420 A1 | 11/2020 | Graetzel et al. |
| 2020/0367981 A1 | 11/2020 | Ho et al. |
| 2020/0372409 A1* | 11/2020 | Srivastava ............... G01D 5/00 |
| 2021/0045822 A1 | 2/2021 | Landey et al. |
| 2021/0045823 A1 | 2/2021 | Landey et al. |
| 2021/0045824 A1 | 2/2021 | Landey et al. |
| 2021/0059764 A1 | 3/2021 | Rafii-Tari et al. |
| 2021/0059766 A1 | 3/2021 | Graetzel et al. |
| 2021/0121052 A1 | 4/2021 | Graetzel et al. |
| 2021/0137609 A1 | 5/2021 | Srinivasan et al. |
| 2021/0137617 A1 | 5/2021 | Srinivasan et al. |
| 2021/0161603 A1 | 6/2021 | Berman et al. |
| 2021/0169588 A1 | 6/2021 | Graetzel et al. |
| 2021/0196293 A1 | 7/2021 | Lin et al. |
| 2021/0196399 A1 | 7/2021 | Ayvali et al. |
| 2021/0369384 A1 | 12/2021 | Lin et al. |

FOREIGN PATENT DOCUMENTS

| | | |
|---|---|---|
| EP | 0830562 B1 | 7/2009 |
| EP | 3025630 A1 | 6/2016 |
| EP | 3282944 A1 | 2/2018 |
| EP | 3282995 A1 | 2/2018 |
| EP | 3463136 B1 | 12/2020 |
| GB | 2524498 A | 9/2015 |
| JP | 2018526049 A | 9/2018 |
| JP | 2019527572 A | 10/2019 |
| KR | 1020140009359 A | 1/2014 |
| KR | 20190054030 A | 5/2019 |
| LT | 2019520 A | 6/2020 |
| WO | 2009097461 A1 | 8/2009 |
| WO | 2011150526 A1 | 12/2011 |
| WO | 2012155050 A2 | 11/2012 |
| WO | 2014144633 A1 | 9/2014 |
| WO | 2014144662 A1 | 9/2014 |
| WO | 2015013470 A2 | 1/2015 |
| WO | 2015142585 A1 | 9/2015 |
| WO | 2017167754 A1 | 10/2017 |
| WO | 2018064394 A1 | 4/2018 |
| WO | 2018183727 A1 | 10/2018 |
| WO | 2019005872 A1 | 1/2019 |
| WO | 2019005992 A1 | 1/2019 |
| WO | 2019160865 A1 | 8/2019 |
| WO | 2019191144 A1 | 10/2019 |
| WO | 2019231891 A1 | 12/2019 |
| WO | 2020033318 A1 | 2/2020 |
| WO | 2020069430 A1 | 4/2020 |
| WO | 2021028889 A1 | 2/2021 |
| WO | 2021038469 A1 | 3/2021 |
| WO | 2021044297 A1 | 3/2021 |
| WO | 2021137071 A1 | 7/2021 |

OTHER PUBLICATIONS

Written opinion for appl No. WO2021044297, dated Mar. 11, 2021, 4 pages.
Advisory Action for U.S. Appl. No. 16/017,924, dated Jun. 21, 2019, 3 pages.
Ciuti et al., 2012, Intra-operative monocular 3D reconstruction for image-guided navigation in active locomotion capsule endoscopy. Biomedical Robotics And Biomechatronics (Biorob), 4th IEEE Ras & Embs International Conference On IEEE, 7 pages.
European Search Report dated Feb. 17, 2021 for EP Patent Appl. No. 18825186.2, 10 pages.
Fallavoliita et al., 2010, Acquiring multiview C-arm images to assist cardiac ablation procedures, EURASIP Journal on Image and Video Processing, vol. 2010, Article ID 871408, pp. 1-10.
Final Rejection for U.S. Appl. No. 16/017,924, dated Apr. 10, 2019, 9 pages.
Final Rejection for U.S. Appl. No. 16/017,924, dated Jan. 7, 2019, 12 pages.

(56) References Cited

OTHER PUBLICATIONS

Haigron et al., 2004, Depth-map-based scene analysis for active navigation in virtual angioscopy, IEEE Transactions an Medical Imaging, 23(11): 1380-1390.
International Search Report and Written Opinion dated Sep. 18, 2018 in application No. PCT/US2018/039351, 10 pages.
Kumar et al., 2014, Stereoscopic visualization of laparoscope image using depth information from 3D model, Computer methods and programs in biomedicine 113(3):862-868.
Livatino et al., 2015, Stereoscopic visualization and 3-D technologies in medical endoscopic teleoperation, IEEE, 11 pages.
Luo et al., 2010, Modified hybrid bronchoscope tracking based on sequential monte carlo sampler: Dynamic phantom validation, Asian Conference on Computer Vision. Springer, Berlin, Heidelberg, 13 pages.
Mayo Clinic, Robotic Surgery, https://www.mayoclinic.org/tests-procedures/mbotic-surgery/about/pac- 20394974?p=1, downloaded from the internet on Jul. 12, 2018, 2 pp.
Mourgues et al., 2002, Flexible calibration of actuated stereoscopic endoscope for overlay inrobot assisted surgery, International Conference on Medical Image Computing and Computer-AssistedIntervention. Springer, Berlin, Heidelbe, 10 pages.
Nadeem et al., 2016, Depth Reconstruction and Computer-Aided Polyp Detection in Optical Colonoscopy Video Frames, arXiv preprint arXiv: 1609.01329, 12 pages.
Non Final Rejection for U.S. Appl. No. 16/017,924, dated Aug. 30, 2018, 12 pages.
Notice of allowance for U.S. Appl. No. 16/017,924, dated Apr. 19, 2021, 8 pages.
Notice of Allowance for U.S. Appl. No. 16/017,924, dated Sep. 13, 2021, 8 pages.
Point Cloud, Sep. 10, 2010, Wikipedia, 2 pp.
Racadio et al., Dec. 2007, Live 3D guidance in the interventionail radiology suite, AJR, 189:W357-W364, 8 pages.
S1en et al., 2015, Robust camera localisation with dept 1 reconstruction for bronchoscopic navigation. International Journal of Computer Assisted Radiology and Surgery, 10(6):801-813.
Sato et al., 2016, Techniques of stapler-based navigational thoracoscopic segmentectomy using virtual assisted lung mapping (VAL-MAP), Journal of Thoracic Disease, 8(Suppl 9):S71,15 pages.
Soiheim et ai., May 14, 2009, Navigated resection of giant intracranial meningiomas based on intraoperative 30 ultrasound, Acta Neurochir, 151:1143-1151.
Song et al., 2012, Autonomous and stable tracking of endoscope instrument tools with monocular camera, Advanced Intelligent Mechatronics (AiM), 2012 IEEE-ASME International Conference on. IEEE, 6 pages.
Verdaasdonk et al., Jan. 23, 2012, Effect of microsecond pulse length and tip shape on explosive bubble formation of 2.78 μm Er,Cr;YSGG and 2.94 pm Er:YAG laser, Proceedings of SPIE, vol. 8221, 1 page.
Yip et al., 2012, Tissue tracking and registration for image-guided surgery, IEEE transactions on medical imaging 31 (11):2169-2182, 14 pages.
Zhou et al., 2010, Synthesis of stereoscopic views from monocular endoscopic videos, Compute Vision and Pattern Recognition Workshops (CVPRVV), 2010 IEEE Computer Society Conference on IEEE, 8 pages.
Advisory Action for U.S. Appl. No. 16/017,906, dated Mar. 29, 2019, 3 pages.
Extended European Search Report dated Oct. 1, 2020 in patent application No. 18824393.5, 7 pages.
Final Rejection for U.S. Appl. No. 16/017,906, dated Jan. 18, 2019, 10 pages.
Final Rejection for U.S. Appl. No. 16/017,906, dated Nov. 16, 2021, 13 pages.
Final Rejection for U.S. Appl. No. 16/017,906, dated Nov. 6, 2019, 11 pages.
International Search Report and Written Opinion dated Sep. 12, 2018 in application No. PCT/US18/39357, 7 pages.
Non Final Rejection for U.S. Appl. No. 16/017,906, dated Apr. 22, 2019, 12 pages.
Non Final Rejection for U.S. Appl. No. 16/017,906, dated Aug. 30, 2018, 10 pages.
Non Final Rejection for U.S. Appl. No. 16/017,906, dated Mar. 24, 2021, 15 pages.
Notice Of Allowance for U.S. Appl. No. 16/017,906, dated Aug. 20, 2020, 6 pages.
Skarecky et al., 2008, Zero positive surgical margins after radical prostatectomy: is the end in sight?, Expert Review of Medical Devices, 5 (6): 709-717, 10 pages.
Verdaasdonk et al., Jan. 23, 2012, Effect of microsecond pulse length and tip shape on explosive bubble formation of 2.78 um Er, Cr; YSGG and 2.94 um Er; YAG laser, Proceedings of SPIE, vol. 8221, 12, 1 page.
International Preliminary Report on Patnentability and Written Opinion for appl No. PCT/IB2020/058141, dated Mar. 17, 2022, 5 pages.

\* cited by examiner

US 11,324,558 B2

ELECTROMAGNETIC DISTORTION DETECTION AND COMPENSATION

CROSS-REFERENCE TO RELATED APPLICATION(S)

This application claims the benefit of U.S. Provisional Application No. 62/895,272, filed Sep. 3, 2019, which is hereby incorporated by reference in its entirety.

TECHNICAL FIELD

The present disclosure relates generally to systems and methods for the detection of electromagnetic (EM) distortion in robotically-enabled medical system, and more particularly to compensating for detected EM distortions which may affect EM based navigation systems used for navigation and localization of medical instruments within a patient.

BACKGROUND

Medical procedures such as endoscopy (e.g., bronchoscopy) may involve accessing and visualizing the inside of a patient's luminal network (e.g., airways) for diagnostic and/or therapeutic purposes. Surgical robotic systems may be used to control the insertion and/or manipulation of a surgical tool, such as, for example, an endoscope during an endoscopic procedure. The surgical robotic system may comprise at least one robotic arm including a manipulator assembly used to control the positioning of the surgical tool during the procedure. The surgical tool may be navigated through the patient's luminal network based on a detected electromagnetic (EM) field.

SUMMARY

The systems, methods and devices of this disclosure each have several innovative aspects, no single one of which is solely responsible for the desirable attributes disclosed herein.

In one aspect, there is provided a system, comprising: an instrument comprising a set of one or more electromagnetic (EM) sensors, the EM sensors configured to generate EM location data indicative of one or more a positions of a distal end of the instrument; or more processors; and at least one computer-readable memory in communication with the one or more processors and having stored thereon computer-executable instructions to cause the one or more processors to: determine a reference position of the distal end of the instrument at a first time based on the EM location data, determine that the distal end of the instrument at a second time is static, the second time subsequent to the first time, determine that the EM location data at the second time is indicative of a the position of the distal end of the instrument at the second time having changed from the reference position by greater than a threshold distance, determine a current offset based on the distance between the position at the second time and the reference position at the first time, and determine a compensated position of the distal end of the instrument based on the EM location data and the current offset.

In another aspect, there is provided a method of compensating for electromagnetic (EM) distortion, comprising: determining a reference position of a distal end of an instrument at a first time based on EM location data, the instrument comprising a set of one or more EM sensors configured to generate the EM location data indicative of a position of the distal end of the instrument; determining that the distal end of the instrument at a second time is static, the second time subsequent to the first time; determining that the EM location data at the second time is indicative of the position of the distal end of the instrument at the second time having changed from the reference position by greater than a threshold distance; determining a current offset based on the distance between the position at the second time and the reference position at the first time; and determining a compensated position of the distal end of the instrument based on the EM location data and the current offset.

In yet another aspect, there is provided a non-transitory computer readable storage medium having stored thereon instructions that, when executed, cause at least one computing device to: determine a reference position of a distal end of an instrument at a first time based on EM location data, the instrument comprising a set of one or more EM sensors configured to generate the EM location data indicative of a position of the distal end of the instrument; determine that the distal end of the instrument at a second time is static, the second time subsequent to the first time; determine that the EM location data at the second time is indicative of the position of the distal end of the instrument at the second time having changed from the reference position by greater than a threshold distance; determine a current offset based on the distance between the position at the second time and the reference position at the first time; and determine a compensated position of the distal end of the instrument based on the EM location data and the current offset.

In still yet another aspect, there is provided a system, comprising: an instrument comprising a set of one or more location sensors, the location sensors configured to location data indicative of a position of a distal end of the instrument; a set of one or more processors; and at least one computer-readable memory in communication with the set of one or more processors and having stored thereon computer-executable instructions to cause the one or more processors to: determine a reference position of the distal end of the instrument at a first time based on the location data, determine that the distal end of the instrument at a second time is static, the second time subsequent to the first time, determine that the EM location data at the second time is indicative of the position of the distal end of the instrument at the second time having changed from the reference position by greater than a threshold distance, and determine a compensated position of the distal end of the instrument based on the location data and the determination that the position of the distal end of the instrument at the second time has changed from the reference position by greater than a threshold distance.

BRIEF DESCRIPTION OF THE DRAWINGS

The disclosed aspects will hereinafter be described in conjunction with the appended drawings, provided to illustrate and not to limit the disclosed aspects, wherein like designations denote like elements.

DETAILED DESCRIPTION

Figure 1:
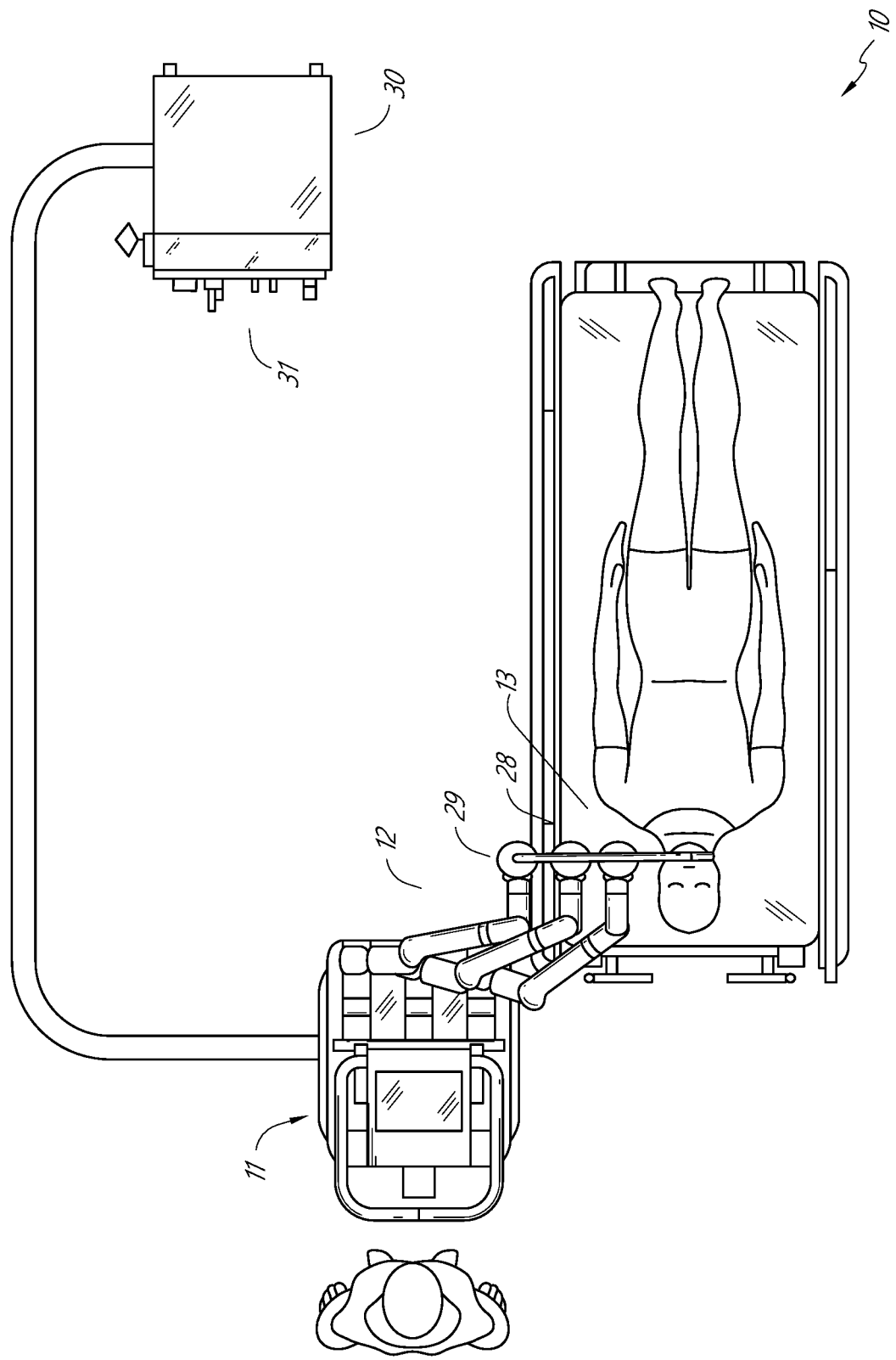
FIG. 1 illustrates an embodiment of a cart-based robotic system arranged for diagnostic and/or therapeutic bronchoscopy procedure(s).

Embodiments of this disclosure relate to systems and techniques for the detection and/or mitigation of electromagnetic (EM) distortion which may cause errors in localization and/or navigation systems that rely on EM data. There are a number of possible sources of EM distortion, which may in extreme cases of distortion, cause the EM data to be unreliable. Additional embodiments of this disclosure relate to techniques for alignment of an EM generator with respect to a patient and/or one or more EM patch sensors placed on the patient.

As used herein, the term "approximately" refers to a range of measurements of a length, thickness, a quantity, time period, or other measurable value. Such range of measurements encompasses variations of +/−10% or less, preferably +/−5% or less, more preferably +/−1% or less, and still more preferably +/−0.1% or less, of and from the specified value, in so far as such variations are appropriate in order to function in the disclosed devices, systems, and techniques.

Various embodiments will be described below in conjunction with the drawings for purposes of illustration. It should be appreciated that many other implementations of the disclosed concepts are possible, and various advantages can be achieved with the disclosed implementations. Headings are included herein for reference and to aid in locating various sections. These headings are not intended to limit the scope of the concepts described with respect thereto. Such concepts may have applicability throughout the entire specification.

1. Overview.

Aspects of the present disclosure may be integrated into a robotically-enabled medical system capable of performing a variety of medical procedures, including both minimally invasive, such as laparoscopy, and non-invasive, such as endoscopy, procedures. Among endoscopy procedures, the system may be capable of performing bronchoscopy, ureteroscopy, gastroscopy, etc.

In addition to performing the breadth of procedures, the system may provide additional benefits, such as enhanced imaging and guidance to assist the physician. Additionally, the system may provide the physician with the ability to perform the procedure from an ergonomic position without the need for awkward arm motions and positions. Still further, the system may provide the physician with the ability to perform the procedure with improved ease of use such that one or more of the instruments of the system can be controlled by a single user.

Various embodiments will be described below in conjunction with the drawings for purposes of illustration. It should be appreciated that many other implementations of the disclosed concepts are possible, and various advantages can be achieved with the disclosed implementations. Headings are included herein for reference and to aid in locating various sections. These headings are not intended to limit the scope of the concepts described with respect thereto. Such concepts may have applicability throughout the entire specification.

A. Robotic System—Cart.

Figure 2:
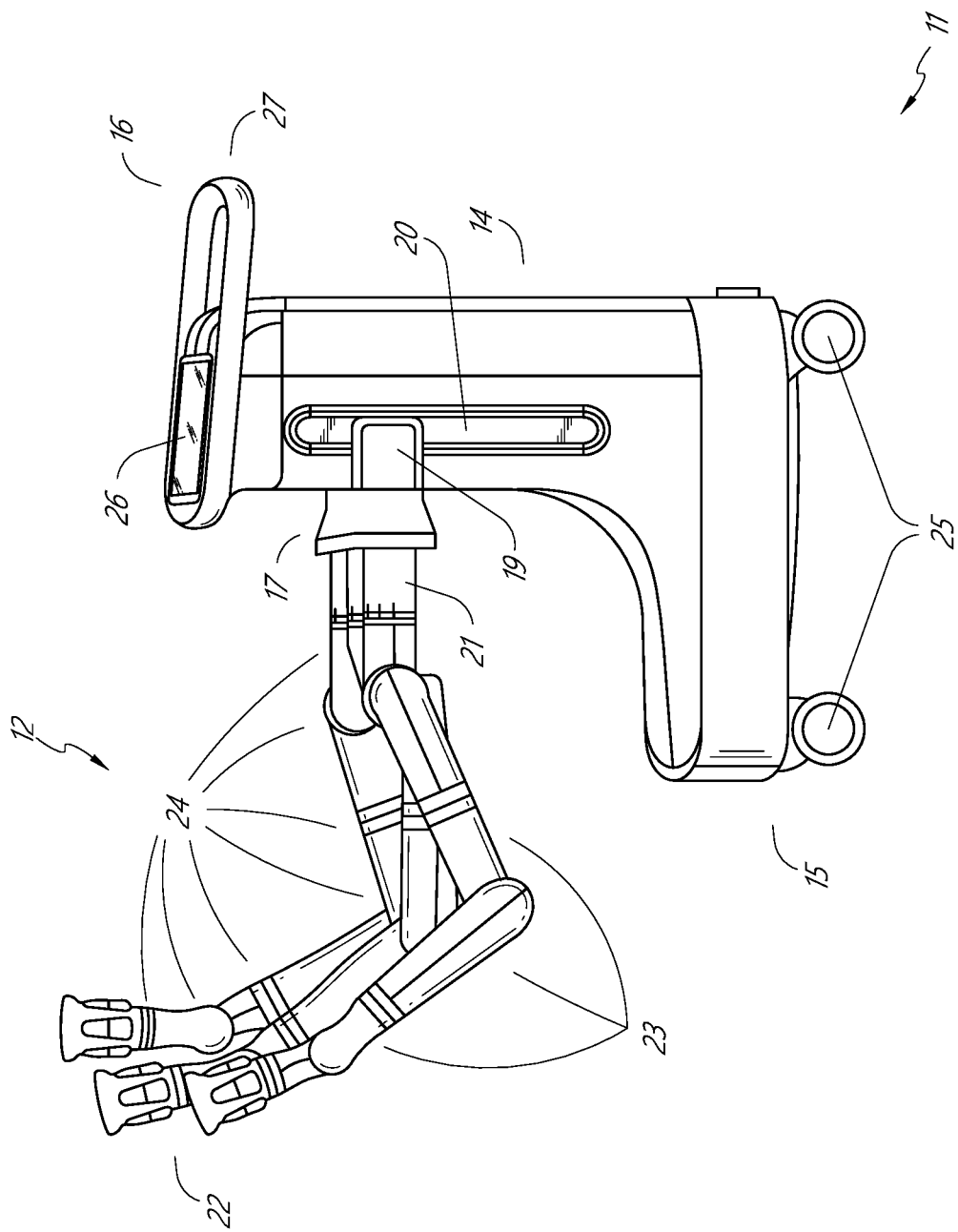
FIG. 2 depicts further aspects of the robotic system of FIG. 1.

The robotically-enabled medical system may be configured in a variety of ways depending on the particular procedure. FIG. 1 illustrates an embodiment of a cart-based robotically-enabled system 10 arranged for a diagnostic and/or therapeutic bronchoscopy procedure. During a bronchoscopy, the system 10 may comprise a cart 11 having one or more robotic arms 12 to deliver a medical instrument, such as a steerable endoscope 13, which may be a procedure-specific bronchoscope for bronchoscopy, to a natural orifice access point (i.e., the mouth of the patient positioned on a table in the present example) to deliver diagnostic and/or therapeutic tools. As shown, the cart 11 may be positioned proximate to the patient's upper torso in order to provide access to the access point. Similarly, the robotic arms 12 may be actuated to position the bronchoscope relative to the access point. The arrangement in FIG. 1 may also be utilized when performing a gastro-intestinal (GI) procedure with a gastroscope, a specialized endoscope for GI procedures. FIG. 2 depicts an example embodiment of the cart in greater detail.

With continued reference to FIG. 1, once the cart 11 is properly positioned, the robotic arms 12 may insert the steerable endoscope 13 into the patient robotically, manually, or a combination thereof. As shown, the steerable endoscope 13 may comprise at least two telescoping parts, such as an inner leader portion and an outer sheath portion, each portion coupled to a separate instrument driver from the set of instrument drivers 28, each instrument driver coupled to the distal end of an individual robotic arm. This linear arrangement of the instrument drivers 28, which facilitates coaxially aligning the leader portion with the sheath portion, creates a "virtual rail" 29 that may be repositioned in space by manipulating the one or more robotic arms 12 into different angles and/or positions. The virtual rails described herein are depicted in the Figures using dashed lines, and accordingly the dashed lines do not depict any physical structure of the system. Translation of the instrument drivers 28 along the virtual rail 29 telescopes the inner leader portion relative to the outer sheath portion or advances or retracts the endoscope 13 from the patient. The angle of the virtual rail 29 may be adjusted, translated, and pivoted based on clinical application or physician preference. For example, in bronchoscopy, the angle and position of the virtual rail 29 as shown represents a compromise between providing physician access to the endoscope 13 while minimizing friction that results from bending the endoscope 13 into the patient's mouth.

The endoscope 13 may be directed down the patient's trachea and lungs after insertion using precise commands from the robotic system until reaching the target destination or operative site. In order to enhance navigation through the patient's lung network and/or reach the desired target, the endoscope 13 may be manipulated to telescopically extend the inner leader portion from the outer sheath portion to obtain enhanced articulation and greater bend radius. The use of separate instrument drivers 28 also allows the leader portion and sheath portion to be driven independent of each other.

For example, the endoscope 13 may be directed to deliver a biopsy needle to a target, such as, for example, a lesion or nodule within the lungs of a patient. The needle may be deployed down a working channel that runs the length of the endoscope to obtain a tissue sample to be analyzed by a pathologist. Depending on the pathology results, additional tools may be deployed down the working channel of the endoscope for additional biopsies. After identifying a nodule to be malignant, the endoscope 13 may endoscopically deliver tools to resect the potentially cancerous tissue. In some instances, diagnostic and therapeutic treatments may need to be delivered in separate procedures. In those circumstances, the endoscope 13 may also be used to deliver a fiducial to "mark" the location of the target nodule as well. In other instances, diagnostic and therapeutic treatments may be delivered during the same procedure.

The system 10 may also include a movable tower 30, which may be connected via support cables to the cart 11 to provide support for controls, electronics, fluidics, optics, sensors, and/or power to the cart 11. Placing such functionality in the tower 30 allows for a smaller form factor cart 11 that may be more easily adjusted and/or re-positioned by an operating physician and his/her staff. Additionally, the division of functionality between the cart/table and the support tower 30 reduces operating room clutter and facilitates improving clinical workflow. While the cart 11 may be positioned close to the patient, the tower 30 may be stowed in a remote location to stay out of the way during a procedure.

In support of the robotic systems described above, the tower 30 may include component(s) of a computer-based control system that stores computer program instructions, for example, within a non-transitory computer-readable storage medium such as a persistent magnetic storage drive, solid state drive, etc. The execution of those instructions, whether the execution occurs in the tower 30 or the cart 11, may control the entire system or sub-system(s) thereof. For example, when executed by a processor of the computer system, the instructions may cause the components of the robotics system to actuate the relevant carriages and arm mounts, actuate the robotics arms, and control the medical instruments. For example, in response to receiving the control signal, the motors in the joints of the robotics arms may position the arms into a certain posture.

The tower 30 may also include a pump, flow meter, valve control, and/or fluid access in order to provide controlled irrigation and aspiration capabilities to system that may be deployed through the endoscope 13. These components may also be controlled using the computer system of tower 30. In some embodiments, irrigation and aspiration capabilities may be delivered directly to the endoscope 13 through separate cable(s).

The tower 30 may include a voltage and surge protector designed to provide filtered and protected electrical power to the cart 11, thereby avoiding placement of a power transformer and other auxiliary power components in the cart 11, resulting in a smaller, more moveable cart 11.

The tower 30 may also include support equipment for the sensors deployed throughout the robotic system 10. For example, the tower 30 may include opto-electronics equipment for detecting, receiving, and processing data received from the optical sensors or cameras throughout the robotic system 10. In combination with the control system, such opto-electronics equipment may be used to generate real-time images for display in any number of consoles deployed throughout the system, including in the tower 30. Similarly, the tower 30 may also include an electronic subsystem for receiving and processing signals received from deployed EM sensors. The tower 30 may also be used to house and position an EM field generator for detection by EM sensors in or on the medical instrument.

The tower 30 may also include a console 31 in addition to other consoles available in the rest of the system, e.g., console mounted on top of the cart. The console 31 may include a user interface and a display screen, such as a touchscreen, for the physician operator. Consoles in system 10 are generally designed to provide both robotic controls as well as pre-operative and real-time information of the procedure, such as navigational and localization information of the endoscope 13. When the console 31 is not the only console available to the physician, it may be used by a second operator, such as a nurse, to monitor the health or vitals of the patient and the operation of system, as well as provide procedure-specific data, such as navigational and localization information.

The tower 30 may be coupled to the cart 11 and endoscope 13 through one or more cables or connections (not shown). In some embodiments, the support functionality from the tower 30 may be provided through a single cable to the cart 11, simplifying and de-cluttering the operating room. In other embodiments, specific functionality may be coupled in separate cabling and connections. For example, while power may be provided through a single power cable to the cart, the support for controls, optics, fluidics, and/or navigation may be provided through a separate cable.

FIG. 2 provides a detailed illustration of an embodiment of the cart from the cart-based robotically-enabled system shown in FIG. 1. The cart 11 generally includes an elongated support structure 14 (often referred to as a "column"), a cart base 15, and a console 16 at the top of the column 14. The column 14 may include one or more carriages, such as a carriage 17 (alternatively "arm support") for supporting the deployment of one or more robotic arms 12 (three shown in FIG. 2). The carriage 17 may include individually configurable arm mounts that rotate along a perpendicular axis to adjust the base of the robotic arms 12 for better positioning relative to the patient. The carriage 17 also includes a carriage interface 19 that allows the carriage 17 to vertically translate along the column 14.

The carriage interface 19 is connected to the column 14 through slots, such as slot 20, that are positioned on opposite sides of the column 14 to guide the vertical translation of the carriage 17. The slot 20 contains a vertical translation interface to position and hold the carriage at various vertical heights relative to the cart base 15. Vertical translation of the carriage 17 allows the cart 11 to adjust the reach of the robotic arms 12 to meet a variety of table heights, patient sizes, and physician preferences. Similarly, the individually configurable arm mounts on the carriage 17 allow the robotic arm base 21 of robotic arms 12 to be angled in a variety of configurations.

In some embodiments, the slot 20 may be supplemented with slot covers that are flush and parallel to the slot surface to prevent dirt and fluid ingress into the internal chambers of the column 14 and the vertical translation interface as the carriage 17 vertically translates. The slot covers may be deployed through pairs of spring spools positioned near the vertical top and bottom of the slot 20. The covers are coiled within the spools until deployed to extend and retract from their coiled state as the carriage 17 vertically translates up and down. The spring-loading of the spools provides force to retract the cover into a spool when carriage 17 translates towards the spool, while also maintaining a tight seal when the carriage 17 translates away from the spool. The covers may be connected to the carriage 17 using, for example, brackets in the carriage interface 19 to ensure proper extension and retraction of the cover as the carriage 17 translates.

The column 14 may internally comprise mechanisms, such as gears and motors, that are designed to use a vertically aligned lead screw to translate the carriage 17 in a mechanized fashion in response to control signals generated in response to user inputs, e.g., inputs from the console 16.

The robotic arms 12 may generally comprise robotic arm bases 21 and end effectors 22, separated by a series of linkages 23 that are connected by a series of joints 24, each joint comprising an independent actuator, each actuator comprising an independently controllable motor. Each independently controllable joint represents an independent degree of freedom available to the robotic arm. Each of the arms 12 have seven joints, and thus provide seven degrees of freedom. A multitude of joints result in a multitude of degrees of freedom, allowing for "redundant" degrees of freedom. Redundant degrees of freedom allow the robotic arms 12 to position their respective end effectors 22 at a specific position, orientation, and trajectory in space using different linkage positions and joint angles. This allows for the system to position and direct a medical instrument from a desired point in space while allowing the physician to move the arm joints into a clinically advantageous position away from the patient to create greater access, while avoiding arm collisions.

The cart base 15 balances the weight of the column 14, carriage 17, and arms 12 over the floor. Accordingly, the cart base 15 houses heavier components, such as electronics, motors, power supply, as well as components that either enable movement and/or immobilize the cart. For example, the cart base 15 includes rollable wheel-shaped casters 25 that allow for the cart to easily move around the room prior to a procedure. After reaching the appropriate position, the casters 25 may be immobilized using wheel locks to hold the cart 11 in place during the procedure.

Positioned at the vertical end of column 14, the console 16 allows for both a user interface for receiving user input and a display screen (or a dual-purpose device such as, for example, a touchscreen 26) to provide the physician user with both pre-operative and intra-operative data. Potential pre-operative data on the touchscreen 26 may include pre-operative plans, navigation and mapping data derived from pre-operative computerized tomography (CT) scans, and/or notes from pre-operative patient interviews. Intra-operative data on display may include optical information provided from the tool, sensor and coordinate information from sensors, as well as vital patient statistics, such as respiration, heart rate, and/or pulse. The console 16 may be positioned and tilted to allow a physician to access the console from the side of the column 14 opposite carriage 17. From this position the physician may view the console 16, robotic arms 12, and patient while operating the console 16 from behind the cart 11. As shown, the console 16 also includes a handle 27 to assist with maneuvering and stabilizing cart 11.

Figure 3:
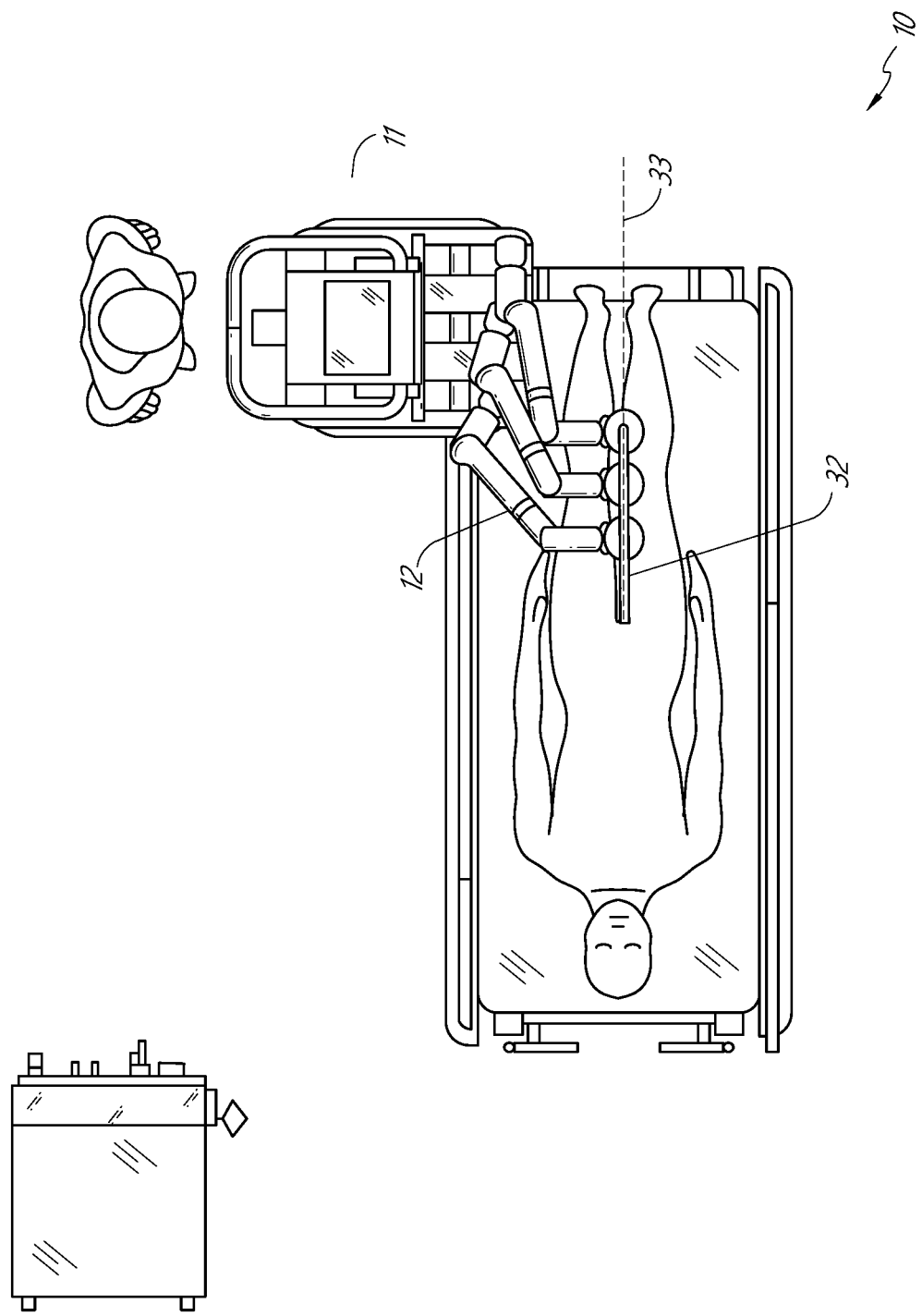
FIG. 3 illustrates an embodiment of the robotic system of FIG. 1 arranged for ureteroscopy.

FIG. 3 illustrates an embodiment of a robotically-enabled system 10 arranged for ureteroscopy. In a ureteroscopic procedure, the cart 11 may be positioned to deliver a ureteroscope 32, a procedure-specific endoscope designed to traverse a patient's urethra and ureter, to the lower abdominal area of the patient. In ureteroscopy, it may be desirable for the ureteroscope 32 to be directly aligned with the patient's urethra to reduce friction and forces on the sensitive anatomy in the area. As shown, the cart 11 may be aligned at the foot of the table to allow the robotic arms 12 to position the ureteroscope 32 for direct linear access to the patient's urethra. From the foot of the table, the robotic arms 12 may insert ureteroscope 32 along the virtual rail 33 directly into the patient's lower abdomen through the urethra.

After insertion into the urethra, using similar control techniques as in bronchoscopy, the ureteroscope 32 may be navigated into the bladder, ureters, and/or kidneys for diagnostic and/or therapeutic applications. For example, the ureteroscope 32 may be directed into the ureter and kidneys to break up kidney stone build up using laser or ultrasonic lithotripsy device deployed down the working channel of the ureteroscope 32. After lithotripsy is complete, the resulting stone fragments may be removed using baskets deployed down the ureteroscope 32.

Figure 4:
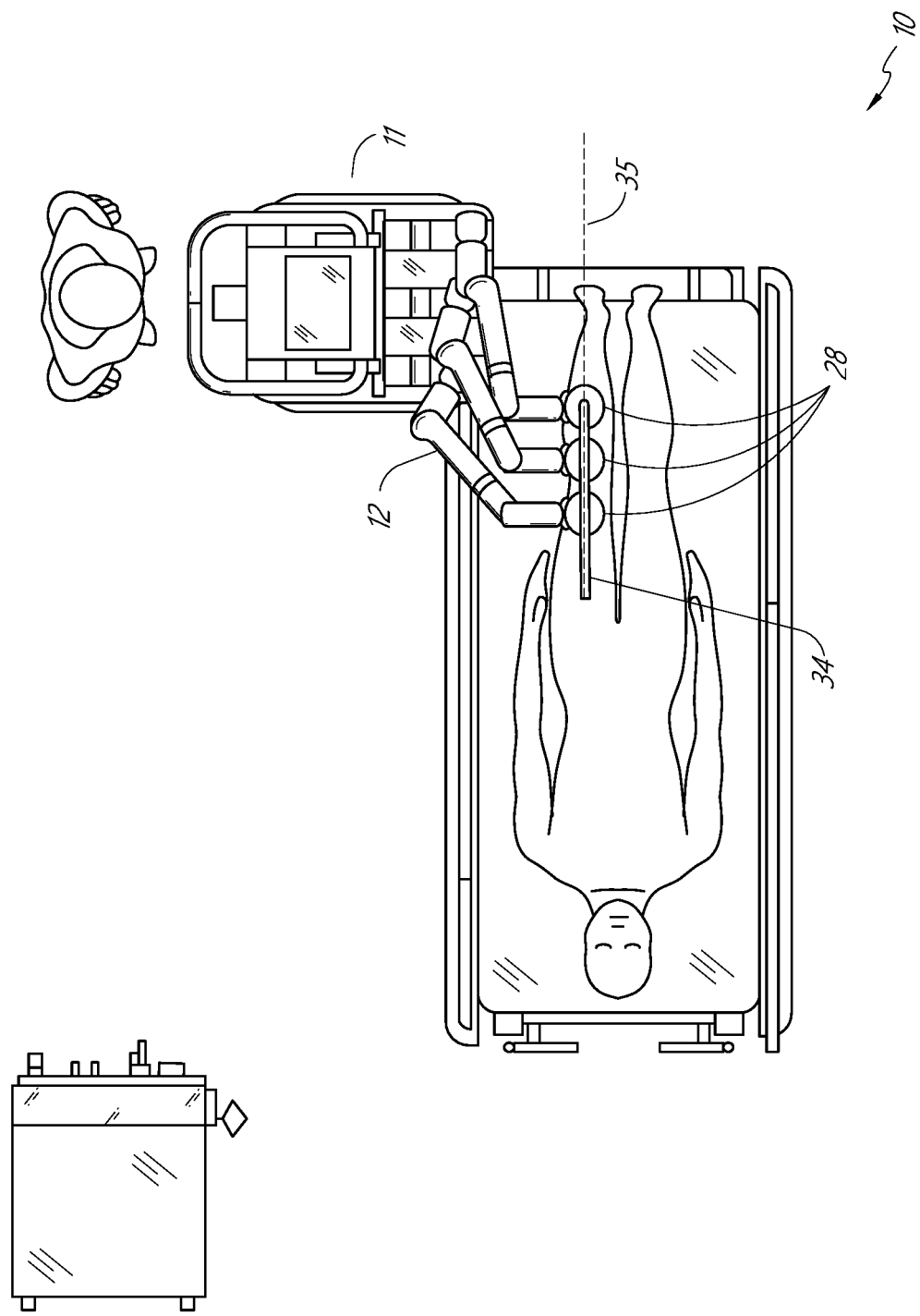
FIG. 4 illustrates an embodiment of the robotic system of FIG. 1 arranged for a vascular procedure.

FIG. 4 illustrates an embodiment of a robotically-enabled system similarly arranged for a vascular procedure. In a vascular procedure, the system 10 may be configured such the cart 11 may deliver a medical instrument 34, such as a steerable catheter, to an access point in the femoral artery in the patient's leg. The femoral artery presents both a larger diameter for navigation as well as relatively less circuitous and tortuous path to the patient's heart, which simplifies navigation. As in a ureteroscopic procedure, the cart 11 may be positioned towards the patient's legs and lower abdomen to allow the robotic arms 12 to provide a virtual rail 35 with direct linear access to the femoral artery access point in the patient's thigh/hip region. After insertion into the artery, the medical instrument 34 may be directed and inserted by translating the instrument drivers 28. Alternatively, the cart may be positioned around the patient's upper abdomen in order to reach alternative vascular access points, such as, for example, the carotid and brachial arteries near the shoulder and wrist.

B. Robotic System—Table.

Figure 5:
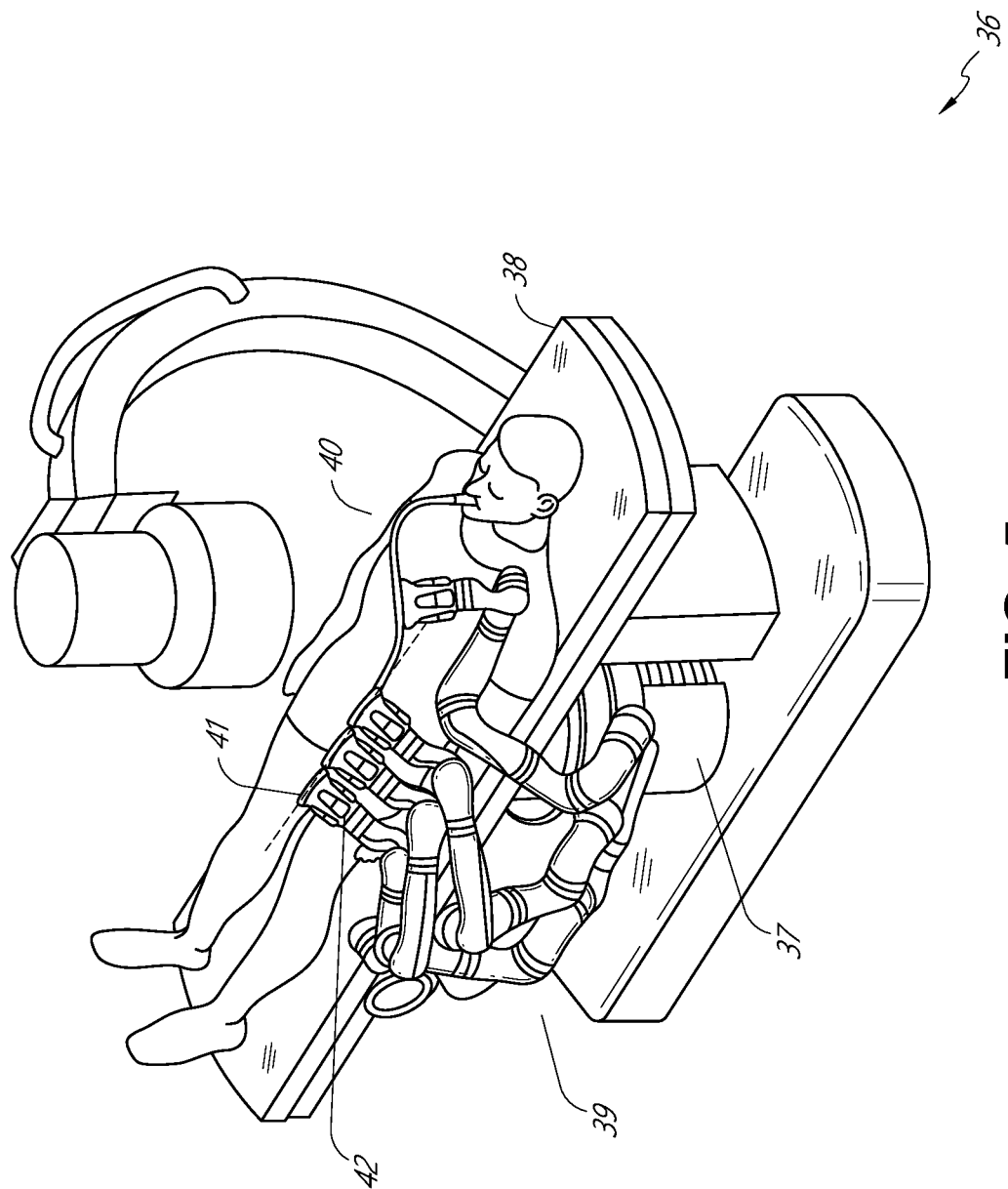
FIG. 5 illustrates an embodiment of a table-based robotic system arranged for a bronchoscopy procedure.

Embodiments of the robotically-enabled medical system may also incorporate the patient's table. Incorporation of the table reduces the amount of capital equipment within the operating room by removing the cart, which allows greater access to the patient. FIG. 5 illustrates an embodiment of such a robotically-enabled system arranged for a bronchoscopy procedure. System 36 includes a support structure or column 37 for supporting platform 38 (shown as a "table" or "bed") over the floor. Much like in the cart-based systems, the end effectors of the robotic arms 39 of the system 36 comprise instrument drivers 42 that are designed to manipulate an elongated medical instrument, such as a bronchoscope 40 in FIG. 5, through or along a virtual rail 41 formed from the linear alignment of the instrument drivers 42. In practice, a C-arm for providing fluoroscopic imaging may be positioned over the patient's upper abdominal area by placing the emitter and detector around table 38.

Figure 6:
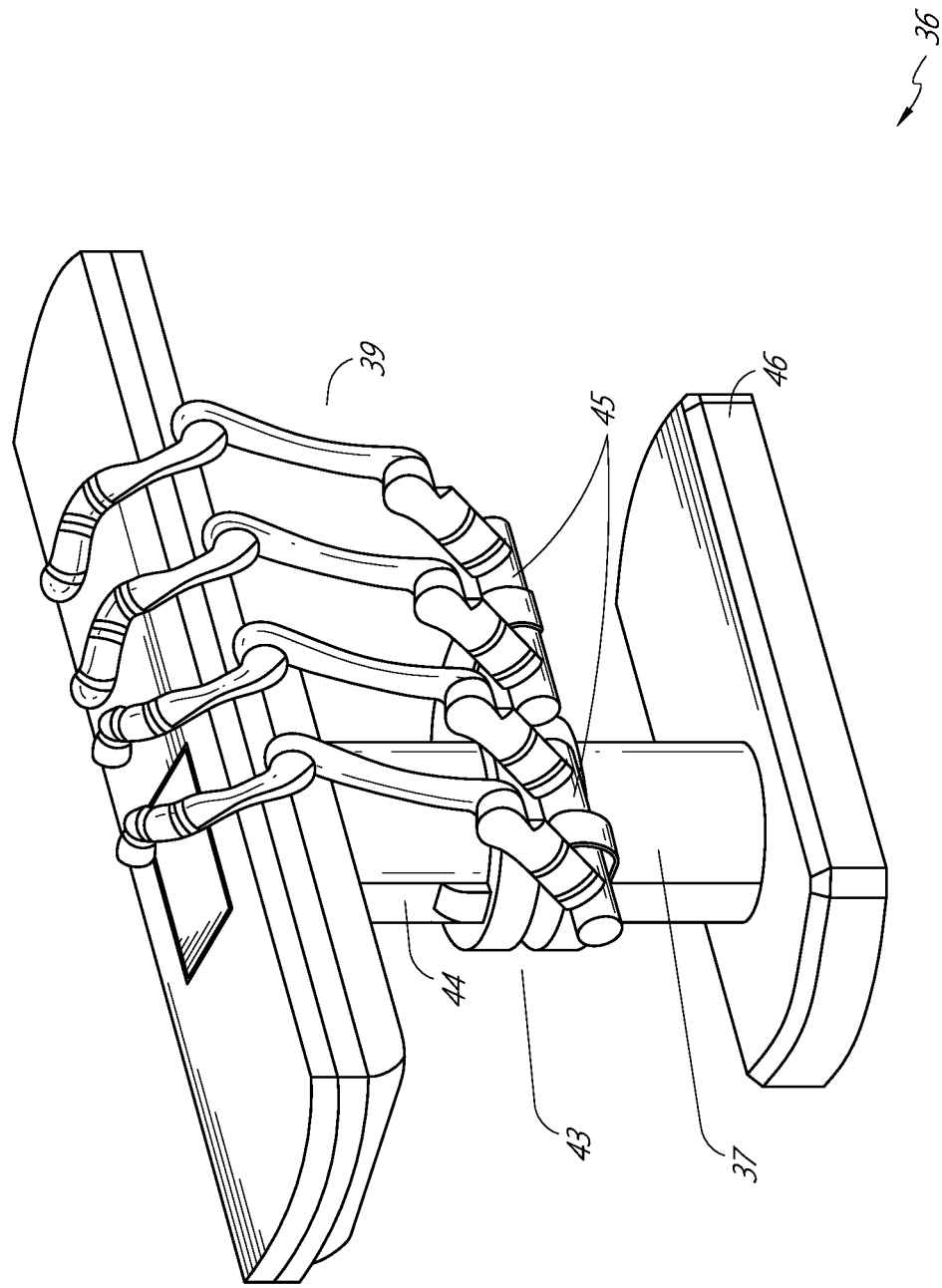
FIG. 6 provides an alternative view of the robotic system of FIG. 5.

FIG. 6 provides an alternative view of the system 36 without the patient and medical instrument for discussion purposes. As shown, the column 37 may include one or more carriages 43 shown as ring-shaped in the system 36, from which the one or more robotic arms 39 may be based. The carriages 43 may translate along a vertical column interface 44 that runs the length of the column 37 to provide different vantage points from which the robotic arms 39 may be positioned to reach the patient. The carriage(s) 43 may rotate around the column 37 using a mechanical motor positioned within the column 37 to allow the robotic arms 39 to have access to multiples sides of the table 38, such as, for example, both sides of the patient. In embodiments with multiple carriages, the carriages may be individually positioned on the column and may translate and/or rotate independent of the other carriages. While carriages 43 need not surround the column 37 or even be circular, the ring-shape as shown facilitates rotation of the carriages 43 around the column 37 while maintaining structural balance. Rotation and translation of the carriages 43 allows the system to align the medical instruments, such as endoscopes and laparoscopes, into different access points on the patient.

Figure 9:
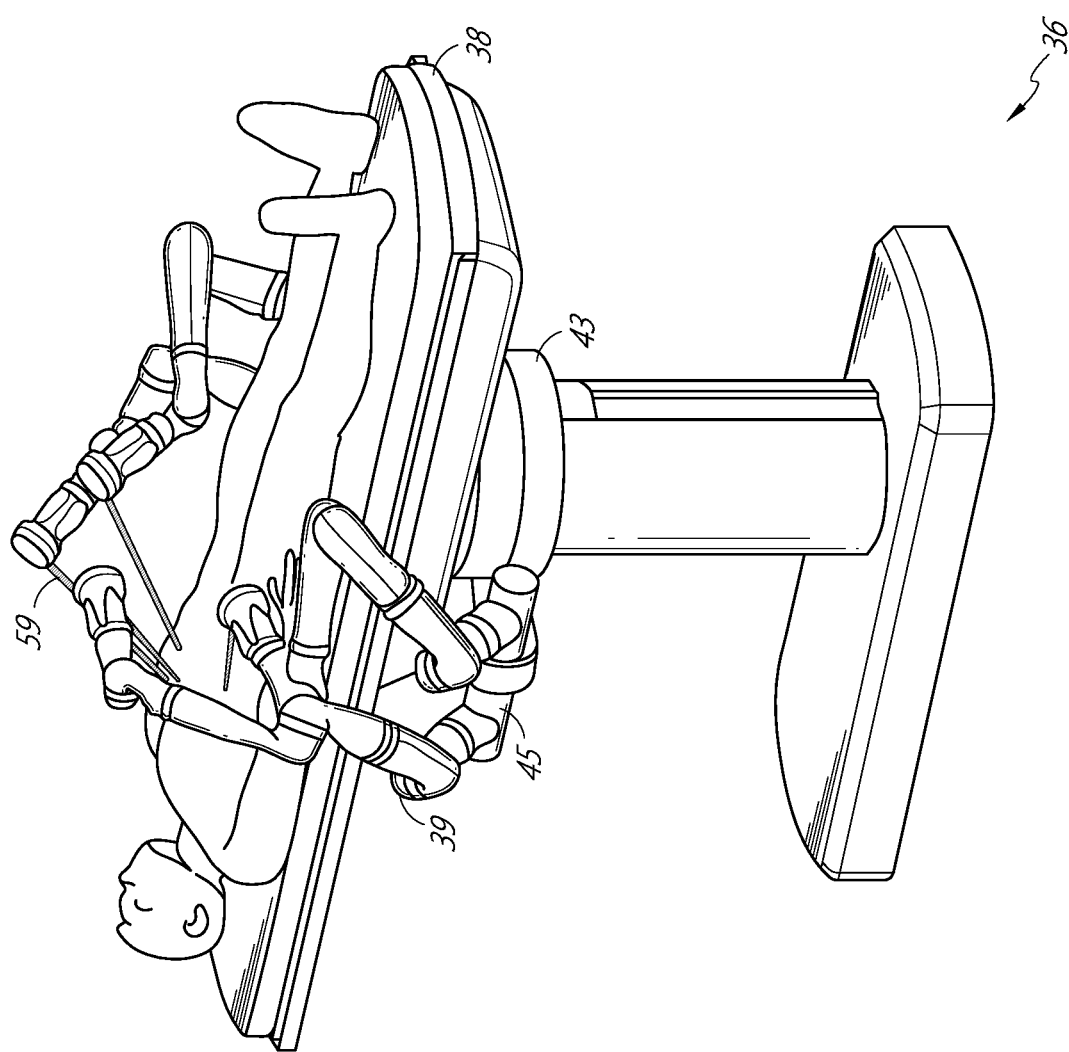
FIG. 9 illustrates an embodiment of a table-based robotic system configured for a laparoscopic procedure.

The arms 39 may be mounted on the carriages through a set of arm mounts 45 comprising a series of joints that may individually rotate and/or telescopically extend to provide additional configurability to the robotic arms 39. Additionally, the arm mounts 45 may be positioned on the carriages 43 such that, when the carriages 43 are appropriately rotated, the arm mounts 45 may be positioned on either the same side of table 38 (as shown in FIG. 6), on opposite sides of table 38 (as shown in FIG. 9), or on adjacent sides of the table 38 (not shown).

The column 37 structurally provides support for the table 38, and a path for vertical translation of the carriages. Internally, the column 37 may be equipped with lead screws for guiding vertical translation of the carriages 43, and motors to mechanize the translation of said carriages based the lead screws. The column 37 may also convey power and control signals to the carriage 43 and robotic arms 39 mounted thereon.

The table base 46 serves a similar function as the cart base 15 in cart 11 shown in FIG. 2, housing heavier components to balance the table/bed 38, the column 37, the carriages 43, and the robotic arms 39. The table base 46 may also incorporate rigid casters to provide stability during procedures. Deployed from the bottom of the table base 46, the casters may extend in opposite directions on both sides of the base 46 and retract when the system 36 needs to be moved.

Continuing with FIG. 6, the system 36 may also include a tower (not shown) that divides the functionality of system 36 between table and tower to reduce the form factor and bulk of the table. As in earlier disclosed embodiments, the tower may be provide a variety of support functionalities to table, such as processing, computing, and control capabilities, power, fluidics, and/or optical and sensor processing. The tower may also be movable to be positioned away from the patient to improve physician access and de-clutter the operating room. Additionally, placing components in the tower allows for more storage space in the table base for potential stowage of the robotic arms. The tower may also include a console that provides both a user interface for user input, such as keyboard and/or pendant, as well as a display screen (or touchscreen) for pre-operative and intra-operative information, such as real-time imaging, navigation, and tracking information.

Figure 7:
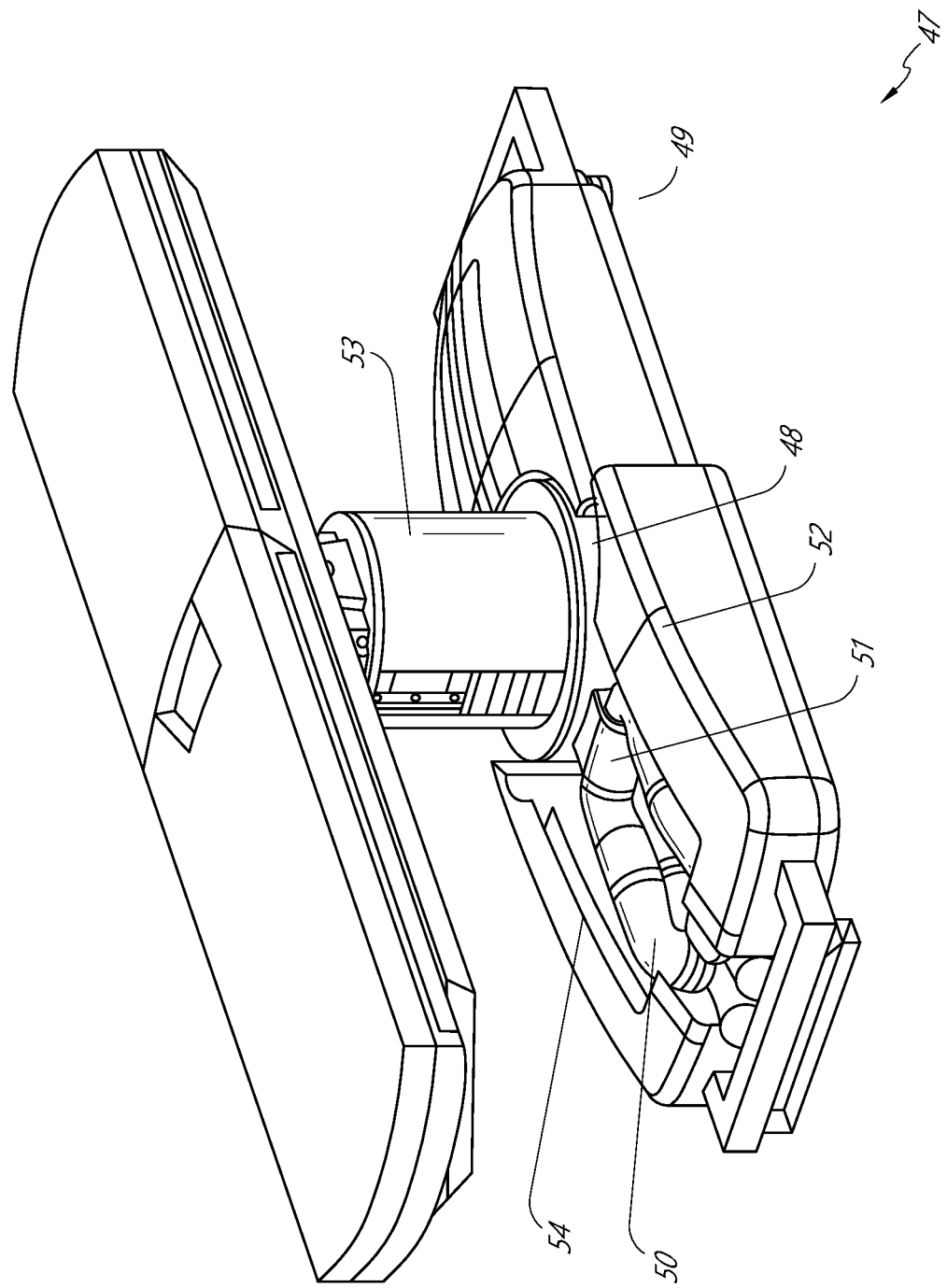
FIG. 7 illustrates an example system configured to stow robotic arm(s).

In some embodiments, a table base may stow and store the robotic arms when not in use. FIG. 7 illustrates a system 47 that stows robotic arms in an embodiment of the table-based system. In system 47, carriages 48 may be vertically translated into base 49 to stow robotic arms 50, arm mounts 51, and the carriages 48 within the base 49. Base covers 52 may be translated and retracted open to deploy the carriages 48, arm mounts 51, and arms 50 around column 53, and closed to stow to protect them when not in use. The base covers 52 may be sealed with a membrane 54 along the edges of its opening to prevent dirt and fluid ingress when closed.

Figure 8:
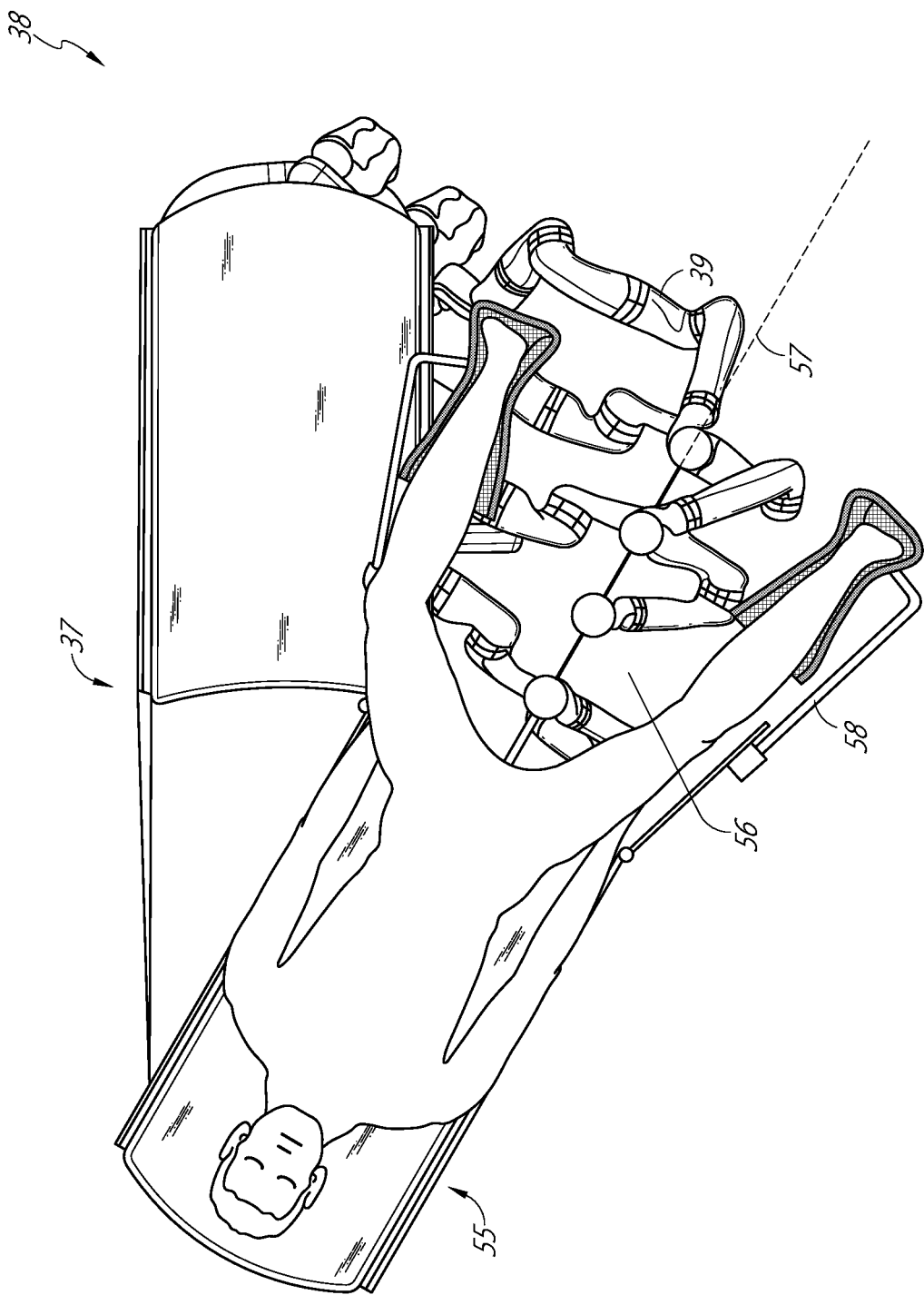
FIG. 8 illustrates an embodiment of a table-based robotic system configured for a ureteroscopy procedure.

FIG. 8 illustrates an embodiment of a robotically-enabled table-based system configured for a ureteroscopy procedure. In ureteroscopy, the table 38 may include a swivel portion 55 for positioning a patient off-angle from the column 37 and table base 46. The swivel portion 55 may rotate or pivot around a pivot point (e.g., located below the patient's head) in order to position the bottom portion of the swivel portion 55 away from the column 37. For example, the pivoting of the swivel portion 55 allows a C-arm (not shown) to be positioned over the patient's lower abdomen without competing for space with the column (not shown) below table 38. By rotating the carriage (not shown) around the column 37, the robotic arms 39 may directly insert a ureteroscope 56 along a virtual rail 57 into the patient's groin area to reach the urethra. In ureteroscopy, stirrups 58 may also be fixed to the swivel portion 55 of the table 38 to support the position of the patient's legs during the procedure and allow clear access to the patient's groin area.

In a laparoscopic procedure, through small incision(s) in the patient's abdominal wall, minimally invasive instruments (elongated in shape to accommodate the size of the one or more incisions) may be inserted into the patient's anatomy. After inflation of the patient's abdominal cavity, the instruments, often referred to as laparoscopes, may be directed to perform surgical tasks, such as grasping, cutting, ablating, suturing, etc. FIG. 9 illustrates an embodiment of a robotically-enabled table-based system configured for a laparoscopic procedure. As shown in FIG. 9, the carriages 43 of the system 36 may be rotated and vertically adjusted to position pairs of the robotic arms 39 on opposite sides of the table 38, such that laparoscopes 59 may be positioned using the arm mounts 45 to be passed through minimal incisions on both sides of the patient to reach his/her abdominal cavity.

Figure 10:
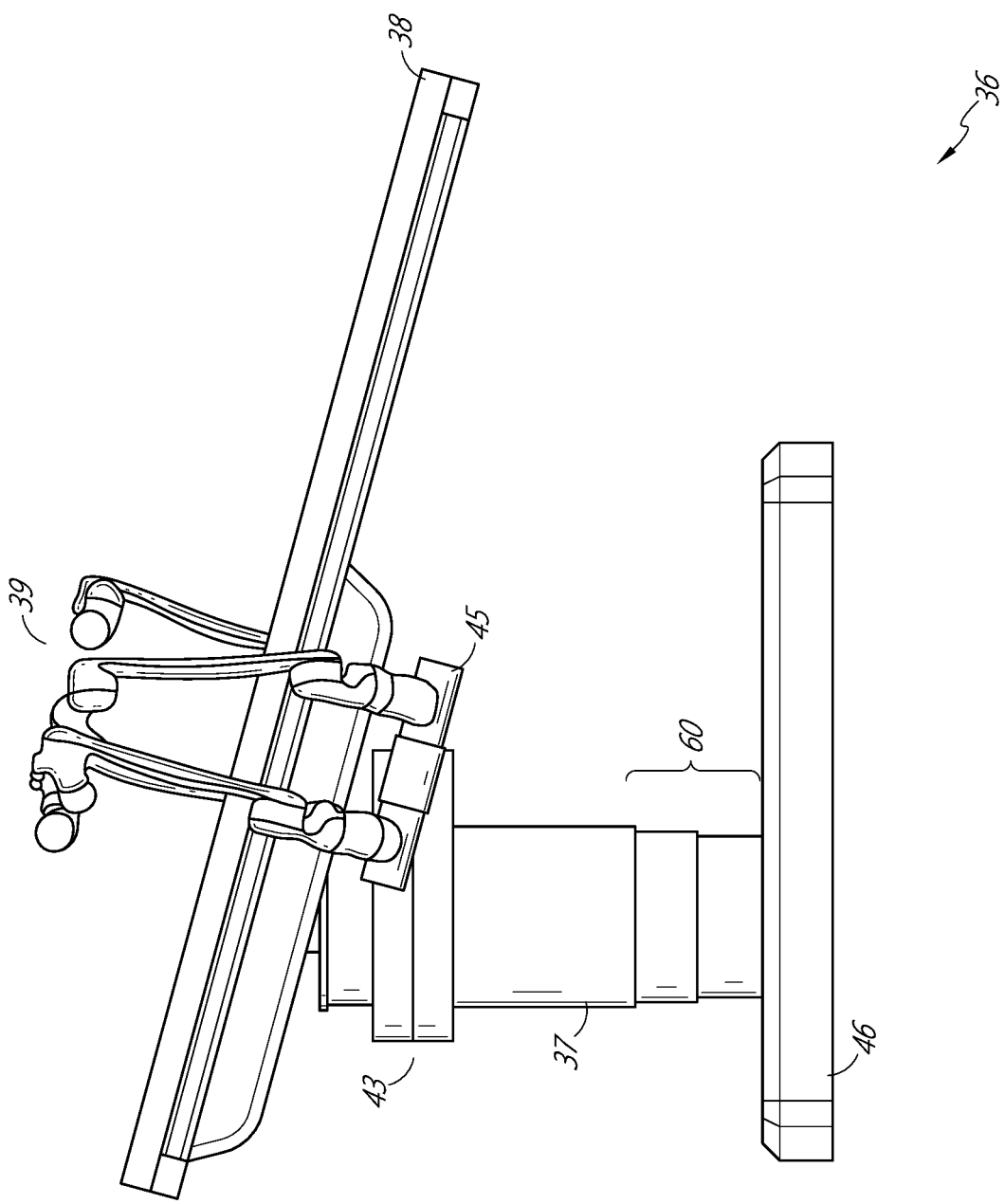
FIG. 10 illustrates an embodiment of the table-based robotic system of FIGS. 5-9 with pitch or tilt adjustment.

To accommodate laparoscopic procedures, the robotically-enabled table system may also tilt the platform to a desired angle. FIG. 10 illustrates an embodiment of the robotically-enabled medical system with pitch or tilt adjustment. As shown in FIG. 10, the system 36 may accommodate tilt of the table 38 to position one portion of the table at a greater distance from the floor than the other. Additionally, the arm mounts 45 may rotate to match the tilt such that the arms 39 maintain the same planar relationship with table 38. To accommodate steeper angles, the column 37 may also include telescoping portions 60 that allow vertical extension of column 37 to keep the table 38 from touching the floor or colliding with base 46.

Figure 11:
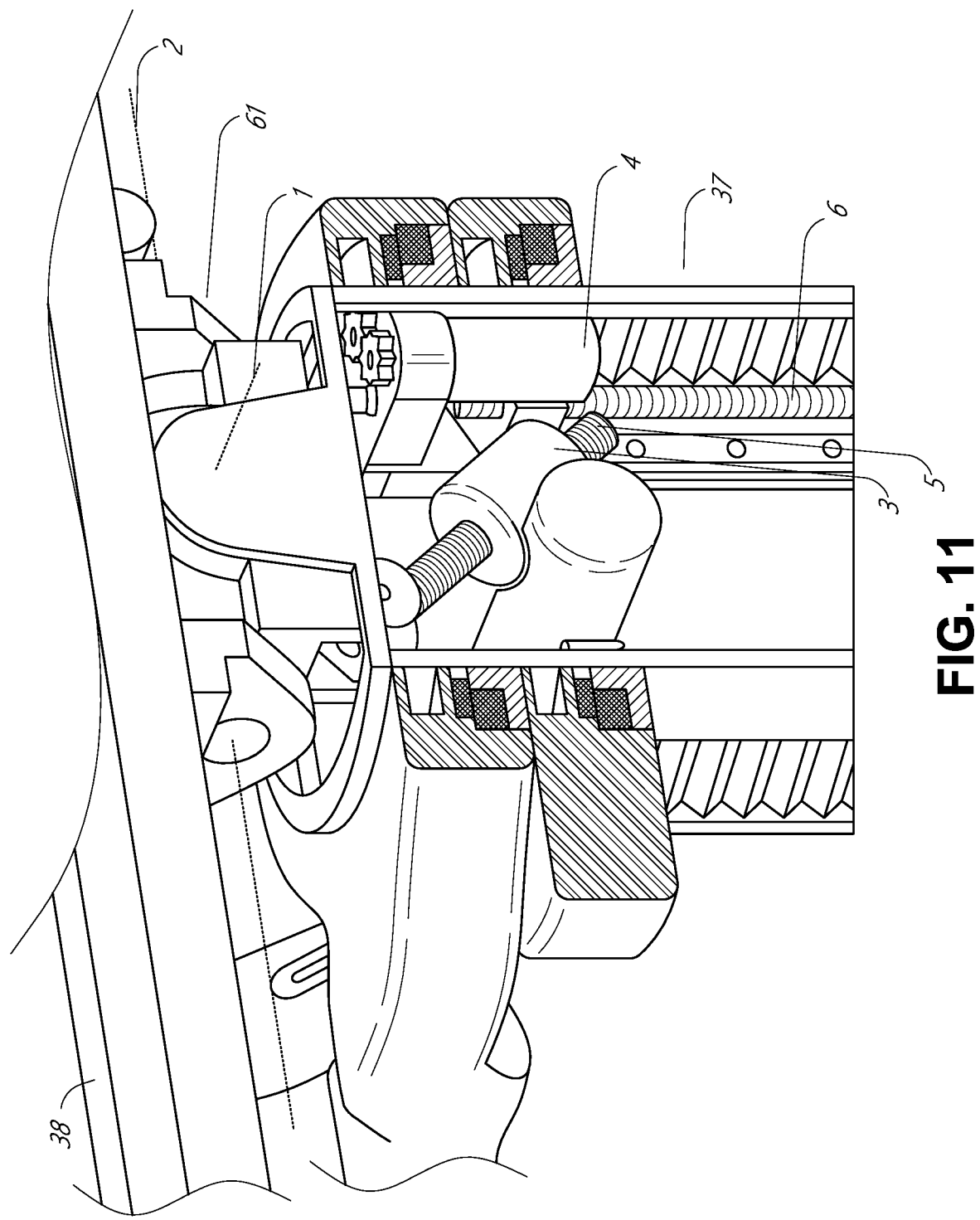
FIG. 11 provides a detailed illustration of the interface between the table and the column of the table-based robotic system of FIGS. 5-10.

FIG. 11 provides a detailed illustration of the interface between the table 38 and the column 37. Pitch rotation mechanism 61 may be configured to alter the pitch angle of the table 38 relative to the column 37 in multiple degrees of freedom. The pitch rotation mechanism 61 may be enabled by the positioning of orthogonal axes 1, 2, at the column-table interface, each axis actuated by a separate motor 3, 4, responsive to an electrical pitch angle command. Rotation along one screw 5 would enable tilt adjustments in one axis 1, while rotation along the other screw 6 would enable tilt adjustments along the other axis 2.

For example, pitch adjustments are particularly useful when trying to position the table in a Trendelenburg position, i.e., position the patient's lower abdomen at a higher position from the floor than the patient's lower abdomen, for lower abdominal surgery. The Trendelenburg position causes the patient's internal organs to slide towards his/her upper abdomen through the force of gravity, clearing out the abdominal cavity for minimally invasive tools to enter and perform lower abdominal surgical procedures, such as laparoscopic prostatectomy.

C. Instrument Driver & Interface.

The end effectors of the system's robotic arms comprise (i) an instrument driver (alternatively referred to as "instrument drive mechanism" or "instrument device manipulator") that incorporate electro-mechanical means for actuating the medical instrument and (ii) a removable or detachable medical instrument which may be devoid of any electro-mechanical components, such as motors. This dichotomy may be driven by the need to sterilize medical instruments used in medical procedures, and the inability to adequately sterilize expensive capital equipment due to their intricate mechanical assemblies and sensitive electronics. Accordingly, the medical instruments may be designed to be detached, removed, and interchanged from the instrument driver (and thus the system) for individual sterilization or disposal by the physician or the physician's staff. In contrast, the instrument drivers need not be changed or sterilized, and may be draped for protection.

Figure 12:
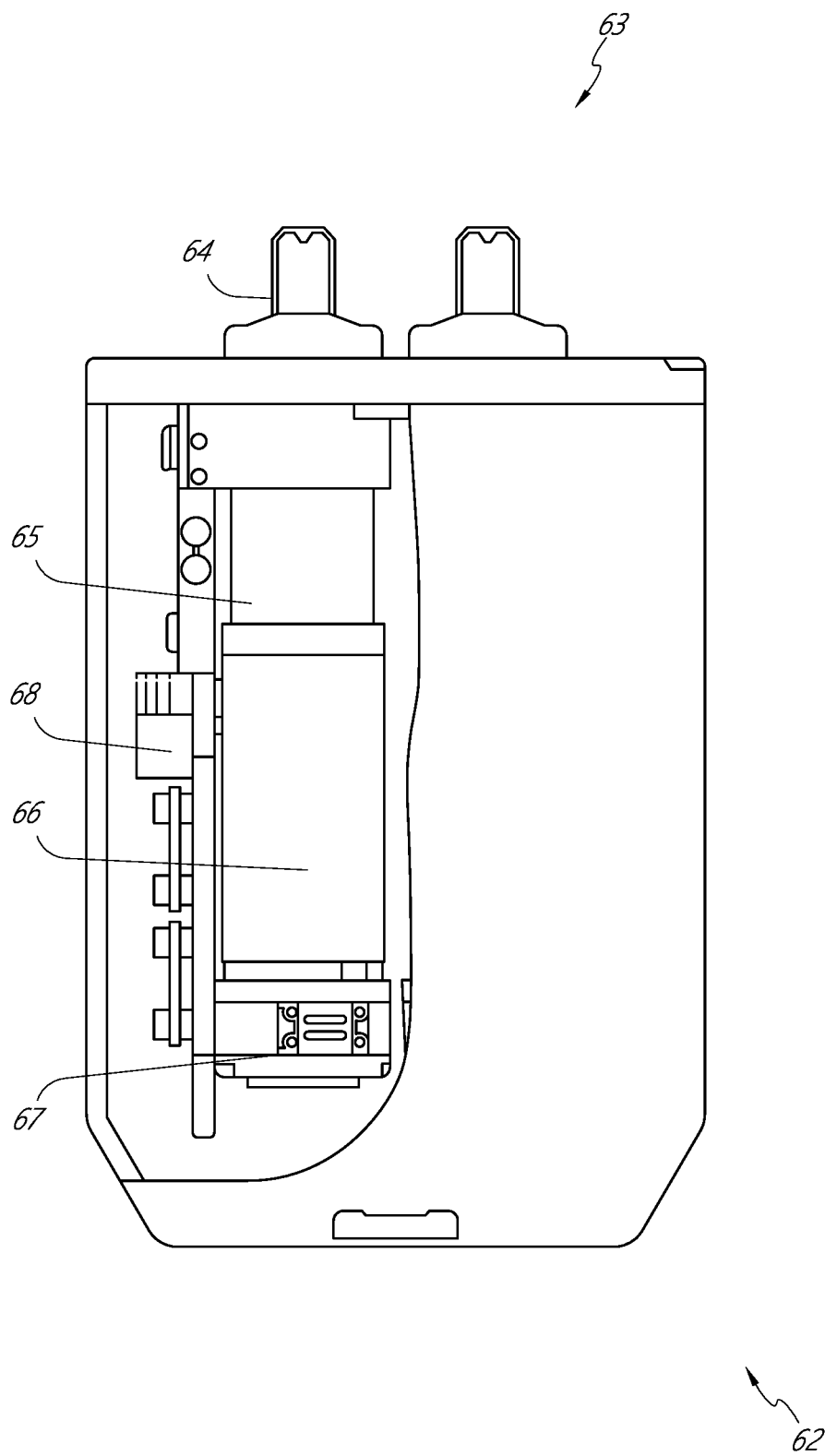
FIG. 12 illustrates an exemplary instrument driver.

FIG. 12 illustrates an example instrument driver. Positioned at the distal end of a robotic arm, instrument driver 62 comprises of one or more drive units 63 arranged with parallel axes to provide controlled torque to a medical instrument via drive shafts 64. Each drive unit 63 comprises an individual drive shaft 64 for interacting with the instrument, a gear head 65 for converting the motor shaft rotation to a desired torque, a motor 66 for generating the drive torque, an encoder 67 to measure the speed of the motor shaft and provide feedback to control circuitry, and control circuitry 68 for receiving control signals and actuating the drive unit. Each drive unit 63 being independent controlled and motorized, the instrument driver 62 may provide multiple (four as shown in FIG. 12) independent drive outputs to the medical instrument. In operation, the control circuitry 68 would receive a control signal, transmit a motor signal to the motor 66, compare the resulting motor speed as measured by the encoder 67 with the desired speed, and modulate the motor signal to generate the desired torque.

For procedures that require a sterile environment, the robotic system may incorporate a drive interface, such as a sterile adapter connected to a sterile drape, that sits between the instrument driver and the medical instrument. The chief purpose of the sterile adapter is to transfer angular motion from the drive shafts of the instrument driver to the drive inputs of the instrument while maintaining physical separation, and thus sterility, between the drive shafts and drive inputs. Accordingly, an example sterile adapter may comprise of a series of rotational inputs and outputs intended to be mated with the drive shafts of the instrument driver and drive inputs on the instrument. Connected to the sterile adapter, the sterile drape, comprised of a thin, flexible material such as transparent or translucent plastic, is designed to cover the capital equipment, such as the instrument driver, robotic arm, and cart (in a cart-based system) or table (in a table-based system). Use of the drape would allow the capital equipment to be positioned proximate to the patient while still being located in an area not requiring sterilization (i.e., non-sterile field). On the other side of the sterile drape, the medical instrument may interface with the patient in an area requiring sterilization (i.e., sterile field).

D. Medical Instrument.

Figure 13:
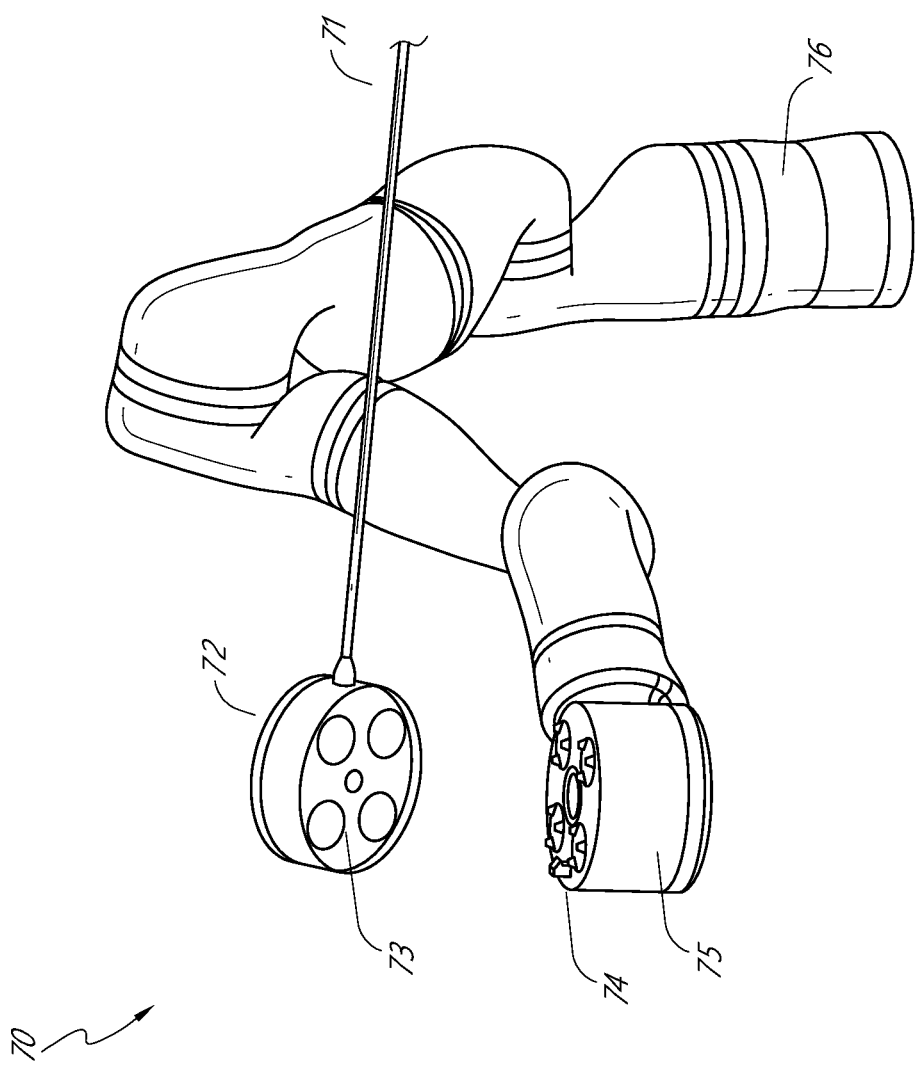
FIG. 13 illustrates an exemplary medical instrument with a paired instrument driver.

FIG. 13 illustrates an example medical instrument with a paired instrument driver. Like other instruments designed for use with a robotic system, medical instrument 70 comprises an elongated shaft 71 (or elongate body) and an instrument base 72. The instrument base 72, also referred to as an "instrument handle" due to its intended design for manual interaction by the physician, may generally comprise rotatable drive inputs 73, e.g., receptacles, pulleys or spools, that are designed to be mated with drive outputs 74 that extend through a drive interface on instrument driver 75 at the distal end of robotic arm 76. When physically connected, latched, and/or coupled, the mated drive inputs 73 of instrument base 72 may share axes of rotation with the drive outputs 74 in the instrument driver 75 to allow the transfer of torque from drive outputs 74 to drive inputs 73. In some embodiments, the drive outputs 74 may comprise splines that are designed to mate with receptacles on the drive inputs 73.

The elongated shaft 71 is designed to be delivered through either an anatomical opening or lumen, e.g., as in endoscopy, or a minimally invasive incision, e.g., as in laparoscopy. The elongated shaft 66 may be either flexible (e.g., having properties similar to an endoscope) or rigid (e.g., having properties similar to a laparoscope) or contain a customized combination of both flexible and rigid portions. When designed for laparoscopy, the distal end of a rigid elongated shaft may be connected to an end effector comprising a jointed wrist formed from a clevis with an axis of rotation and a surgical tool, such as, for example, a grasper or scissors, that may be actuated based on force from the tendons as the drive inputs rotate in response to torque received from the drive outputs 74 of the instrument driver 75. When designed for endoscopy, the distal end of a flexible elongated shaft may include a steerable or controllable bending section that may be articulated and bent based on torque received from the drive outputs 74 of the instrument driver 75.

Torque from the instrument driver 75 is transmitted down the elongated shaft 71 using tendons within the shaft 71. These individual tendons, such as pull wires, may be individually anchored to individual drive inputs 73 within the instrument handle 72. From the instrument handle 72, the tendons are directed down one or more pull lumens within the elongated shaft 71 and anchored at the distal portion of the elongated shaft 71. In laparoscopy, these tendons may be coupled to a distally mounted end effector, such as a wrist, grasper, or scissor. Under such an arrangement, torque exerted on drive inputs 73 would transfer tension to the tendon, thereby causing the end effector to actuate in some way. In laparoscopy, the tendon may cause a joint to rotate about an axis, thereby causing the end effector to move in one direction or another. Alternatively, the tendon may be connected to one or more jaws of a grasper at distal end of the elongated shaft 71, where tension from the tendon cause the grasper to close.

In endoscopy, the tendons may be coupled to a bending or articulating section positioned along the elongated shaft 71 (e.g., at the distal end) via adhesive, control ring, or other mechanical fixation. When fixedly attached to the distal end of a bending section, torque exerted on drive inputs 73 would be transmitted down the tendons, causing the softer, bending section (sometimes referred to as the articulable section or region) to bend or articulate. Along the non-bending sections, it may be advantageous to spiral or helix the individual pull lumens that direct the individual tendons along (or inside) the walls of the endoscope shaft to balance the radial forces that result from tension in the pull wires. The angle of the spiraling and/or spacing there between may be altered or engineered for specific purposes, wherein tighter spiraling exhibits lesser shaft compression under load forces, while lower amounts of spiraling results in greater shaft compression under load forces, but also exhibits limits bending. On the other end of the spectrum, the pull lumens may be directed parallel to the longitudinal axis of the elongated shaft 71 to allow for controlled articulation in the desired bending or articulable sections.

In endoscopy, the elongated shaft 71 houses a number of components to assist with the robotic procedure. The shaft may comprise of a working channel for deploying surgical tools, irrigation, and/or aspiration to the operative region at the distal end of the shaft 71. The shaft 71 may also accommodate wires and/or optical fibers to transfer signals to/from an optical assembly at the distal tip, which may include of an optical camera. The shaft 71 may also accommodate optical fibers to carry light from proximally-located light sources, such as light emitting diodes, to the distal end of the shaft.

At the distal end of the instrument 70, the distal tip may also comprise the opening of a working channel for delivering tools for diagnostic and/or therapy, irrigation, and aspiration to an operative site. The distal tip may also include a port for a camera, such as a fiberscope or a digital camera, to capture images of an internal anatomical space. Relatedly, the distal tip may also include ports for light sources for illuminating the anatomical space when using the camera.

In the example of FIG. 13, the drive shaft axes, and thus the drive input axes, are orthogonal to the axis of the elongated shaft. This arrangement, however, complicates roll capabilities for the elongated shaft 71. Rolling the elongated shaft 71 along its axis while keeping the drive inputs 73 static results in undesirable tangling of the tendons as they extend off the drive inputs 73 and enter pull lumens within the elongate shaft 71. The resulting entanglement of such tendons may disrupt any control algorithms intended to predict movement of the flexible elongate shaft during an endoscopic procedure.

Figure 14:
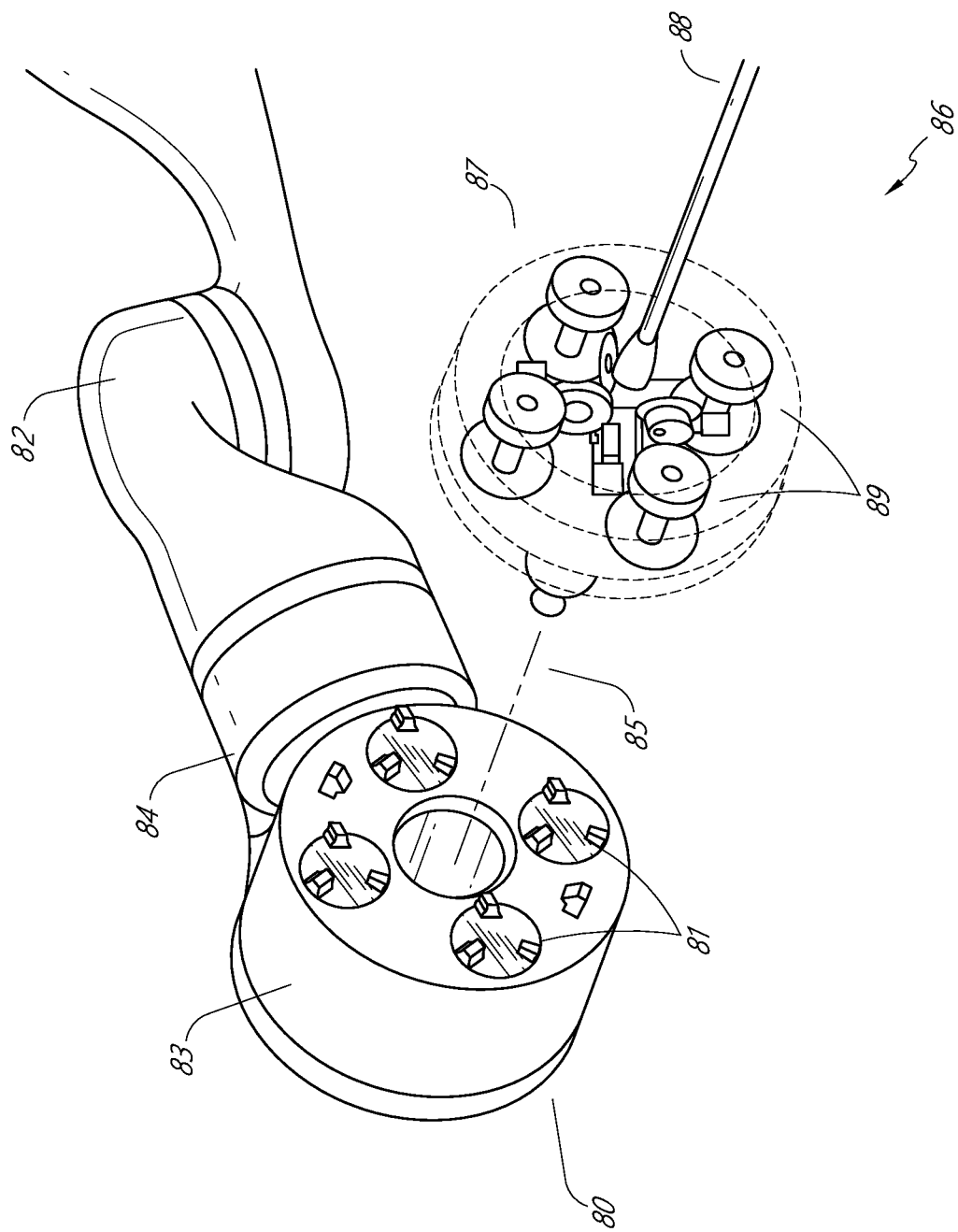
FIG. 14 illustrates an alternative design for an instrument driver and instrument where the axes of the drive units are parallel to the axis of the elongated shaft of the instrument.

FIG. 14 illustrates an alternative design for an instrument driver and instrument where the axes of the drive units are parallel to the axis of the elongated shaft of the instrument. As shown, a circular instrument driver 80 comprises four drive units with their drive outputs 81 aligned in parallel at the end of a robotic arm 82. The drive units, and their respective drive outputs 81, are housed in a rotational assembly 83 of the instrument driver 80 that is driven by one of the drive units within the assembly 83. In response to torque provided by the rotational drive unit, the rotational assembly 83 rotates along a circular bearing that connects the rotational assembly 83 to the non-rotational portion 84 of the instrument driver. Power and controls signals may be communicated from the non-rotational portion 84 of the instrument driver 80 to the rotational assembly 83 through electrical contacts may be maintained through rotation by a brushed slip ring connection (not shown). In other embodiments, the rotational assembly 83 may be responsive to a separate drive unit that is integrated into the non-rotatable portion 84, and thus not in parallel to the other drive units. The rotational mechanism 83 allows the instrument driver 80 to rotate the drive units, and their respective drive outputs 81, as a single unit around an instrument driver axis 85.

Like earlier disclosed embodiments, an instrument 86 may comprise of an elongated shaft portion 88 and an instrument base 87 (shown with a transparent external skin for discussion purposes) comprising a plurality of drive inputs 89 (such as receptacles, pulleys, and spools) that are configured to receive the drive outputs 81 in the instrument driver 80. Unlike prior disclosed embodiments, instrument shaft 88 extends from the center of instrument base 87 with an axis substantially parallel to the axes of the drive inputs 89, rather than orthogonal as in the design of FIG. 13.

When coupled to the rotational assembly 83 of the instrument driver 80, the medical instrument 86, comprising instrument base 87 and instrument shaft 88, rotates in combination with the rotational assembly 83 about the instrument driver axis 85. Since the instrument shaft 88 is positioned at the center of instrument base 87, the instrument shaft 88 is coaxial with instrument driver axis 85 when attached. Thus, rotation of the rotational assembly 83 causes the instrument shaft 88 to rotate about its own longitudinal axis. Moreover, as the instrument base 87 rotates with the instrument shaft 88, any tendons connected to the drive inputs 89 in the instrument base 87 are not tangled during rotation. Accordingly, the parallelism of the axes of the drive outputs 81, drive inputs 89, and instrument shaft 88 allows for the shaft rotation without tangling any control tendons.

E. Navigation and Control.

Traditional endoscopy may involve the use of fluoroscopy (e.g., as may be delivered through a C-arm) and other forms of radiation-based imaging modalities to provide endoluminal guidance to an operator physician. In contrast, the robotic systems contemplated by this disclosure can provide for non-radiation-based navigational and localization means to reduce physician exposure to radiation and reduce the amount of equipment within the operating room. As used herein, the term "localization" may refer to determining and/or monitoring the position of objects in a reference coordinate system. Technologies such as pre-operative mapping, computer vision, real-time EM tracking, and robot command data may be used individually or in combination to achieve a radiation-free operating environment. In other cases, where radiation-based imaging modalities are still used, the pre-operative mapping, computer vision, real-time EM tracking, and robot command data may be used individually or in combination to improve upon the information obtained solely through radiation-based imaging modalities.

Figure 15:
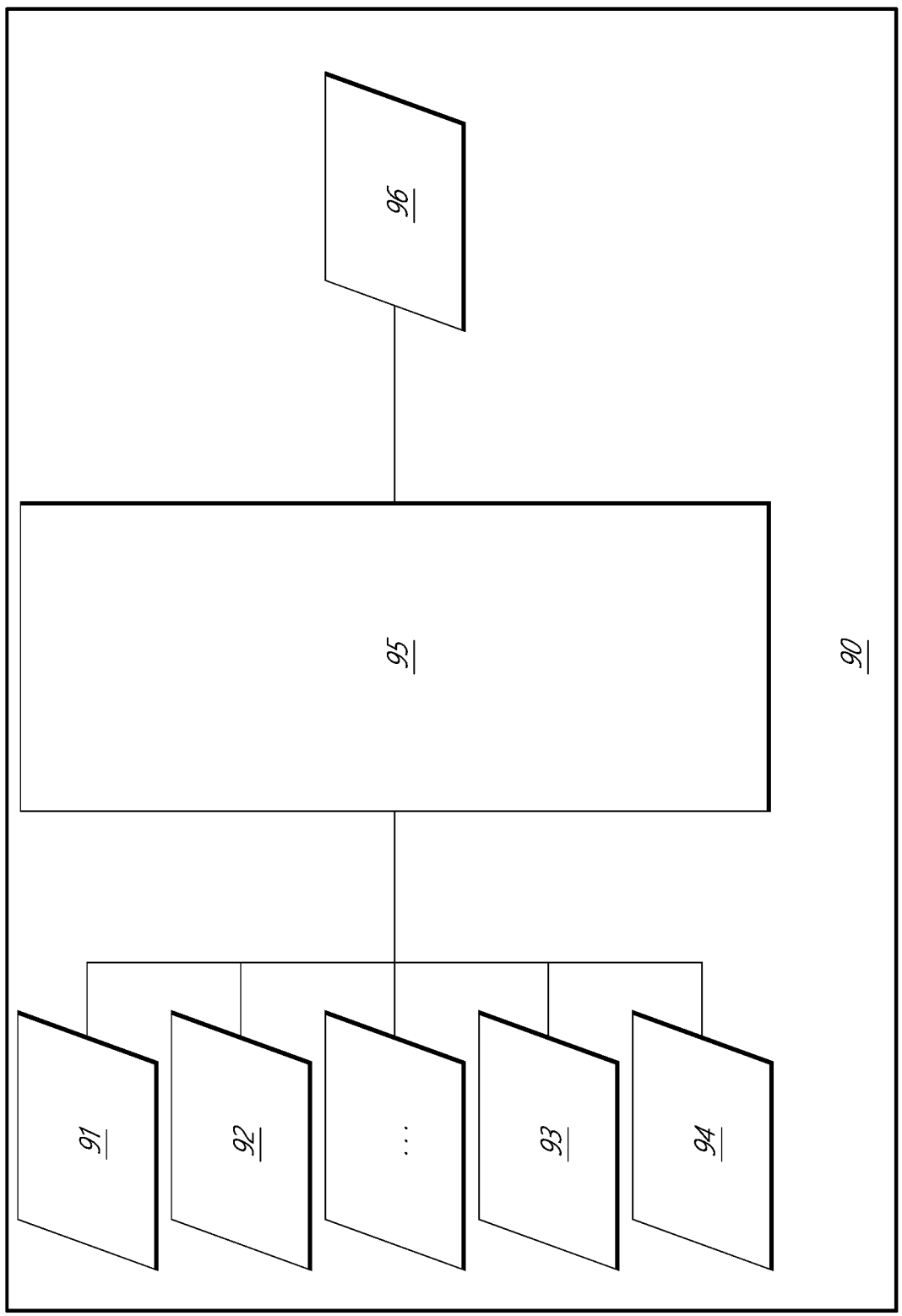
FIG. 15 depicts a block diagram illustrating a localization system that estimates a location of one or more elements of the robotic systems of FIGS. 1-10, such as the location of the instrument of FIGS. 13-14, in accordance to an example embodiment.

FIG. 15 is a block diagram illustrating a localization system 90 that estimates a location of one or more elements of the robotic system, such as the location of the instrument, in accordance to an example embodiment. The localization system 90 may be a set of one or more computer devices configured to execute one or more instructions. The computer devices may be embodied by a processor (or processors) and computer-readable memory in one or more components discussed above. By way of example and not limitation, the computer devices may be in the tower 30 shown in FIG. 1, the cart shown in FIGS. 1-4, the beds shown in FIGS. 5-10, etc.

As shown in FIG. 15, the localization system 90 may include a localization module 95 that processes input data 91-94 to generate location data 96 for the distal tip of a medical instrument. The location data 96 may be data or logic that represents a location and/or orientation of the distal end of the instrument relative to a frame of reference. The frame of reference can be a frame of reference relative to the anatomy of the patient or to a known object, such as an EM field generator (see discussion below for the EM field generator).

The various input data 91-94 are now described in greater detail. Preoperative mapping may be used by the localization module 95 to generate model data 91. Pre-operative mapping may be accomplished through the use of the collection of low dose CT scans. Pre-operative CT scans generate two-dimensional images, each representing a "slice" of a cutaway view of the patient's internal anatomy. When analyzed in the aggregate, image-based models for anatomical cavities, spaces and structures of the patient's anatomy, such as a patient lung network, may be generated. Techniques such as center-line geometry may be determined and approximated from the CT images to develop a three-dimensional volume of the patient's anatomy, referred to as preoperative model data 91. The use of center-line geometry is discussed in U.S. patent application Ser. No. 14/523,760, the contents of which are herein incorporated in its entirety. Network topological models may also be derived from the CT-images, and are particularly appropriate for bronchoscopy.

In some embodiments, the instrument may be equipped with a camera to provide vision data (or image data) 92 to the localization module 95. The localization module 95 may process the vision data to enable one or more vision-based location tracking. For example, the preoperative model data may be used in conjunction with the vision data 92 to enable computer vision-based tracking of the medical instrument (e.g., an endoscope or an instrument advance through a working channel of the endoscope). For example, using the preoperative model data 91, the robotic system may generate a library of expected endoscopic images from the model based on the expected path of travel of the endoscope, each image linked to a location within the model. Intra-operatively, this library may be referenced by the robotic system in order to compare real-time images captured at the camera (e.g., a camera at a distal end of the endoscope) to those in the image library to assist localization.

Other computer vision-based tracking techniques use feature tracking to determine motion of the camera, and thus the endoscope. Some feature of the localization module 95 may identify circular geometries in the preoperative model data 91 that correspond to anatomical lumens and track the change of those geometries to determine which anatomical lumen was selected, as well as the relative rotational and/or translational motion of the camera. Use of a topological map may further enhance vision-based algorithms or techniques.

Optical flow, another computer vision-based technique, may analyze the displacement and translation of image pixels in a video sequence in the vision data 92 to infer camera movement. Examples of optical flow techniques may include motion detection, object segmentation calculations, luminance, motion compensated encoding, stereo disparity measurement, etc. Through the comparison of multiple frames over multiple iterations, movement and location of the camera (and thus the endoscope) may be determined.

The localization module 95 may use real-time EM tracking and EM data 93 to generate a real-time location of the endoscope in a global coordinate system that may be registered to the patient's anatomy, represented by the preoperative model. In EM tracking, an EM sensor (or tracker) comprising of one or more sensor coils embedded in one or more locations and orientations in a medical instrument (e.g., an endoscopic tool) measures the variation in the EM field created by one or more static EM field generators positioned at a known location. The location information detected by the EM sensors is stored as the EM data 93. The EM field generator (or transmitter), may be placed close to the patient to create a low intensity magnetic field that the embedded sensor may detect. The magnetic field induces small currents in the sensor coils of the EM sensor, which may be analyzed to determine the distance and angle between the EM sensor and the EM field generator. These distances and orientations may be intra-operatively "registered" to the patient anatomy (e.g., the preoperative model) in order to determine the geometric transformation that aligns a single location in the coordinate system with a position in the pre-operative model of the patient's anatomy. Once registered, an embedded EM tracker in one or more positions of the medical instrument (e.g., the distal tip of an endoscope) may provide real-time indications of the progression of the medical instrument through the patient's anatomy.

Robotic command and kinematics data 94 may also be used by the localization module 95 to provide location data 96 for the robotic system. Device pitch and yaw resulting from articulation commands may be determined during pre-operative calibration. Intra-operatively, these calibration measurements may be used in combination with known insertion depth information to estimate the position of the instrument. Alternatively, these calculations may be analyzed in combination with EM, vision, and/or topological modeling to estimate the position of the medical instrument within the network.

As FIG. 15 shows, a number of other input data can be used by the localization module 95. For example, although not shown in FIG. 15, an instrument utilizing shape-sensing fiber can provide shape data that the localization module 95 can use to determine the location and shape of the instrument.

The localization module 95 may use the input data 91-94 in combination(s). In some cases, such a combination may use a probabilistic approach where the localization module 95 assigns a confidence weight to the location determined from each of the input data 91-94. Thus, where the EM data may not be reliable (as may be the case where there is EM interference) the confidence of the location determined by the EM data 93 can be decrease and the localization module 95 may rely more heavily on the vision data 92 and/or the robotic command and kinematics data 94.

As discussed above, the robotic systems discussed herein may be designed to incorporate a combination of one or more of the technologies above. The robotic system's computer-based control system, based in the tower, bed and/or cart, may store computer program instructions, for example, within a non-transitory computer-readable storage medium such as a persistent magnetic storage drive, solid state drive, or the like, that, upon execution, cause the system to receive and analyze sensor data and user commands, generate control signals throughout the system, and display the navigational and localization data, such as the position of the instrument within the global coordinate system, anatomical map, etc.

2. Electromagnetic (EM) Distortion—Navigation and Localization

Figure 16:
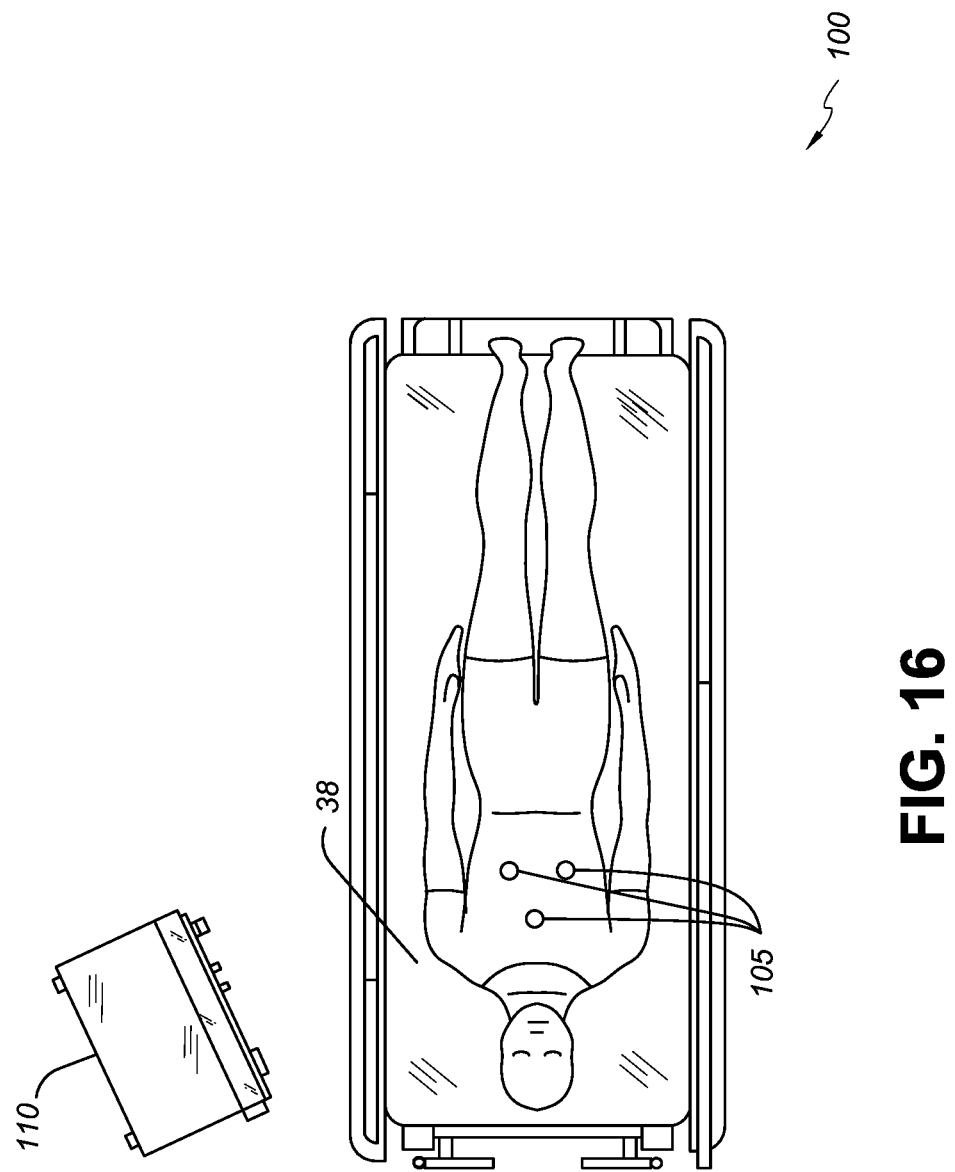
FIG. 16 illustrates an example operating environment implementing one or more aspects of the disclosed navigation systems and techniques.

As discussed above, EM data may be used by embodiments discussed herein for navigation and localization of a surgical instrument (e.g. a steerable instrument). EM data may be generated by one or more EM sensors located within the medical instrument and/or one or more EM patch sensors placed on a patient. FIG. 16 illustrates an example operating environment 100 implementing one or more aspects of the disclosed navigation systems and techniques. The operating environment 100 includes a table 38 supporting a patient, EM sensors 105 (also referred to as "EM patch sensor" so as to be distinguished from EM instrument sensors located on a medical instrument as discussed below), and an EM field generator 110. Certain additional devices/elements may also be included, but have not been illustrated in FIG. 16. For example, the environment 100 may also include: a robotic system configured to guide movement of medical instrument, a command center for controlling operations of the surgical robotic system, and an EM controller. The EM controller may be electrically connected to EM patch sensors 105 to receive EM sensor signals therefrom. The EM controller may further be connected to the EM field generator 110 to provide control signals thereto for generating the EM field. However, in certain embodiments, the EM controller may be partially or completely incorporated into one or more of the other processing device of the system, including the EM field generator 110, the cart 11 (see FIG. 1), and/or the tower 30 (see FIG. 1).

When included, the EM controller may control EM field generator 110 to produce a varying EM field. The EM field may be time-varying and/or spatially varying, depending upon the embodiment. The EM field generator 110 may be located on a cart, similar to the cart 11 illustrated in FIG. 2, or may be attached to a rail of the table 38 via one or more supporting columns. In other embodiments, an EM field generator 110 may be mounted on a robotic arm, for example similar to those shown in surgical robotic system 10 of FIG. 1, which can offer flexible setup options around the patient.

The EM field generator 110 may have an associated working volume in which the EM patch sensors 105 may be placed when in use. For example, the EM sensor signals produced by the EM patch sensors 105 may be sufficiently reliable for use in EM field detection (e.g., EM distortion detection) when they are positioned within the working volume.

Figure 18:
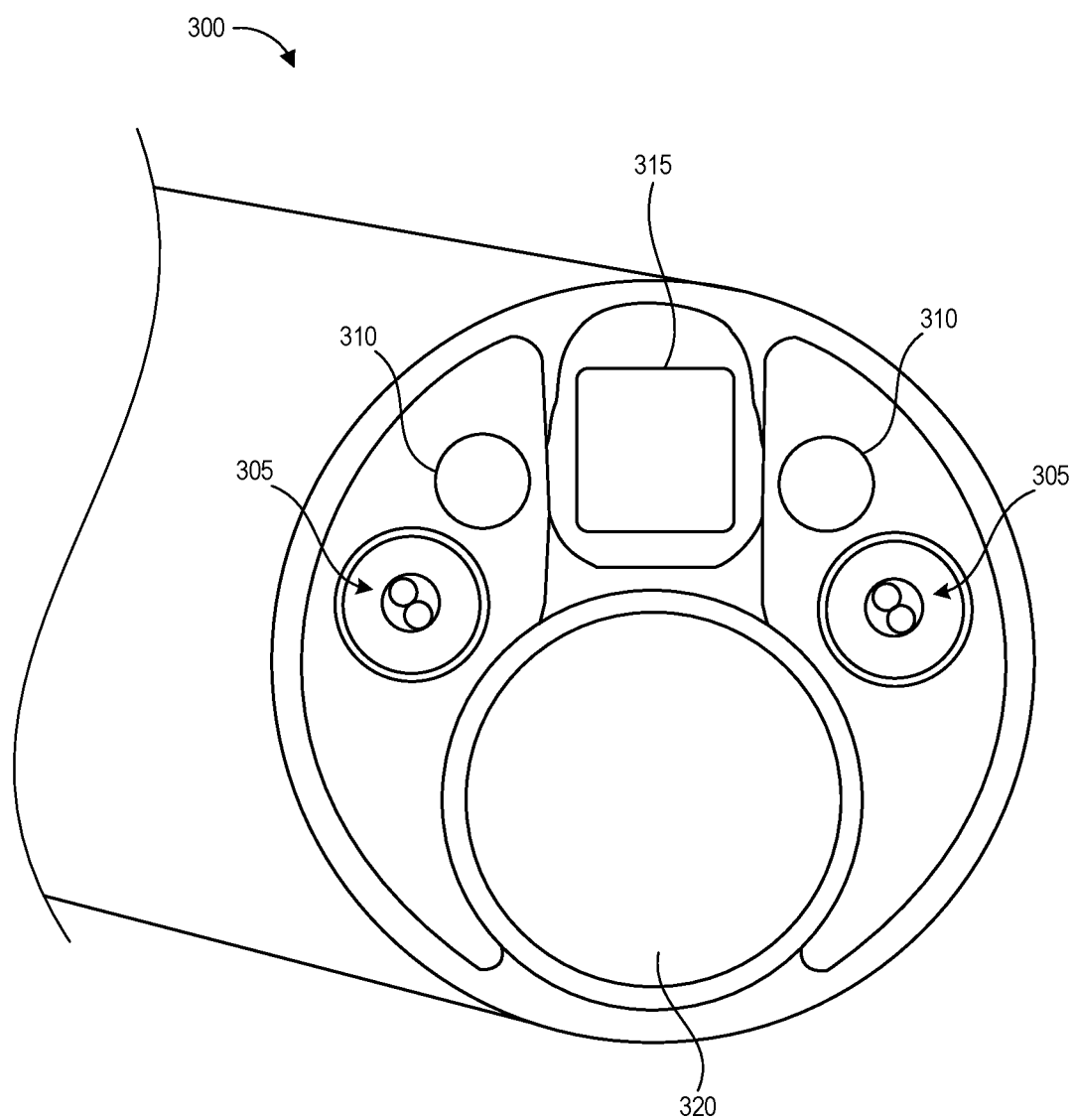
FIG. 18 illustrates the distal end of an example endoscope having imaging and EM sensing capabilities as described herein.

An EM spatial measurement system may determine the location of objects within the EM field that are embedded or provided with EM sensor coils, for example EM patch sensors 105 or EM instrument sensors 305 (as shown in FIG. 18 and discussed below). When an EM sensor is placed inside a controlled, varying EM field as described herein, voltages are induced in sensor coil(s) included in the EM sensor. These induced voltages can be used by the EM spatial measurement system to calculate the position and orientation of the EM sensor and thus the object having the EM sensor. As the EM fields are of a low field strength and can safely pass through human tissue, location measurement of an object is possible without the line-of-sight constraints of an optical spatial measurement system.

The EM field may be defined relative to a coordinate frame of the EM field generator 110, and a coordinate frame of a 3D model of the luminal network can be mapped to the coordinate frame of the EM field. However, the EM field may be affected by one or more sources of EM distortion in the environment 100. For example, the presence of a ferromagnetic material within working volume of the EM field generator 110 or within the environment 100 may distort the EM field. This effect may depend on the distance between the ferromagnetic material and the working volume of the EM field as well as on the properties of the ferromagnetic material. However, other materials may also affect the EM field, such as paramagnetic materials, etc. Examples of common sources of EM distortion which may be present in the environment 100 include: fluoroscopes, tools, instruments, beds, and tables.

The effects of an EM field distortion source may be tolerable for certain applications when the EM field distortion source is stationary. That is, the EM field may be substantially static when a stationary EM distortion source is present. However, the movement of an EM distortion source may cause changes in the EM sensor signals that would otherwise be interpreted as movement of the EM sensors. In other circumstances, a change in electrical current flow within the source of the EM distortion can also cause EM distortion that would otherwise be interpreted as movement of the EM sensors. Thus, it is desirable to detect EM field distortion to prevent such distortions from being incorrectly interpreted by the EM spatial measurement system as movement of the EM sensors.

As shown in FIG. 16, a number of EM patch sensors 105 may be placed on the body of the patient (e.g., in the region of a luminal network 140). These EM patch sensors 105 may be used to track displacement of the patient's body caused by respiration as well as to track EM field distortion. A number of different EM patch sensors 105 may be spaced apart on the body surface in order to track the different displacements at these locations. For example, the periphery of the lungs may exhibit greater motion due to respiration than the central airways, and providing a number of EM patch sensors 105 as shown can enable more precise analysis of these motion effects. To illustrate, the distal end of an endoscope may travel through different regions of the luminal network 140 and thus experience varying levels of displacement due to patient respiration as it travels through these different regions.

Additionally, as the number of EM patch sensors 105 increases, the robustness of EM field distortion detection may be increased since more complex analysis of the movement of the EM patch sensors 105 may be performed using the additional EM sensor signals produced. As will be described in greater detail below, the EM sensor signals received from an EM patch sensor 105 may be used to determine the position and orientation of the EM patch sensor 105 with respect to the EM field generator 110. In certain embodiments, an EM patch sensor 105 may provide 5 degrees-of-freedom (DoF) of movement data (e.g., 3 positional DoF and 2 angular DoF) or 6 DoF data (e.g., 3 positional DoF and 3 angular DoF). When only a single EM patch sensor 105 is present, it may be difficult to distinguish EM distortion from movement of the EM patch sensor 105. However, with additional EM patch sensors 105, additional metrics may be calculated, such as the relative distance between the EM patch sensors 105. Since the relative distance between EM patch sensors 105 is substantially fixed (e.g., the EM patch sensors 105 are fixed to locations on the patient's body and the relative distance will only change due to respiration or removal from the patient), changes in the relative distance that are inconsistent with the patient's respiration may be identified as due to EM distortion.

Figure 17:
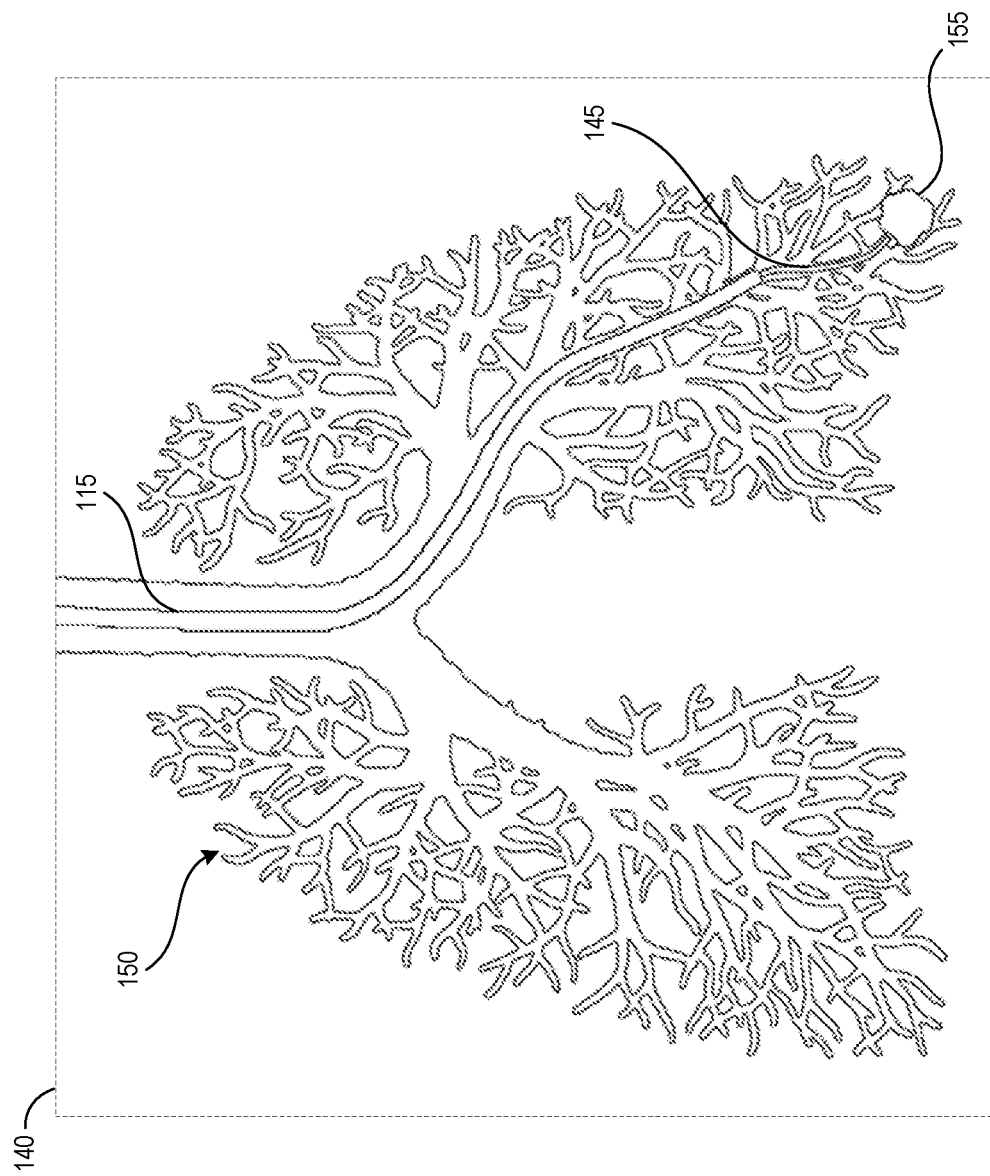
FIG. 17 illustrates an example luminal network 140 that can be navigated in the operating environment of FIG. 16.

FIG. 17 illustrates an example luminal network 140 that can be navigated in the operating environment 100 of FIG. 16. The luminal network 140 includes the branched structure of the airways 150 of the patient and a nodule 155 that can be accessed as described herein for diagnosis and/or treatment. As illustrated, the nodule 155 is located at the periphery of the airways 150. The endoscope 115 has a first diameter and thus its distal end is not able to be positioned through the smaller-diameter airways around the nodule 155. Accordingly, a steerable catheter 145 extends from the working channel of the endoscope 115 the remaining distance to the nodule 155. The steerable catheter 145 may have a lumen through which instruments, for example biopsy needles, cytology brushes, and/or tissue sampling forceps, can be passed to the target tissue site of nodule 155. In such implementations, both the distal end of the endoscope 115 and the distal end of the steerable catheter 145 can be provided with EM instrument sensors for tracking their position within the airways 150. In other embodiments, the overall diameter of the endoscope 115 may be small enough to reach the periphery without the steerable catheter 145, or may be small enough to get close to the periphery (e.g., within 2.5-3 cm) to deploy medical instruments through a non-steerable catheter. The medical instruments deployed through the endoscope 115 may be equipped with EM instrument sensors, and the position filtering and safety-mode navigation techniques described below can be applied to such medical instruments.

In some embodiments, a 2D display of a 3D luminal network model as described herein, or a cross-section of a 3D model, can resemble FIG. 17. Navigation safety zones and/or navigation path information can be overlaid onto such a representation.

FIG. 18 illustrates the distal end 300 of an example endoscope having imaging and EM sensing capabilities as described herein, for example the endoscope 13 of FIG. 1. However, aspects of this disclosure may relate to the use of other steerable instruments, such as the ureteroscope 32 of FIG. 3, laparoscope 59 of FIG. 9, etc. In FIG. 18, the distal end 300 of the endoscope includes an imaging device 315, illumination sources 310, and ends of EM sensor coils 305, which form an EM instrument sensor. The distal end 300 further includes an opening to a working channel 320 of the endoscope through which surgical instruments, such as biopsy needles, cytology brushes, and forceps, may be inserted along the endoscope shaft, allowing access to the area near the endoscope tip.

EM coils 305 located on the distal end 300 may be used with an EM tracking system to detect the position and orientation of the distal end 300 of the endoscope while it is disposed within an anatomical system. In some embodiments, the coils 305 may be angled to provide sensitivity to EM fields along different axes, giving the disclosed navigational systems the ability to measure a full 6 DoF: 3 positional DoF and 3 angular DoF. In other embodiments, only a single coil may be disposed on or within the distal end 300 with its axis oriented along the endoscope shaft of the endoscope. Due to the rotational symmetry of such a system, it is insensitive to roll about its axis, so only 5 degrees of freedom may be detected in such an implementation.

A. Local Distortion.

An example of the detection of local EM distortion will be described with reference to an embodiment of this disclosure that includes the navigation and localization of an endoscope. However, aspects of this disclosure also relate to the detection of EM distortion with respect to the navigation and localization of any type of surgical instrument, e.g., a gastroscope, laparoscope, etc. As used herein, local EM distortion generally refers to EM distortion caused due to a distortion source that is located adjacent to or within an instrument.

One example of a local EM distortion source is a radial endobronchial ultrasound (REBUS) probe. A REBUS probe may be used to provide a 360° image of the parabronchial structures and enable visualization of structures from the probe. A REBUS probe may include components which can cause local EM distortion that may affect an EM sensor provided on an instrument. For example, a REBUS probe may include a transducer in a conductive head, the transducer being bonded to a torque coil. The REBUS probe may also include a fluid-filled closed catheter. Each of these components may cause distortions to the EM field near the REBUS probe, which when the REBUS probe is moved through a working channel in the instrument, may cause local EM distortion with the EM sensor on the instrument.

As discussed above, surgical instruments such as biopsy needles, cytology brushes, and forceps, may be inserted and passed through the working channel 320 of an endoscope to allow the surgical instrument access to the area near the tip of the endoscope. These surgical instruments may be formed of material(s) or include components that distort the EM field when the surgical instrument is moved. Typically, the endoscope is substantially stationary while the surgical instrument is passed through the working channel or navigated within the area adjacent to the endoscope tip (e.g., the physician user does not navigate the endoscope while simultaneously moving the surgical instrument).

The EM instrument sensor may be configured to generate one or more EM sensor signals in response to detection of the EM field generated by the EM field generator 110. Distortions in the EM field may be detectable by the EM instrument sensor (e.g., by the EM sensor coils 305) located on the distal end 300 of the endoscope based on the EM sensor signals. Since the EM instrument sensor is used for navigation and localization of the endoscope tip, changes in the EM field detected by the EM instrument sensor are interpreted by the EM spatial measurement system as movement of the endoscope tip. However, since the endoscope is typically stationary during movement of the surgical instrument, changes in the EM field as detected by the EM instrument sensor may be determined to be indicative of distortion in the EM field rather than movement of the endoscope when the endoscope is known to be stationary.

There are a number of methods by which the surgical robotic system may be able to determine that the endoscope is stationary. For example, the endoscope position and movement may be controlled by the user, and thus, when the system is not actively receiving command data for repositioning, controlling, or otherwise navigating the endoscope, the system can determine that the endoscope is stationary. The system may use additional navigation and control data to confirm whether the endoscope is stationary. For example, the vision data 92 and robotic command and kinematics data 94 may be analyzed to determine that the endoscope is stationary.

The system may be able to detect local EM distortion based on the EM sensor signals generated by the EM instrument sensor. For example, the system may calculate one or more baseline values of one or more metrics related to the position and/or movement the distal end of the instrument. The baseline values may be calculated at a first time based on the EM sensor signals corresponding to the first time generated by the EM instrument sensor. In one embodiment, the first time may be prior to insertion of the endoscope into the patient (e.g., the baseline metric may be a preoperative measurement). In one example, the first time at which the baseline measurement is calculated is after the environment 100 has been set up for a surgical procedure. For example, one or more of the cart 11, tower 30, robotic arms 12, EM field generator 110, and C-arm may be initially positioned in preparation for a surgical operation. Since the movement of one or more of the cart 11, tower 30, robotic arms 12, EM field generator 110, and C-arm may affect the EM field generated by the EM field generator 110, the baseline metric(s) may be measured after positioning of the various devices within the environment 100 so that further movement of the devices may be minimized, thereby minimizing distortions to the EM field that would be introduced due to the movement of these devices.

However, the baseline metric may be calculated and/or updated at various times other than prior to the surgical operation in other embodiments. For example, it may be desirable to calculate and/or update the baseline measurement after movement of the C-arm to reduce the effects of the movement and/or repositioning of the C-arm on the measured EM field. In another embodiment, the baseline metric(s) may be automatically calculated in response to the start of the surgical procedure. Since the baseline measurements may be calculated in a relatively short time period (e.g., in a number of seconds), the baseline metric(s) may be sufficiently accurate when calculated as the endoscope is inserted into the patient via a patient introducer.

Figure 19A:
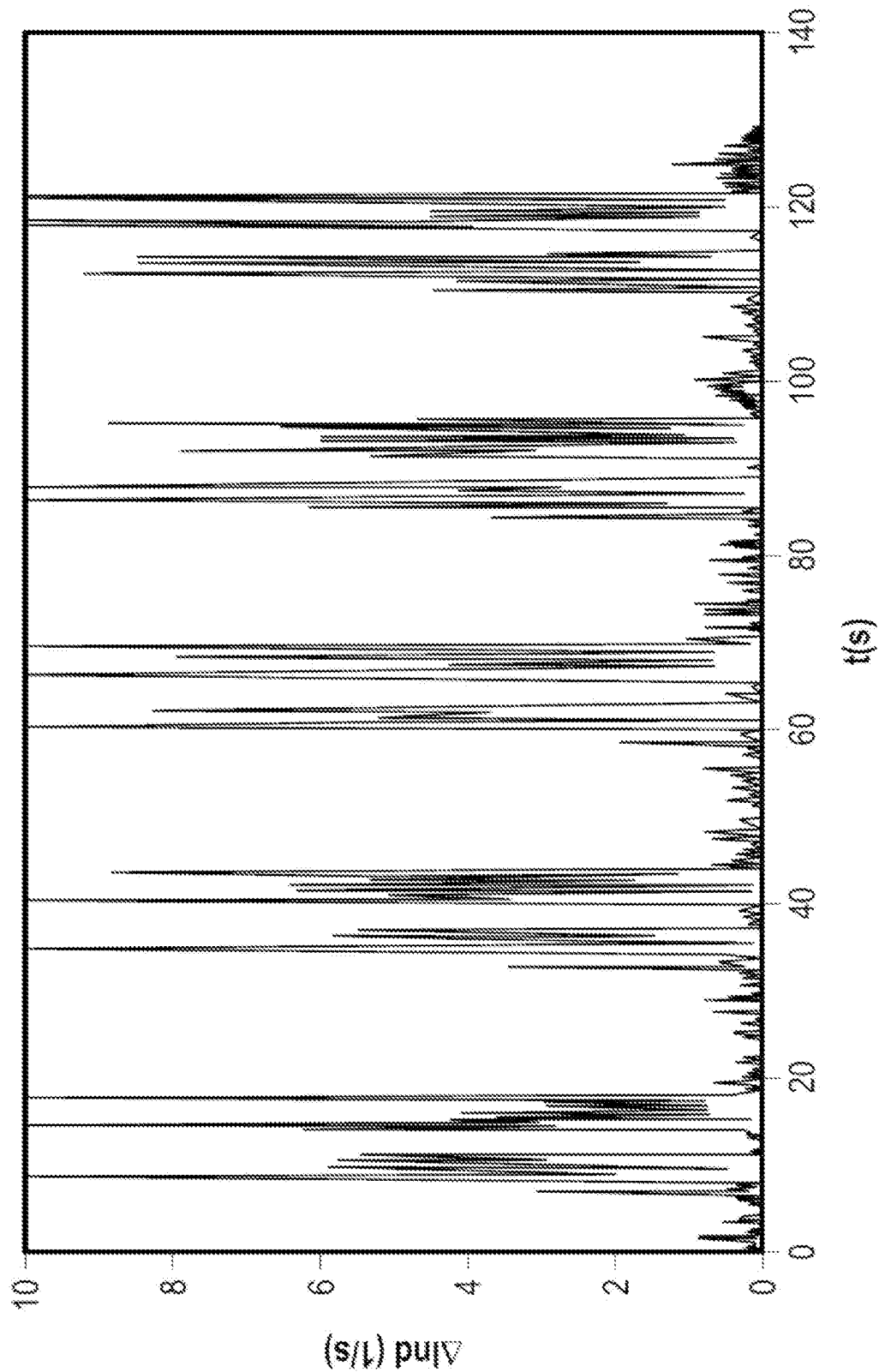
FIGS. 19A-C provide graphs of metrics which illustrate changes in the metrics which may be indicative of local EM distortion.
Figure 19B:
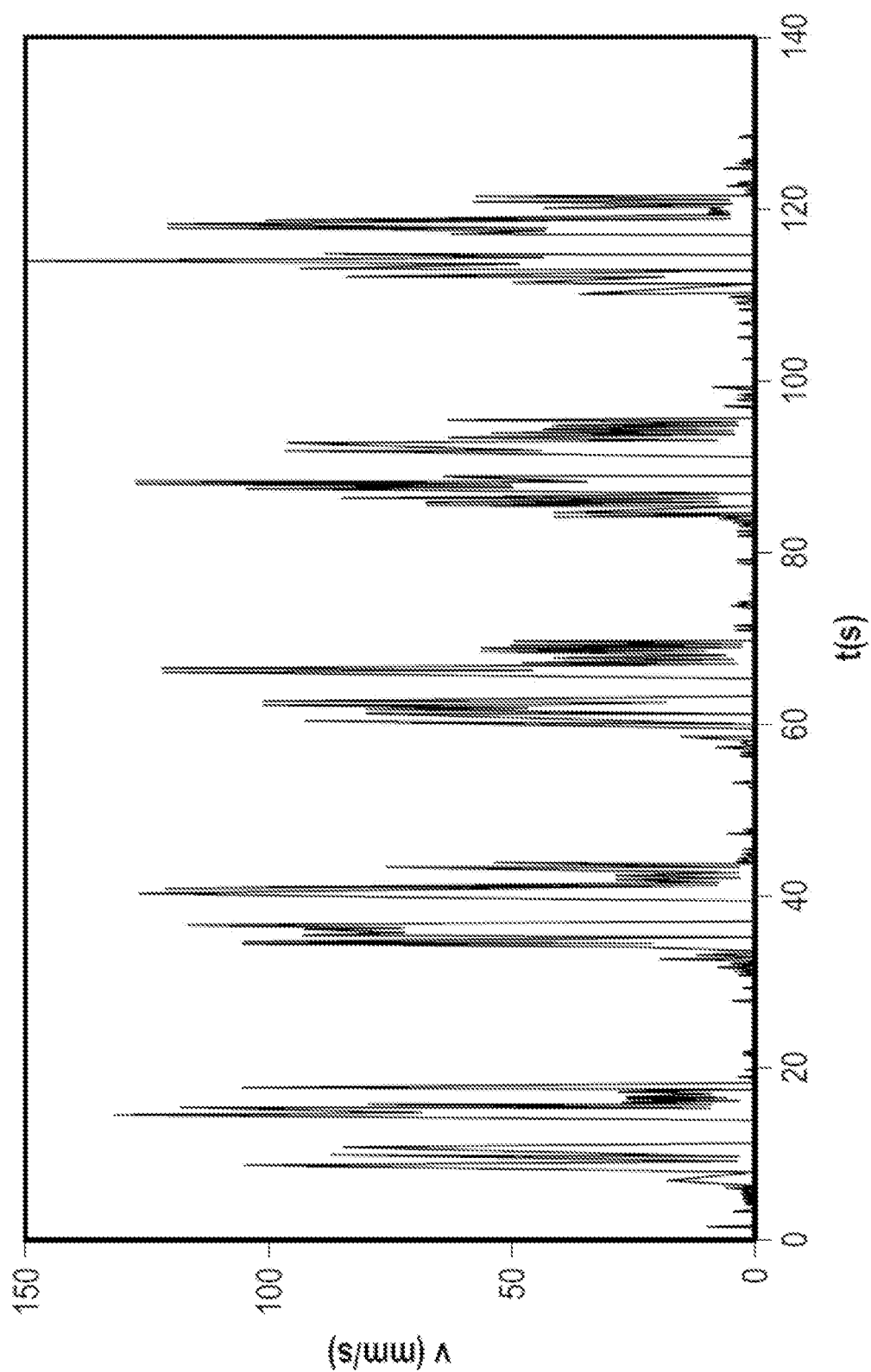
Figure 19C:
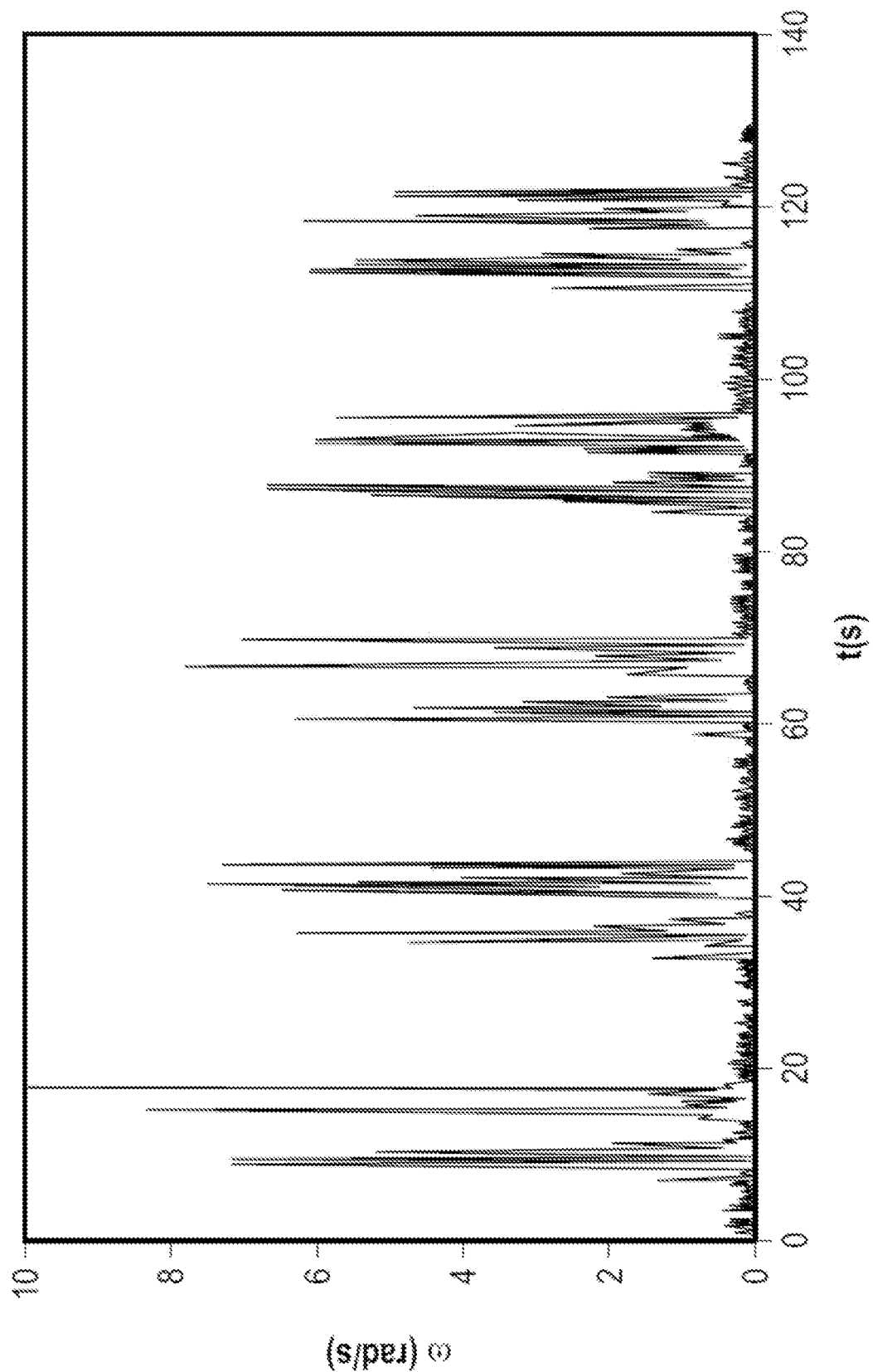

There are a number of different metrics which may be calculated by the system based on the EM sensor signals, each of which may be used to detect local EM distortion. Example metrics which may be calculated include: a linear velocity of the distal end 300 of the instrument, an angular velocity of the distal end 300 of the instrument, and a change in an indicator value. FIGS. 19A-C provide graphs of these metrics which illustrate changes in the metrics which may be indicative of local EM distortion. In particular, FIG. 19A illustrates a change in indicator value metric, FIG. 19B illustrates a linear velocity metric, and FIG. 19C illustrates an angular velocity metric.

In certain implementations, the system may calculate one or more of: an indicator value Ind, a position $\vec{P}$ of the distal end 300 of the instrument, and an angular orientation $\vec{Q}$ of the distal end 300 of the instrument. These values may be used by the system in the navigation and localization of the instrument. In certain implementations, the indicator value Ind, position $\vec{P}$, and angular position $\vec{Q}$ values may be calculated based on 5DoF measurements (e.g., 3 positional DoF and 2 angular DoF) generated based on the EM sensor signals received from the coil(s) 305. The indicator value Ind may be a value that is representative of the quality of the position $\vec{P}$ and angular orientation $\vec{Q}$ measurements. Thus, the indicator value Ind may be compared to a threshold value by the system to determine whether the position $\vec{P}$ and angular orientation $\vec{Q}$ measurements are sufficiently accurate to be used in navigation and localization. In certain embodiments, the indicator value Ind may be calculated using a goodness of fit (GOF) algorithm between the 5DoF measurements received from the coil(s) 305 and a model of the endoscope tip as a rigid body.

Each of the graphs illustrated in FIGS. 19A-19C illustrate certain metrics which may be determined as a surgical instrument (e.g., forceps) is passed through an endoscope. These graphs were generated based on the same events, where the forceps were passed through the endoscope five times while the endoscope remained stationary.

Specifically, FIG. 19A illustrates a change in indicator value metric ΔInd, which is measured in Hz (e.g., 1/s). The five events where the forceps were passed through the endoscope are visible where the change in indicator value metric ΔInd increases to a level that is significantly higher than the noise in the change in indicator value metric ΔInd.

The change in indicator value metric may be calculated as a time change in the indicator value using the following equation:

$$\Delta Ind = \frac{Ind(t_i) - Ind(t_{i-1})}{t_i - t_{i-1}} \quad (1)$$

Where $\Delta Ind$ is the change in indicator value metric, Ind is the indictor value, $t_i$ is a current time (e.g., a time at which the indicator value is sampled and/or determined), and $t_{i-1}$ is a previous time.

Similarly, FIG. 19B illustrates a linear velocity metric v, which is measured in mm/s. Here, each of the forceps movement events is visible as linear velocity values which are greater than noise in the baseline linear velocity value. The linear velocity metric may be calculated as a time change in position of the endoscope using the following equation:

$$v(t_i) = \frac{\left\| \vec{P}(t_i) - \vec{P}(t_{i-1}) \right\|}{t_i - t_{i-1}} \quad (2)$$

Where v is the linear velocity metric and $\vec{P}$ is the position of the distal end 300 of the instrument.

Finally, FIG. 19C illustrates an angular velocity metric ω, which is measured in rad/s. The angular velocity metric may be calculated as a time change in the orientation of the endoscope using the following equation:

$$\omega(t_i) = \frac{\left| \cos^{-1}\left(2 \cdot dot\left(\vec{Q}(t_i), \vec{Q}(t_{i-1})\right)^2 - 1\right) \right|}{t_i - t_{i-1}} \quad (3)$$

Where ω is the angular velocity metric and $\vec{Q}$ is the angular orientation of the distal end 300 of the instrument.

As shown in FIGS. 19A-19C, each of the calculated metrics illustrates a deviation from a baseline value (e.g., where the baseline value is set to 0) for each of the five individual endoscope movement events. By selecting appropriate threshold values or limits, these deviations from the baseline can be detected.

After the baseline value(s) of the metric(s) have been calculated, the system may periodically calculate one or more updated values of the one or more metrics during a time period after the first time based on EM sensor signals from the one or more EM sensor signals corresponding to the time period after the first time. For example, the system may periodically calculate updated values of the metric(s) in order to determine whether local EM distortion is occurring. When the system has determined that the instrument is stationary, changes in one or more of the metric(s) may be indicative of local EM distortion.

Accordingly, the system may determine whether a difference between the one or more updated values and the one or more baseline values is greater than a threshold value. A different threshold value may be set for each of the metric(s) being calculated. When the difference is greater than the threshold value, the system may determine that the EM field has been distorted.

Figure 20:
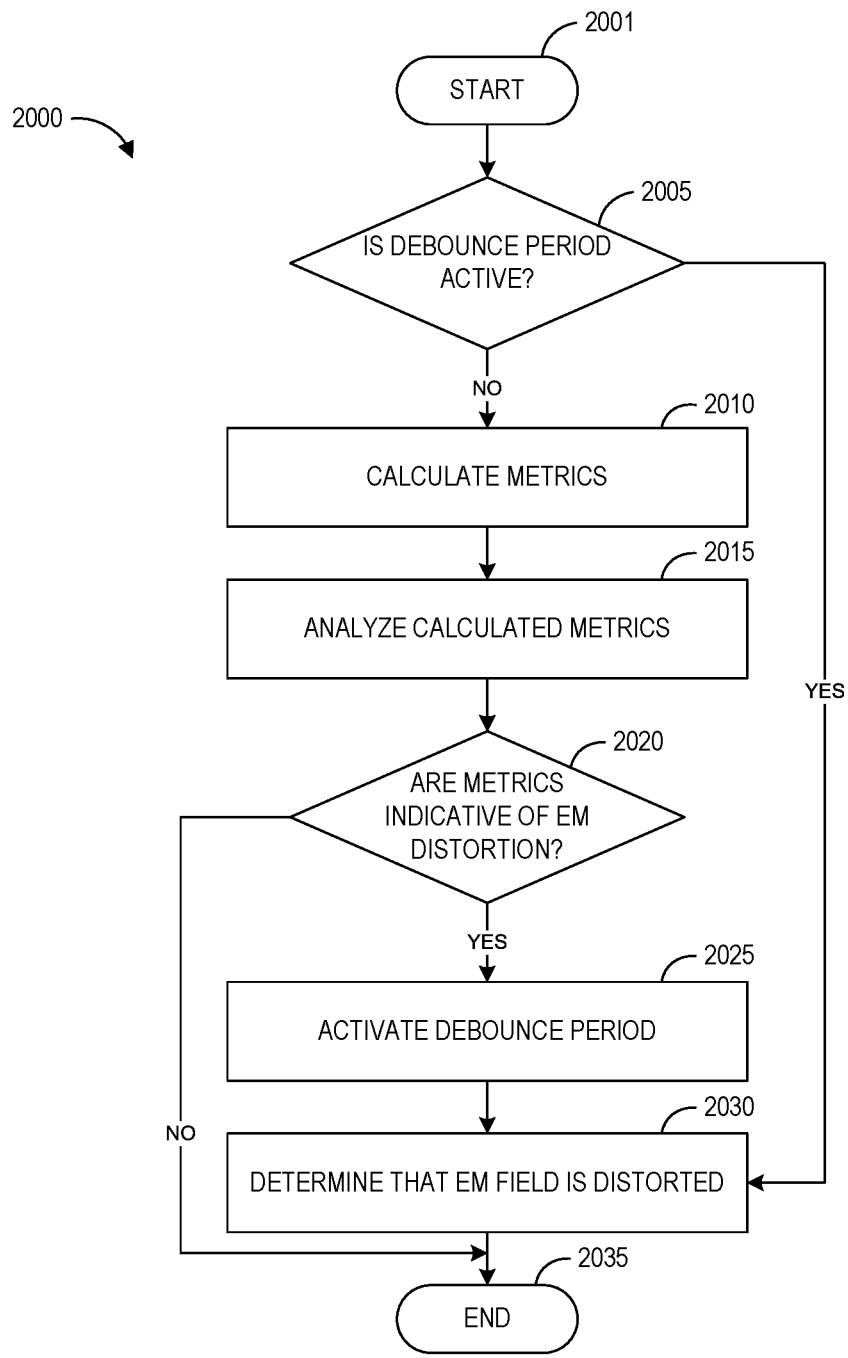
FIG. 20 provides a flowchart illustrating an example methodology of determining that local EM distortion has occurred.

FIG. 20 provides a flowchart illustrating an example methodology of determining that local EM distortion has occurred. The method 2000 begins at block 2001. At block 2005, the system determines whether a debounce period is active. As used herein, the debounce period may generally refer to a predetermined period of time which limits the frequency at which EM distortion can be determined to have occurred. For example, in certain implementations, while the debounce period is active, the system will not calculate new metrics and/or evaluate metrics to determine whether EM distortion has occurred. The system may determine that EM distortion has effectively occurred for the entire debounce period and resume determining whether EM distortion has occurred once the debounce period has expired. A debounce flag, stored as data in the system, may be used to indicate that the debounce period is active. The debounce period may be set as an interval that defines how often EM distortion may be flagged. For example, a new occurrence of EM distortion may not be set while the debounce period is active.

If the debounce period is active, the method 2000 continues at block 2030, where local EM distortion is determined to have occurred. When the debounce period is not active, the method 2000 continues at block 2010 where the system calculates a number of metrics. In one example, the system calculates a linear velocity metric, an angular velocity metric, and a change in indicator value metric. At block 2015, the system analyzes the calculated metrics that have been stored over a window of time, including determining the standard deviation of each of the metrics. At block 2020, the system determines whether the analyzed metrics are indicative of local EM distortion. This may include comparing each of the metrics against a corresponding threshold value and comparing the standard deviations against corresponding threshold values. In some cases, the system may attempt to limit the occurrences of false positives by comparing the occurrences of local distortion events with some criteria over time. For example, in one embodiment, when a quorum or some number of the comparisons in a given time window are indicative of local EM distortion, the system may determine that the metrics are indicative of local EM distortion. It is to be appreciated that such an approach is merely one approach and other embodiments may employ any suitable approach, such as determining that a local EM distortion has occurred when the metrics are indicative for some number of consecutive comparisons.

At block 2025, in response to determining that the metrics are indicative of local EM distortion, the system activates the debounce period, which may include activating the debounce flag. At block 2030, the system determines that local EM distortion has occurred, which may include setting an EM distortion flag and/or a local EM distortion flag. The method ends at block 2035. It is to be appreciated that the system may perform a number of actions in response to detecting local EM distortion. Some exemplary responses are described below.

B. Global Distortion.

Another possible source of EM distortion is global EM distortion. As used herein, global EM distortion generally refers to EM distortion caused by sources that are located within the environment 100 but are not directly adjacent to the distal end of an instrument. For example, certain surgical procedures may be performed with the use of fluoroscopic imaging, which may include the placement of a C-arm next to the patient. An example setup for a fluoroscopic procedure is shown in FIG. 5 in which the C-arm is positioned such that an emitter and detector are placed to be positioned on opposing sides of the patient. The C-arm may be positioned in anteroposterior (AP) position as an initial position for the surgical procedure.

Due to the technical requirements of fluoroscopy, the C-arm typically includes a number of components which may cause distortion in the EM field generated by the EM field generator 110. For example, the production of X-rays by the emitter may require components which produce and/or affect EM fields as a byproduct of generating the X-rays. However, while the C-arm remains in the same position, the EM field distortions caused by the C-arm may be relatively static. That is, while the EM field distortions caused by the C-arm may distort the EM field measured by EM sensors (e.g., EM patch sensors 105 and EM instrument sensors 305), the EM spatial measurement system may still be able to effectively navigate and localize the instrument if the EM field is stable. However, when the position of the C-arm is moved during navigation and/or localization, the EM field may be dynamically distorted, causing the position and/or orientation of the instrument as calculated by the EM spatial measurement system to shift from the instrument's actual position and orientation. Thus, detection of such global EM distortion events is desirable in order to enable the EM spatial measurement system to act on global EM distortion events. While a C-arm has been provided as an example of a global EM distortion source, other global EM distortion sources may also be detected. Other materials which may be sources of global EM distortion include electrically conductive materials and magnetic materials as well as any EM field source.

Figure 21:
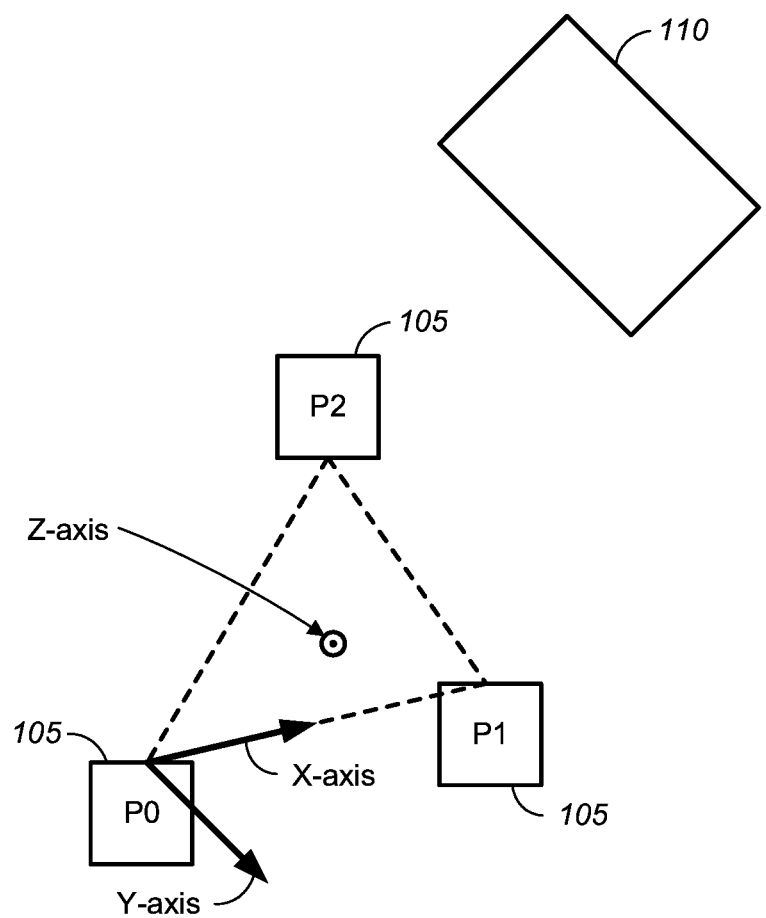
FIG. 21 illustrates an embodiment of a system which may be used to detect global EM distortion in accordance with aspects of this disclosure.

FIG. 21 illustrates an embodiment of a system which may be used to detect global EM distortion in accordance with aspects of this disclosure. The FIG. 21 embodiment includes an EM field generator 110 and three EM patch sensors 105 positioned within a working volume of the EM field generator 110. As discussed above, the EM patch sensors 110 may be used to detect respiration of the patient, which can be used to correct the navigation and localization of an instrument via an EM instrument sensor located thereon. In addition, the patch sensors 105 may be used to detect global EM distortion, which will be described in greater detail below.

In the embodiment of FIG. 21, the patch sensors 105 include three patch sensor P0, P1, and P2. However, other implementations may include more or fewer patch sensors 105. When the EM spatial measurement system includes a greater number of patch sensor 105, the system may be able to calculate a greater number of metrics which may be used to track global EM distortion, improving the robustness of the distortion tracking.

When placed on a patient, each of the EM patch sensors 105 may be configured to generate a one or more EM sensor signals in response to detection of the EM field. Similar to the coil(s) 305, the EM spatial measurement system may be able to generate 5DoF measurements based on the EM sensor signals received from the EM patch sensors 105. When at least two EM patch sensors 105 are available, the system may be able to calculate a relative position metric and a relative angle metric. Further, when at least three EM patch sensors 105 are available, the system may be able to calculate a patch area metric and a patch space 6DoF metric.

The EM patch sensors are attached to various locations on the patient's body. As such, the relative distance, relative angle, patch space, and patch area metrics are relatively stable and may vary based only on the user's respiration. By tracking the user's respiration, the system can filter out changes in the calculated metrics caused to respiration. Once respiration variations have been filtered from the metrics any remaining changes may therefore be attributed to global EM distortion.

The relative position metric may be representative of the relative position between two of the EM patch sensors (e.g., P1 and P2). The relative position metric for EM patch sensors P1 and P2 may be calculated using the following equation:

$$dP1P2_{rel} = \sqrt{(P1_x - P2_x)^2 + (P1_y - P2_y)^2 + (P1_z - P2_z)^2} \quad (4)$$

Where $dP1P2_{rel}$ is the relative position metric, $P1_x$ and $P2_x$ are the respective X-coordinates of the EM patch sensors P1 and P2, $P1_y$ and $P2_y$ are the respective Y-coordinates of the EM patch sensors P1 and P2, and $P1_z$ and $P2_z$ are the respective Z-coordinates of the EM patch sensors P1 and P2.

The relative angle metric may the relative angle between the Z-axis of two of the EM patch sensors (e.g., P1 and P2). The relative angle metric may be calculated using the following equation:

$$\theta_{rel} = \cos^{-1}(\text{dot}(P1_{Rz}, P2_{Rz})) \quad (5)$$

Where $\theta_{rel}$ is the relative angle metric, $P1_{Rz}$ is the Z-axis of the EM patch sensor P1, and $P2_{Rz}$ is the Z-axis of the EM patch sensor P2.

The patch area metric may be the area created by the EM patch sensors and may be calculated using the following equation:

$$\text{area} = \sqrt{s*(s - dP1P2_{rel}) + (s - dP1P3_{rel}) + (s - dP2P3_{rel})} \quad (6)$$

Where area is the patch area metric, the relative positions are calculated according to equation (4), and s may be calculated using the following equation:

$$s = \frac{dP1P2_{rel} + dP1P3_{rel} + dP2P3_{rel}}{2} \quad (7)$$

The patch space 6DoF metric may be the 6DoF position and orientation of the space created by the EM patch sensors and may be calculated using the following equations:

$$X_{axis} = \frac{(P0 - P1)}{\text{norm}(P0 - P1)} \quad (8)$$

$$Z_{axis} = \frac{\text{cross}(P0 - P1, P0 - P2)}{\text{nrom}(\text{cross}(P0 - P1, P0 - P2))} \quad (9)$$

$$Y_{axis} = \frac{\text{cross}(P0 - P1, Z_{axis})}{\text{norm}(\text{cross}(P0 - P1, Z_{axis}))} \quad (10)$$

Where P0 is the position of EM patch sensor P0 in EM field generator 110 space and is used as the origin, P1 is the position of EM patch sensor P1 in EM field generator 110 space, and P2 is the position of EM patch sensor P2 in EM field generator 110 space. Examples of the $X_{axis}$, $Y_{axis}$, and $Z_{axis}$ of the patch space metric calculated by equations (8)-(10) are illustrated in FIG. 21.

After the baseline value(s) of the metric(s) have been calculated, the system may periodically calculate one or more updated values of the one or more metrics during a time period after the first time based on EM sensor signals from the one or more EM sensor signals corresponding to the time period after the first time. For example, the system may periodically calculate updated values of the metric(s) in order to determine whether global EM distortion is occurring. Since changes in the values of the metrics are affected only by the patient's respiration, when the difference between one or more of the updated metrics and the baseline values of the one or more metrics is greater than a threshold value, the system may determine that global EM distortion has occurred. Further, in certain embodiments, the respiration can be filtered out of the calculated metrics, and thus, any remaining changes in the metric(s) can be determined to be caused by distortions in the EM field.

Accordingly, the system may determine whether a difference between the one or more updated values and the one or more baseline values is greater than a threshold value. A different threshold value may be set for each of the metric(s) being calculated. When the difference is greater than the threshold value, the system may determine that the EM field has been distorted.

Figure 22:
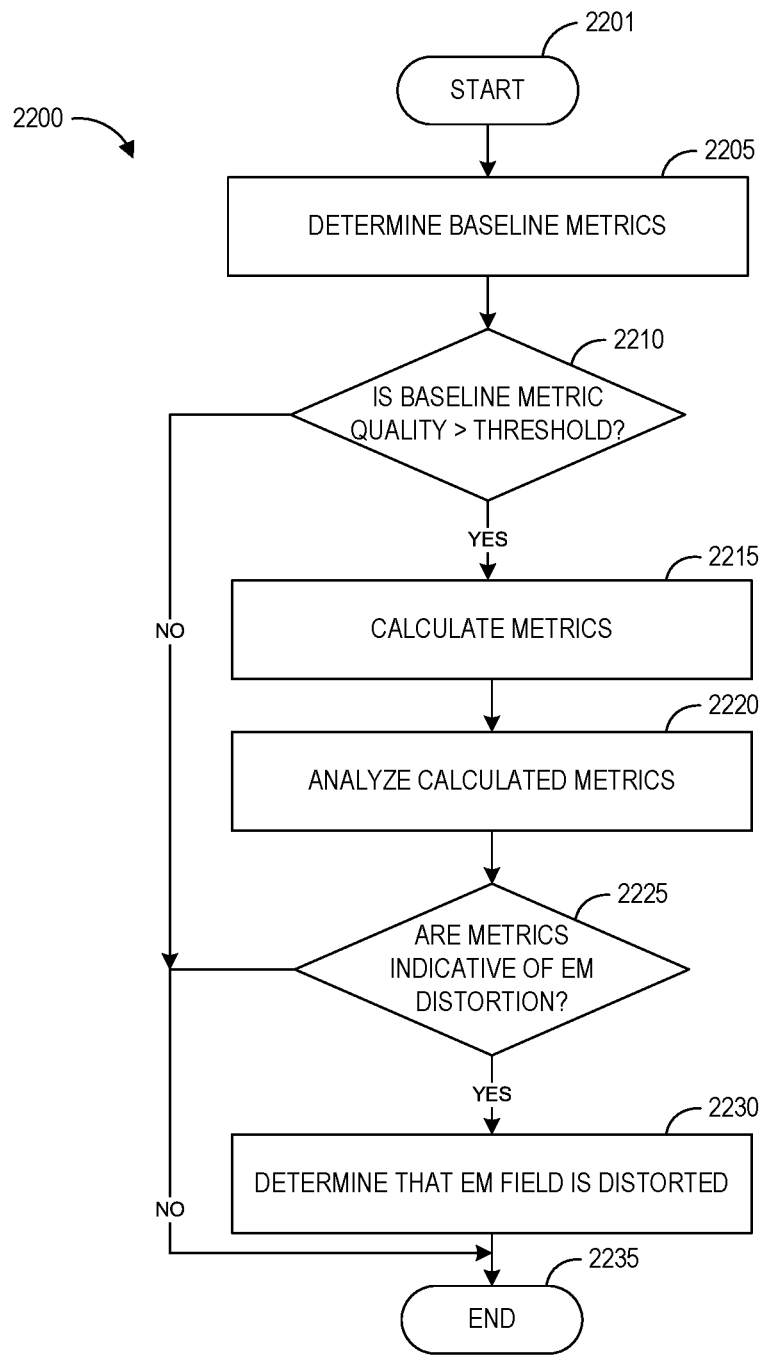
FIG. 22 provides a flowchart illustrating an example methodology of determining that global EM distortion has occurred.

FIG. 22 provides a flowchart illustrating an example methodology of determining that global EM distortion has occurred. The method 2200 begins at block 2201. At block 2205, the system determines baseline metrics for each of the calculated metrics. This may include retrieving baseline values for the metrics from memory or calculating baseline metrics based on EM sensor signals received from EM patch sensors 105. At block 2210, the system determines whether the baseline metric quality is greater than a threshold quality. When the baseline metric quality is not greater than the threshold quality, the method 2200 ends and the method 2200 may repeat by attempting to collect better quality baseline metrics.

When the baseline metric quality is greater than the threshold quality, the method 2200 continues at block 2215, where the system calculates a number of metrics. In one example, the system calculates a relative distance metric, a relative angle, metric, a 6DoF patch space metric, and a patch area metric. At block 2220, the system analyzes the calculated metrics that have been stored over a window of time, including determining the standard deviation of each of the metrics. At block 2225, the system determines whether the analyzed metrics are indicative of global EM distortion. This may include comparing each of the metrics against a corresponding threshold value and comparing the standard deviations against corresponding threshold values. When a quorum of the comparisons are indicative of global EM distortion, the system may determine that the metrics are indicative of global EM distortion.

At block 2230, in response to determining that the metrics are indicative of global EM distortion, the system determines that global EM distortion has occurred, which may include setting an EM distortion flag and/or a global EM distortion flag. The method ends at block 2235. It is to be appreciated that the system may perform a number of actions in response to detecting global EM distortion. Some exemplary responses are described below.

C. Motion Detection.

The navigation and localization of an instrument based on EM data may also be negatively affected when one or more of the patient and the EM field generator 110 is moved. There are generally two scenarios for movement of the EM field generator 110 or the patient. First, the EM field generator 110 or patient may be moved and settle at a new position. Second, the EM field generator 110 or patient may receive an impulse force (e.g., be bumped) and experience a temporary oscillation in place before returning to approximately the same position as before receiving the impulse force. Since the movement of either the patient or the EM field detector 110 may be incorrectly interpreted as movement of an instrument, local EM distortion, and/or global EM distortion, it may be desirable to detect the movement of the EM field generator 110 or patient.

Since the relative distance between the EM patch sensors 105 on the patient is relatively stable, the movement of the EM field generator 110 or patient will result in a change in the calculated absolute distance between each of the EM patch sensors 105 and the EM field generator 110. Such movement may also result in a change in the calculated absolute angle between the EM patch sensors 105 and the EM field generator 110.

When at least one EM patch sensors 105 is available, the system may be able to calculate an absolute position metric and an absolute angle metric. Further, when at least three EM patch sensors 105 are available, the system may to use the patch space 6DoF metric as described in connection with equations (8)-(10). Additional examples of the at least one metric include: an absolute position of each of the EM sensors with respect to the field generator, the root of the sum of the squares of the absolute positions of the EM sensors with respect to the field generator, the absolute angle of each of the EM sensors with respect to the field generator, the root of the sum of the squares of the absolute angles of the EM sensors with respect to the field generator, and the position and orientation of a space created by the EM sensors.

The absolute position metric may be representative of the absolute distance between a given one of the EM patch sensors 105 and the EM field generator 110. The absolute position metric may be calculated using the following equation:

$$D_{abs} = \sqrt{P_x^2 + P_y^2 + P_z^2} \quad (11)$$

Where $D_{abs}$ is the absolute position metric, $P_x$ is the position of the EM patch sensor 105 with respect to the EM field generator 110 in the X-axis, $P_y$ is the position of the EM patch sensor 105 with respect to the EM field generator 110 in the Y-axis, and $P_z$ is the position of the EM patch sensor 105 with respect to the EM field generator 110 in the Z-axis.

The absolute angle metric may be representative of the absolute angle between a given one of the EM patch sensors 105 and the EM field generator 110. The absolute angle metric may be calculated using the following equation:

$$\theta_{abs} = \cos^{-1}(dot(P_{Rz}, FG_{Rz})) \quad (12)$$

Where $\theta_{abs}$ is the absolute angle metric, $P_{Rz}$ is the Z-axis of the EM patch sensor P1, and $FG_{Rz}$ is the Z-axis of the EM field generator 110.

Since movement of the EM field generator 110 and/or the patient is temporary, the EM spatial measurement system may be configured to determine the period of time for which the patient and/or the EM field generator 110 is moving.

Thus, the EM tracking system may be able to detect movement of the patient and/or the EM field generator 110 based on the EM sensor signals generated by the EM patch sensor(s). For example, the system may calculate a baseline value of at least one metric based on the one or more EM sensor signals. The baseline value of the at least one metric may correspond to a first time. In one embodiment, the first time may be prior to insertion of the endoscope into the patient (e.g., the baseline metric may be a preoperative measurement). However, for movement detection, the baseline value may be the most recent stable value for the metric (e.g., changes to the metric are less than a threshold value for a period of time).

The EM tracking system may calculate an updated value of the at least one metric based on the one or more EM sensor signals. The updated value of the at least one metric may correspond to a second time after the first time. The system may then compare the updated value of the metric to the baseline value of the metric. When the difference between the updated value and the baseline value of the metric is greater than a threshold value, the system may determine that at least one of the patient and the field generator has moved during a time period that includes the first time and the second time.

Once the system has determined that one of the patient and the EM field generator 110 has moved, the system may determine whether one of the patient or the EM field generator 110 has changed its pose (e.g., has moved to a new position). For example, in response to determining that at least one of the patient and the field generator has moved, the system may calculate a frequency value of the at least one metric based on the one or more EM sensor signals corresponding to a frequency of a change in positioning of the EM sensor at a third time, subsequent to the second time. The system may then compare the frequency value to the threshold frequency value. When the frequency value is greater than the threshold frequency value, the system may determine that at least one of the patient and the field generator has changed its pose.

The EM tracking system may also determine whether one of the patient and the EM field generator 110 receives an impulse force and returns to an initial state. For example, the system may, in response to determining that at least one of the patient and the field generator has moved, calculate a subsequent value of the at least one metric based on the one or more EM sensor signals. The subsequent value of the at least one metric may correspond to a positioning of the EM sensor at a third time, subsequent to the second time. The system may then determine that the field generator received an impulse force and returned to an initial state after receiving the impulse force, in response to the subsequent value being within an error threshold of the baseline value.

Prior to selecting the third time for calculating the subsequent value, the system may determine that an interval value of the at least one metric has stabilized for an interval of time prior to the third time and select the third time in response to determining that the interval value of the at least one metric has stabilized. Thus, the system may determine that the patient or the EM field generator 110 has settled at a final pose before determining whether the patient or EM field generator 110 has moved to a new pose or has settled to its initial pose.

In one implementation, the system may determine that the pose of the patient or the EM field generator 110 has stabilized based on the maximum and minimum values of the at least one metric during the interval of time. For example, the system may calculate a maximum value and a minimum value of the at least one metric during the interval of time, calculate the difference between the maximum and minimum values of the at least one metric, and determine that that the interval value of the at least one metric has stabilized for the interval of time in response to the difference between the maximum and minimum values of the at least one metric being less than a threshold difference value. When changes to the at least one metric are determined to be less than the threshold difference value, the system may determine that the changes in the metric are due to noise and not oscillation of the patient or the EM field generator 110.

In another example, the system may calculate a subsequent value of the at least one metric based on the one or more EM sensor signals in response to determining that at least one of the patient and the field generator has moved. The subsequent value of the at least one metric may correspond to a positioning of the EM sensor at a third time, subsequent to the second time. The system may then determine that at least one of the patient and the field generator has changed its pose in response to the subsequent value being outside an error threshold of the baseline value. For example, as discussed above, the metric may be the absolute position or absolute angle of one or more of the EM patch sensors 105. If the baseline value for the absolute difference or absolute angle changes and is stable at a new value, this is indicative of at least one of the patient and the EM field generator 110 being moved and settling at a new position.

Figure 23:
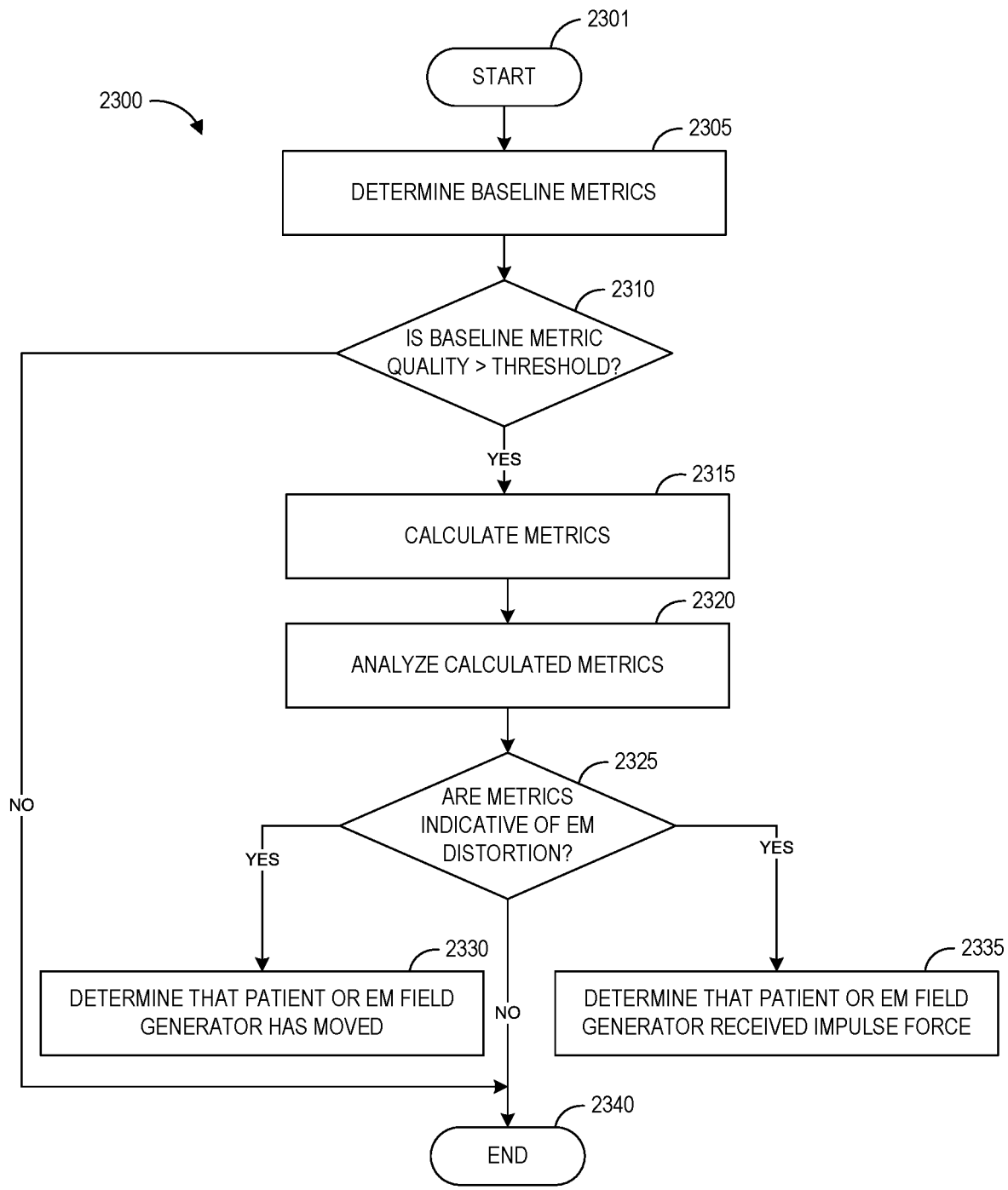
FIG. 23 provides a flowchart illustrating an example methodology of determining that one of a patient and an EM field generator has moved.

FIG. 23 provides a flowchart illustrating an example methodology of determining that one of a patient and an EM field generator has moved. The method 2300 begins at block 2301. At block 2305, the system determines baseline metrics for each of the calculated metrics. This may include retrieving baseline values for the metrics from memory or calculating baseline metrics based on EM sensor signals received from EM patch sensors 105. At block 2310, the system determines whether the baseline metric quality is greater than a threshold quality. When the baseline metric quality is not greater than the threshold quality, the method 2300 ends and the method 2300 may repeat by attempting to collect better quality baseline metrics.

When the baseline metric quality is greater than the threshold quality, the method 2230 continues at block 2315, where the system calculates a number of metrics. In one example, the system calculates an absolute difference metric, an absolute angle metric, and a 6DoF patch space metric. At block 2320, the system analyzes the calculated metrics that have been stored over a window of time, including determining the standard deviation of each of the metrics. At block 2325, the system determines whether the analyzed metrics are indicative of at least one of the patient and the EM field generator being moved or at least one of the patient and the EM field generator receiving an impulse force. This may include comparing each of the metrics against a corresponding threshold value and comparing the standard deviations against corresponding threshold values. When a quorum or some threshold number of the comparisons are indicative of at least one of the patient and the EM field generator being moved, the method continues at block 2330. When a quorum or some threshold number of the comparisons are indicative of at least one of the patient and the EM field generator receiving an impulse force, the method 2300 continues at block 2335.

At block 2330, in response to determining that the metrics are indicative of at least one of the patient and the EM field generator being moved, the system may set an EM distortion flag and/or a movement flag. At block 2330, in response to determining that the metrics are indicative of at least one of the patient and the EM field generator receiving an impulse force, the system may set an EM distortion flag and/or an impulse force flag. The method ends at block 2235. It is to be appreciated that the system may perform a number of action in response to detecting movement of the EM field generator. Some exemplary responses are described below.

D. Responses to Detection of EM Distortion

The EM tracking system may perform one or more of a number of techniques in response to detection EM distortion. The specific technique performed may depend on one or more of: the type of EM distortion detected (e.g., local or global EM distortion, distortion due to movement, etc.), the magnitude of the EM distortion, the location of the EM distortion, etc.

In one implementation, the system may refrain from using or otherwise limit the weight given to EM data in navigation and/or localization of an instrument. When refraining from using EM data, the navigation and/or localization performed by the system may rely on other types of data during EM distortion. Specifically, in one embodiment, the system may detect that the EM distortion flag has been set and then as a consequence of the EM distortion flag being set, refrain from or otherwise limit the weight given to determining the position of the distal end of an instrument based on EM sensor signals by lowering a confidence value (or any other suitable weighting) corresponding to an EM location based algorithm. The use of confidence values and weighting to different location algorithms is discussed in U.S. patent application Ser. No. 15/268,238, filed on Sep. 16, 2016, the contents of which are herein incorporated in its entirety.

In some implementations, in response to determining that the EM field is distorted, the system may calculate the amount of distortion. The amount of EM field distortion may be proportional to the change in one or more of the calculated metrics. In this implementation, the system may calculate an amount of the distortion in the EM field based on one or more updated values calculated at a second time and one or more baseline values calculated a first time prior to the second time. The system may encode an indication of the amount of the distortion and provide the encoded indication of the amount of distortion to a display configured to render encoded data. Accordingly, the user may be notified of the amount of the EM field distortion. The user may then be able to determine whether to use navigation based on EM data during the surgical procedure.

In certain embodiments, the system may use the amount of distortion to alter the weight of the EM data used in the navigation and/or localization techniques. As the EM distortion increases, the system may assign a lower weight to the EM data when generating location data 96 for the distal tip of a medical instrument.

The system may also be able to determine an area in which the distortion in the EM field is greater than a threshold distortion value. For example, the relative distance metrics may be used to determine that the area surrounding one of the EM patch sensors is experiencing EM distortion. That is, if the relative distance between EM patch sensor P1 and each of EM patch sensors P0 and P2 has changed by more than a threshold value, but the relative distance between EM patch sensors P0 and P2 is substantially unchanged, the system may determine that the EM field in the area near EM patch sensor P1 has been distorted.

In response to determining that the EM field near one of the EM patch sensors 105 has been distorted, the system may adjust (e.g., reduce) a weight applied to EM data received from the identified EM patch sensor 105. The system may also indicate to the user the area in which EM field distortion is occurring. The user may then be able to determine whether to continue with navigation using EM data based on whether the target site is within the distorted area. Alternatively, the system may automatically determine whether to continue using EM data for navigation based on the current location of the instrument with respect to the EM distorted area.

In certain embodiments the system may also access a model representative of a luminal network of the patient and calculate a mapping between a coordinate frame of the EM field and a coordinate frame of the model based on at least one of: (i) the one or more baseline values and (ii) the one or more updated values. The system may further refrain from using the one or more updated values in calculating the mapping in response to determining that the EM field has been distorted.

E. Alignment.

Prior to performing a surgical procedure that uses EM data for navigation and/or localization, it is desirable to align the patient with the EM field generator 110. More precisely, it is desirable to align the EM field generator 110 with an anatomical feature of the patient on which the surgical procedure is to be performed. One advantage to performing such an alignment procedure is that the EM field generator 110 may have a working volume in which EM sensors are able to more accurately measure the EM field. That is, when one or more of the EM sensors are outside of the working volume, the EM sensor signals generated by the EM sensors may not be sufficiently reliable for navigation and/or localization, respiration tracking, and/or EM distortion detection.

As discussed above, a number of EM patch sensors 105 may be placed on the patient at prescribed locations which surround, or at least partially overlap, an area of interest. The area of interest may be an anatomical feature of the patient on which the surgical procedure is to be performed. One example of an anatomical feature is a luminal network, such as luminal network 140. The EM tracking system may provide guidance to the user on where to position the EM patch sensors 105 on the patient and where to position the EM field generator 110 such that the EM patch sensors 105 are within a working volume of the EM field generator 110. When the EM patch sensors 105 are appropriately positioned, the positioning of the EM patch sensor's within the working volume may guarantee that the patient's area of interest is aligned with the EM field generator 110.

An example procedure for aligning the EM field generator 110 with a patient will be described in connection with a bronchoscopy procedure. However, this procedure may be modified for any type of robotic-assisted surgical procedure in which EM data is used for navigation and/or localization.

Initially, the user may position one or more EM patch sensors 105 on the patient. For bronchoscopy, the user places the EM patch sensors 105 to surround, or at least partially overlap, the area of interest (e.g., the patient's lungs). When the system includes three EM patch sensors 105, the user may place a first EM patch sensor on the patient's mid sternum, a second EM patch sensor on the patient's left lateral $8^{th}$ rib, and a third EM patch sensor on the patient's right lateral $8^{th}$ rib. The above-described placement of the EM patch sensors 105 is merely exemplary, and the EM patch sensors 105 may be placed in other locations that overlap the area of interest.

Figure 24:
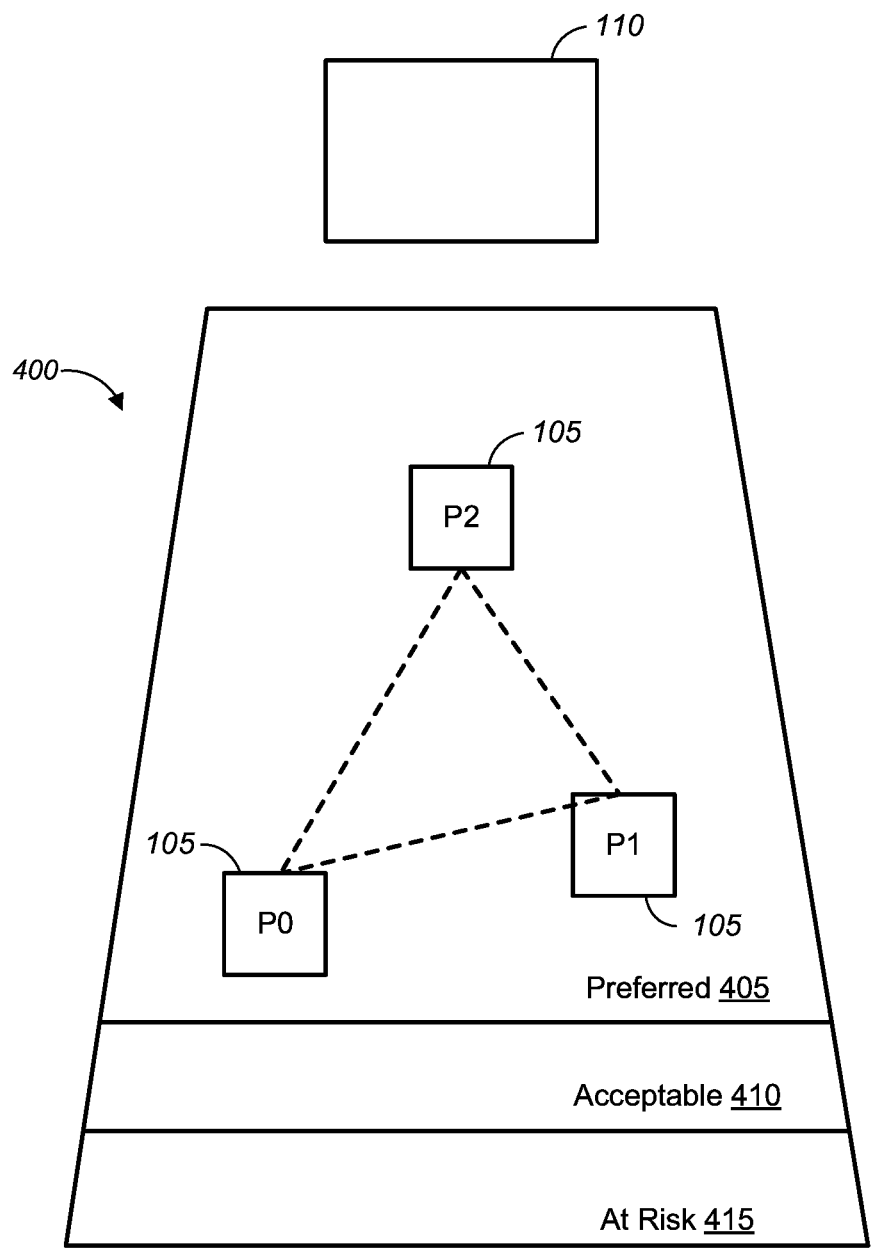
FIG. 24 provides an example in which EM patch sensors 105 are placed within a working volume of an EM field generator.

FIG. 24 provides an example in which EM patch sensors 105 are placed within a working volume of an EM field generator. After the EM patch sensors 105 have been placed, the user may position the EM field generator 110 such that the EM patch sensors 105 are located within a working volume 400 of the EM field generator 110. Although FIG. 24 illustrates a working volume 400 when viewed from above, the working volume 400 may define a three-dimensional volume in which the EM patch sensors 105 are to be placed during alignment.

The user may attach the EM field generator 110 to a holder, which may be attached to a bed rail. Using guidance provided by the EM tracking system, the user may rotate the EM field generator 110 such that all of the EM patch sensors 105 are located within the working volume 400. In order to provide feedback via a display (e.g., via the touchscreen 26), the EM tracking system may determine a position of the EM patch sensors 105 with respect to the EM field generator 110 based one or more EM patch sensor signals generated by the EM patch sensors 105. The system may encode a representation of the position of the EM patch sensors 105 with respect to the working volume of the EM field. Encoding of the representation of the position of the EM patch sensors 105 may include generating an image (or series of images to form a video) in which the relative position of the EM patch sensors 105 is displayed with respect to a representation of the working volume. The encoding may further include encoding the image (or video) using an image or video codec such that the image can be decoded and rendered by a display. The system may then provide the encoded representation of the position to a display configured to render encoded data.

The user may use the visual feedback provided by the display in rotating the EM field generator 110 such that the EM patch sensors 105 are positioned within the working volume. Once the EM patch sensors 105 are rotationally aligned with the EM field generator 110, the user may position the field generator closer to the EM patch sensors 105 such that the EM patch sensors 105 are within a predefined distance from the EM field generator 110 as defined by the visually displayed working volume. With reference to FIG. 24, the working volume may include a plurality of sub-volumes, which may define preferred 405, acceptable, 410, and at risk 415 sub-volumes. Since the strength of the EM field may decay at greater distanced from the EM field generator 110, it may be desirable to position the EM patch sensors 105 within the preferred 405 or acceptable 410 sub-volumes over the at risk 415 sub-volume.

In at least one implementation, the system may encode the representation of the position of the EM patch sensors 105 with respect to each of first and second sub-volumes of the field generator. The second sub-volume larger than and enveloping the first sub-volume, and thus, in at least one implementation, the second sub-volume may be an at-risk 415 sub-volume. The system may provide the encoded representation of the position of the EM patch sensors 105 with respect to each of the first and second sub-volumes to the display so that the user can reposition the EM patch sensors 105 within the first sub-volume by moving the EM field generator 110.

In other implementations, the first and second sub-volumes may correspond to the preferred 405 and acceptable 410 sub-volumes. In these implementations, the system may encode user instructions to the user to position the EM field generator 110 such that the EM patch sensors 105 is positioned within at least one of the first and second sub-volumes and provide the encoded user instructions to the display.

The user may repeat the rotation of the EM field generator 110 and adjusting the distance of the EM field generator 110 until all of the EM patch sensors 105 are within the working volume. Thereafter, the user may lock the position of the EM field generator 110 in preparation for the surgical procedure.

In certain implementations, it may not be possible to place all of the EM patch sensors 105 within the working volume. For example, the EM field generator 110 may not produce a large enough working volume to encompass all of the EM patch sensors 105 for patients having a large area of interest. In these implementations, the system may encode user instructions to position the field generator such that a defined number of the EM sensors are positioned within the first working volume and provide the encoded user instructions to the display. For example, when three EM patch sensors 105 are used, the system may encode instructions to the user such that at least two of the EM patch sensors 105 are positioned within the working volume.

In one implementation, the system may encode user instructions to position: (i) a first one of the EM sensors on the patient's mid sternum, (ii) a second one of the EM sensors on the patient's left lateral eighth rib, and (iii) a third one of the EM sensors on the patient's left lateral eighth rib. Thus, prior to positioning of the EM field generation 110, the system may provide the user with instructions for placement of the EM patch sensors 105. The system may provide the encoded user instructions to position the first to third EM sensors on the patient to the display.

In another implementation, the system may be configured to receive input from the user that one of the second and third EM sensors cannot be positioned with the working volume, for example, via the touchscreen 26. In response, the system may encode user instructions to reposition the one of the second and third EM sensors closer to the field generator than the one of the second and third EM sensors' current position. For example, the instruction may encode instructions to reposition the second EM patch sensor on the patient's $6^{th}$ left lateral rib. The system may provide the encoded user instructions to reposition the one of the second and third EM sensors to the display.

It is to be appreciated that some embodiments of the systems described above relating to the technical features for aligning the field generator with the patient anatomy can have a number of advantages. For example, providing feedback to the user on the placement and alignment of the field generator can simplify the setup of the system. Such a simplified setup can avoid user frustration in whether the system is properly aligned. Still further, feedback of the alignment may produce more accurate reading and, as a result, provide better input to the navigation and/or localization systems.

E. EM Tracking System and Example Flowcharts.

Figure 25:
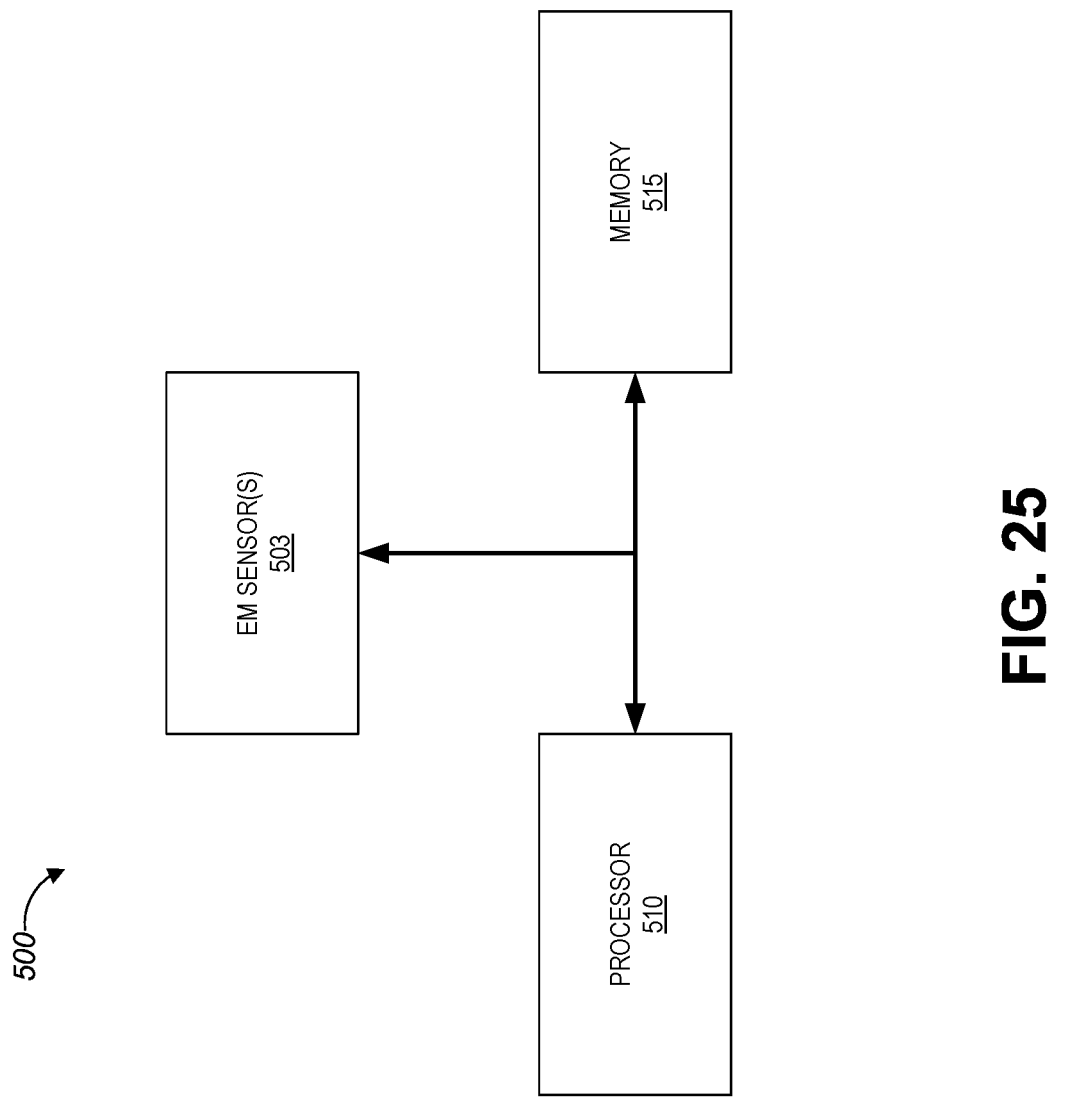
FIG. 25 depicts a block diagram illustrating an example of the EM tracking system which may perform various aspects of this disclosure.

FIG. 25 depicts a block diagram illustrating an example of the EM tracking system which may perform various aspects of this disclosure. The EM tracking system 500 may include one or more EM sensor(s) 503, a processor 510, and a memory 515. The one or more EM sensor(s) 503 may be embodied as the EM patch sensors 105 and/or the EM instrument sensor(s) 305. The EM tracking system 500 may be incorporated into one or more of the tower 30, the console 16, the EM field generator 110, and/or any other component within the environment 100. Additionally, the EM tracking system 500 may be configured to perform one or more of the methods and/or techniques described above in connection with FIGS. 20-24 or described below in connection with FIGS. 26 and 27.

Figure 26:
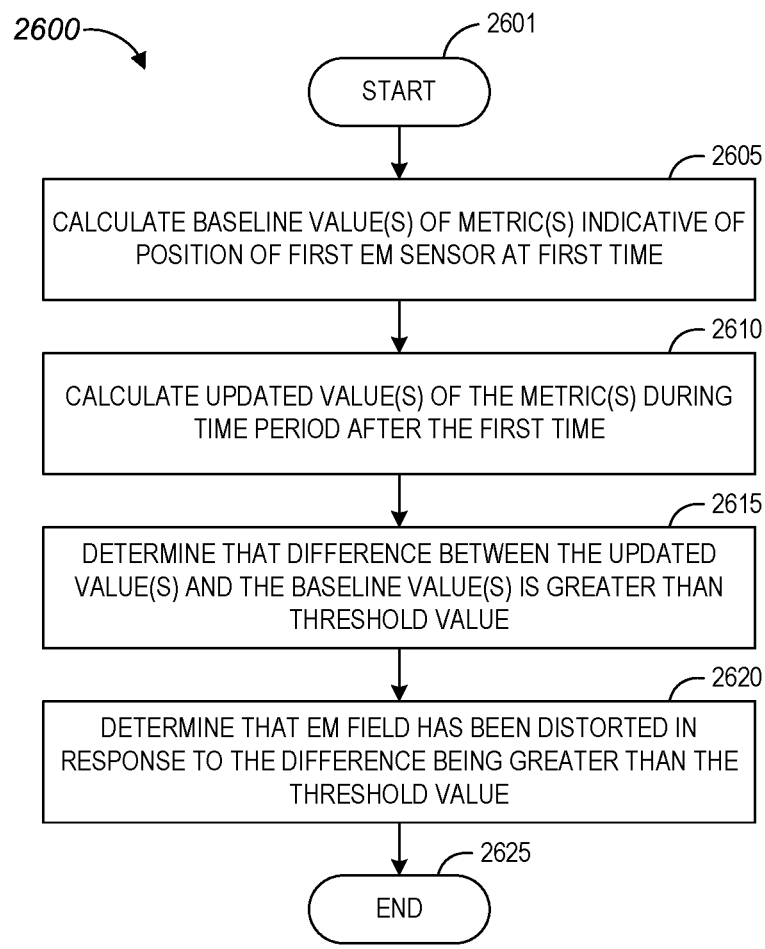
FIG. 26 is a flowchart illustrating an example method operable by an EM tracking system, or component(s) thereof, for detecting EM distortion in accordance with aspects of this disclosure.

FIG. 26 is a flowchart illustrating an example method operable by an EM tracking system 500, or component(s) thereof, for detecting EM distortion in accordance with aspects of this disclosure. For example, the steps of method 2600 illustrated in FIG. 26 may be performed by a processor 510 of the EM tracking system 500. For convenience, the method 2600 is described as performed by the processor 510 of the EM tracking system 500.

The method 2600 begins at block 2601. At block 2605, the processor 510 calculates one or more baseline values of one or more metrics indicative of a position of a first EM sensor at a first time. The calculation of the one or more baseline values may be based on EM sensor signals received from a first set of one or more EM sensor signals corresponding to the first time. Additionally, the first EM sensor may be configured to generate the first set of one or more EM sensor signals in response to detection of an EM field. At block 2610, the processor 510 calculates one or more updated values of the one or more metrics during a time period after the first time. The calculation of the one or more updated values may be based on EM sensor signals from the first set of one or more EM sensor signals corresponding to the time period after the first time.

At block 2615, the processor 510 determines that a difference between the one or more updated values and the one or more baseline values is greater than a threshold value. At block 2620, the processor 510 determines that the EM field has been distorted in response to the difference being greater than the threshold value. The method 2600 ends at block 2625.

Figure 27:
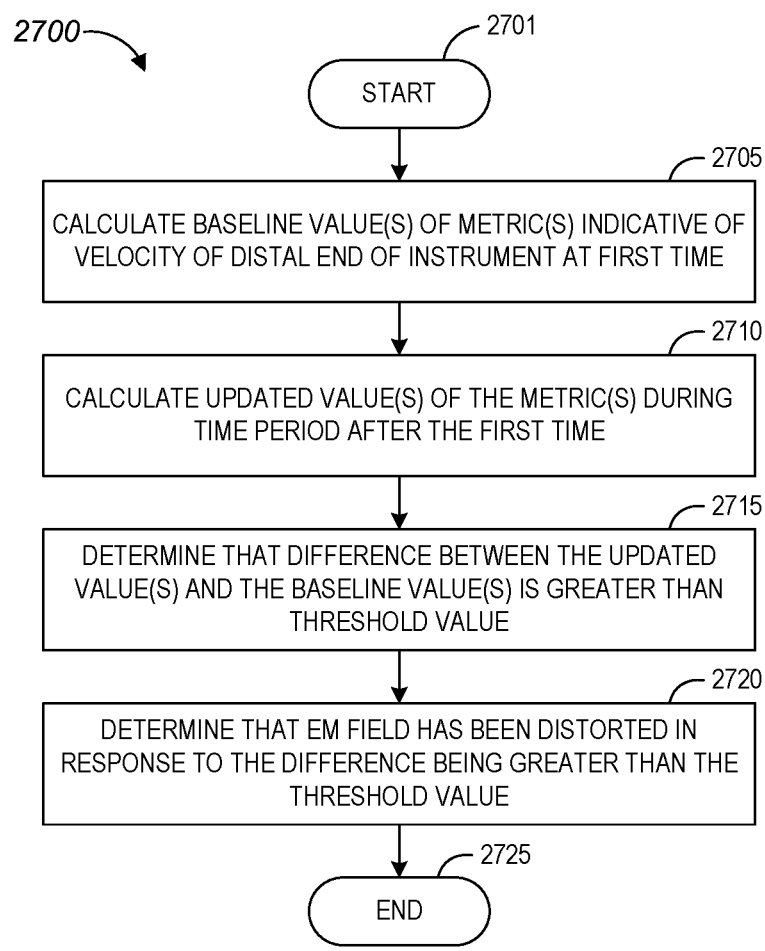
FIG. 27 is a flowchart illustrating another example method operable by an EM tracking system, or component(s) thereof, for detecting EM distortion in accordance with aspects of this disclosure.

FIG. 27 is a flowchart illustrating another example method operable by an EM tracking system 500, or component(s) thereof, for detecting EM distortion in accordance with aspects of this disclosure. For example, the steps of method 2700 illustrated in FIG. 27 may be performed by a processor 510 of the EM tracking system 500. For convenience, the method 2700 is described as performed by the processor 510 of the EM tracking system 500.

The method 2700 begins at block 2701. At block 2705, the processor 510 calculates one or more baseline values of one or more metrics indicative of a velocity of a distal end of an instrument at a first time. The calculation of the one or more baseline values may be based on EM sensor signals received from one or more EM sensor signals corresponding to the first time. The instrument may include an EM sensor located at the distal end of the instrument. The EM sensor may be configured to generate the one or more EM sensor signals in response to detection of an EM field.

At block 2710, the processor 510 calculates one or more updated values of the one or more metrics during a time period after the first time. The calculation of the one or more updated values may be based on EM sensor signals from the one or more EM sensor signals corresponding to the time period after the first time. At block 2715, the processor 510 determines that a difference between the one or more updated values and the one or more baseline values is greater than a threshold value. At block 2720, the processor 510 determines that the EM field has been distorted in response to the difference being greater than the threshold value. The method 2700 ends at block 2725.

Figure 28:
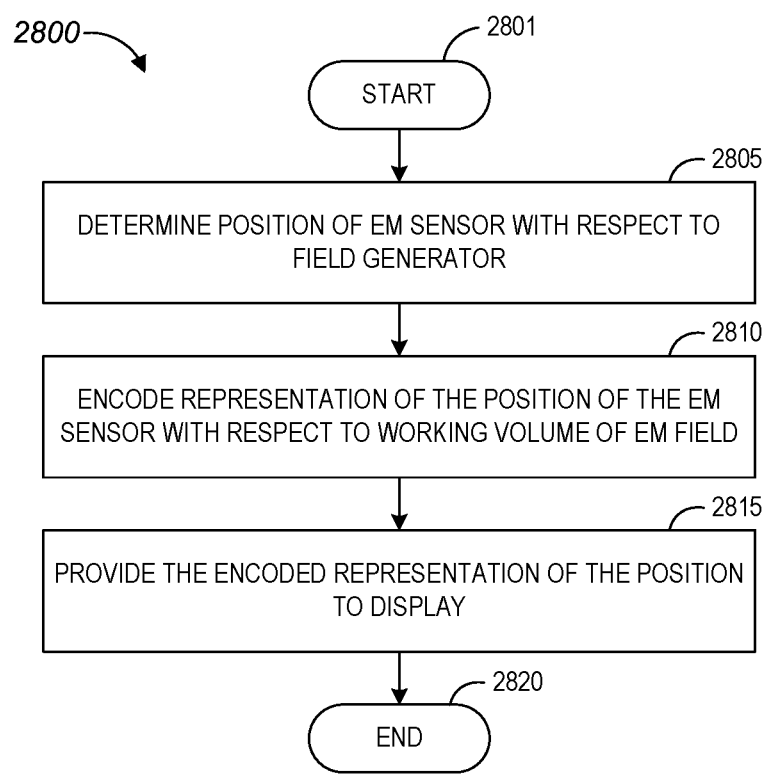
FIG. 28 is a flowchart illustrating yet another example method operable by an EM tracking system, or component(s) thereof, for facilitating the positioning of an EM sensor within an EM field generated by a field generator in accordance with aspects of this disclosure.

FIG. 28 is a flowchart illustrating yet another example method operable by an EM tracking system 500, or component(s) thereof, for facilitating the positioning of an EM sensor within an EM field generated by a field generator in accordance with aspects of this disclosure. For example, the steps of method 2800 illustrated in FIG. 28 may be performed by a processor 510 of the EM tracking system 500. For convenience, the method 2800 is described as performed by the processor 510 of the EM tracking system 500.

The method 2800 begins at block 2801. At block 2805, the processor 510 determines a position of the EM sensor with respect to the field generator based on one or more EM sensor signals. The EM sensor may be configured to generate, when positioned in a working volume of the EM field, the one or more EM sensor signals based on detection of the EM field. Additionally, the EM sensor may be configured for placement, in use, on a patient. At block 2810, the processor 510 encodes a representation of the position of the EM sensor with respect to the working volume of the EM field. At block 2815, the processor 510 provides the encoded representation of the position to a display configured to render encoded data. The method 2800 ends at block 2820.

Figure 29:
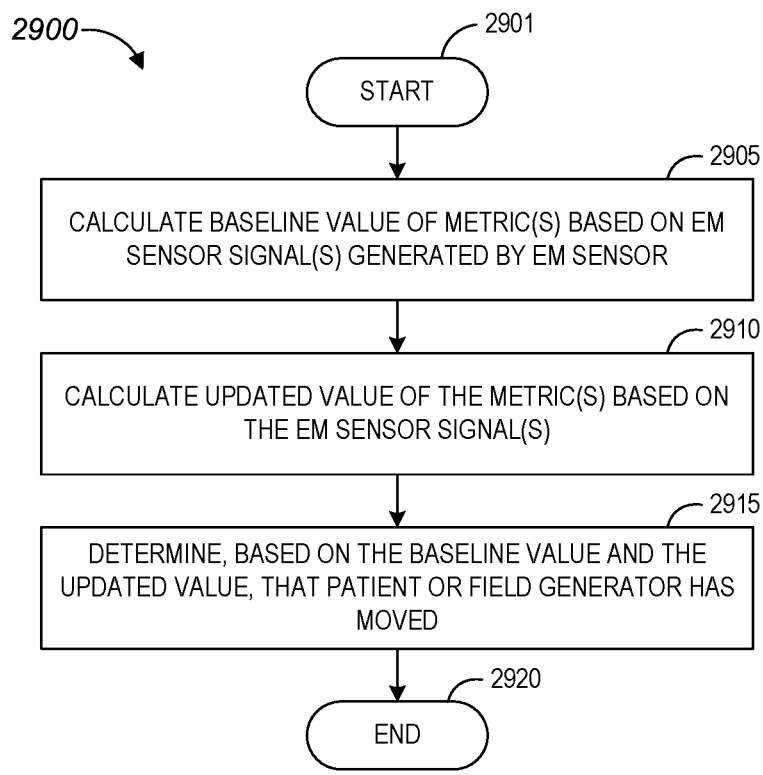
FIG. 29 is a flowchart illustrating still yet another example method operable by an EM tracking system, or component(s) thereof, for detecting movement of at least one of a patient or an EM field generator in accordance with aspects of this disclosure.

FIG. 29 is a flowchart illustrating still yet another example method operable by an EM tracking system 500, or component(s) thereof, for detecting movement of at least one of a patient or an EM field generator in accordance with aspects of this disclosure. For example, the steps of method 2900 illustrated in FIG. 29 may be performed by a processor 510 of the EM tracking system 500. For convenience, the method 2900 is described as performed by the processor 510 of the EM tracking system 500.

The method 2900 begins at block 2901. At block 2905, the processor 510 calculates a baseline value of at least one metric based on one or more EM sensor signals generated by an EM sensor. The baseline value of the at least one metric may correspond to a positioning of the EM sensor at a first time. The EM sensor may be configured to generate the one or more EM sensor signals in response to detection of an EM field. The EM sensor may be configured for placement, in use, on a patient. At block 2910, the processor 510 calculates an updated value of the at least one metric based on the one or more EM sensor signals. The updated value of the at least one metric may correspond to a positioning of the EM sensor at a second time. At block 2915, the processor 510 determines, based on the baseline value and the updated value, that at least one of the patient and the field generator has moved during a time period that includes the first time and the second time. The method 2900 ends at block 2920.

F. Introduction to EM Distortion Compensation.

In the context of navigation of a medical instrument through a luminal network, a navigation system can periodically estimate the position of the distal end of the medical instrument with respect to a model of the luminal network (e.g., based off of preoperative CT scan). The estimate can be determined using robotic command and kinematics data (e.g., which may include the insertion commanded by the user), EM location data received from one or more EM sensors positioned at the distal end of the medical instrument, and/or image data received from a camera positioned at the distal end of the medical instrument. As described above, the system includes a field generator (e.g., the EM field generator 110 of FIG. 16) which creates an oscillating EM field that induces electrical currents in the EM sensor(s) positioned at the distal end of the medical instrument. The EM sensors may be sensitive to metallic objects placed in the vicinity of the working volume of the field generator. Such metallic objects can interfere with the EM field generated by the field generator, which may lead to distortion(s) in the EM field when introduced during a medical procedure. These distortions may be incorrectly interpreted by the system as movement of the EM sensors if these distortions occur during a medical procedure, which can lead to an incorrect estimation of the location of the position of the distal end of the medical instrument. Thus, it is desirable to compensate for EM distortion in the EM field such that EM data can be used to reliably estimate the position of the medical instrument when EM distortion is present.

When performing a medical procedure such as endoscopy, the physician may desire to use fluoroscopy to aid in the procedure. To perform fluoroscopy, a metallic C-arm may be rolled into the operating room and moved around. A C-arm typically includes relatively large metallic components which, when positioned within a certain distance of the EM field generated by the EM generator, can distort the EM field. In certain systems, the EM distortions caused by the C-arm may cause EM-based navigation to get off track (e.g., the estimates of the position of the medical instrument may not be sufficiently reliable for navigation), such that the physician may have to, for example, choose between keeping navigation or using fluoroscopy. Thus, without compensation of EM distortion due to the introduction of a C-arm in the operating room, the use of navigation and fluoroscopy may be mutually exclusive.

G. Example Techniques for EM Distortion Compensation.

Aspects of this disclosure relate to systems and methods for distortion compensation which can dynamically compensate for EM distortions, such as those caused by a C-arm used for fluoroscopy or similar metallic structures. During a typical procedure, the user may drive the distal end of the medical instrument close to the target prior to brining in the C-arm for fluoroscopy. When the medical instrument is close to the target, the user is likely to not be driving the medical instrument or driving the medical instrument very slowly. In certain implementations, the system may take advantage of this typical workflow by compensating for EM distortion occurring while the medical instrument is traveling at a speed that is less than a threshold speed.

In certain implementations, the system may identify periods of time where there is no significant user movement command (e.g., user commands for movement of greater than a threshold amount of movement) as "static." During static periods, the system can determine that large movements in the position of the distal end of the medical instrument detected by the EM sensors are due to EM distortion. The system can update a distortion vector (also referred to as an offset) based on the amount of movement detected by the EM sensor when EM distortion is identified. The system can compensate the position of the distal end of the medical instrument estimated using EM sensor data using the offset, thereby enabling the other aspects of the navigation algorithms to be unaffected by the EM distortion.

Figure 30A:
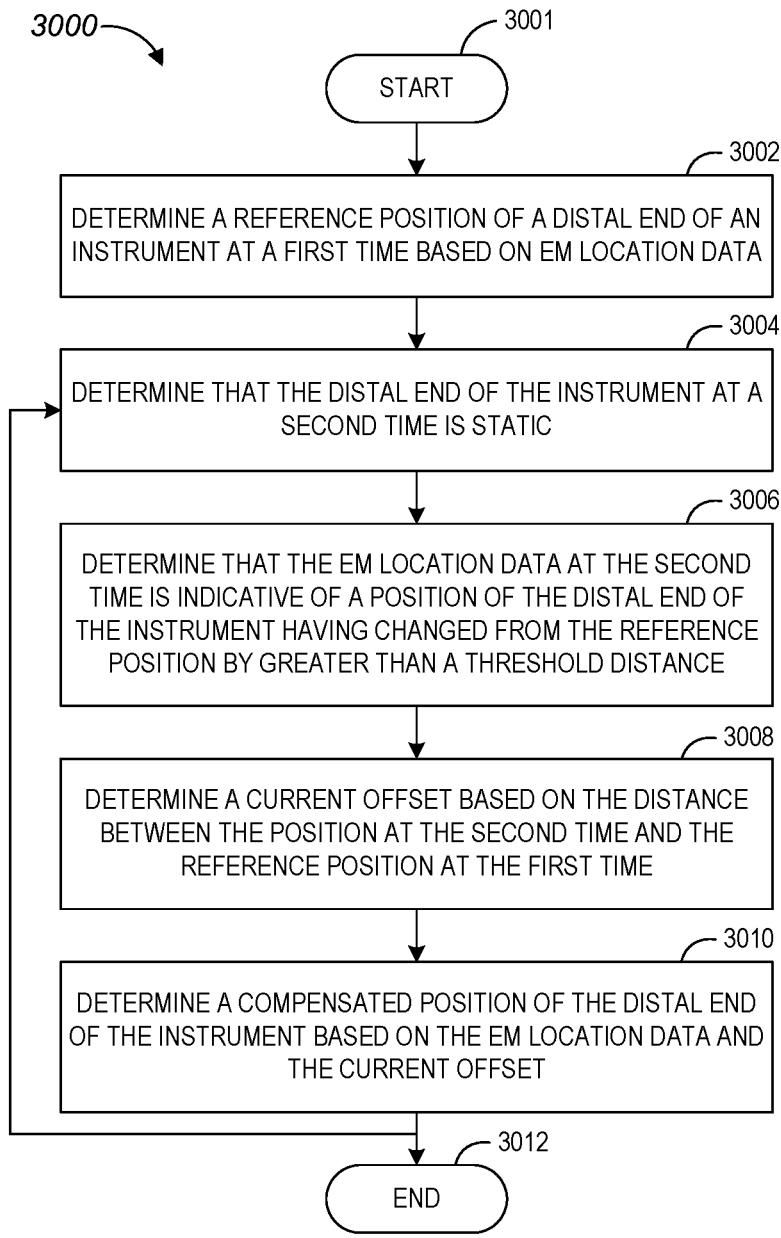
FIG. 30A is a flowchart illustrating an example method operable by an EM tracking system, or component(s) thereof, for compensating for EM distortion in accordance with aspects of this disclosure.

One exemplary implementation for compensating for EM distortion is provided in connection with FIG. 30A. FIG. 30A is a flowchart illustrating an example method 3000 operable by an EM tracking system 500, or component(s) thereof, for compensating for EM distortion in accordance with aspects of this disclosure. For example, the steps of method 3000 illustrated in FIG. 30A may be performed by a processor 510 of the EM tracking system 500. For convenience, the method 3000 is described as performed by a processor of an EM tracking system.

The method 3000 begins at block 3001. At block 3002, the processor determines a reference position of the distal end of the instrument at a first time based on the EM location data. For example, the processor can select a first EM data point and a first commanded insertion and articulation data at the first time as reference values. The first EM data point may include the reference position of the distal end of the instrument based on the EM location data.

For the remainder of the procedure, the processor may repeat the actions described in blocks 3004-3010. At block 3004, the processor may determine that the distal end of the instrument at a second time is "static." The second time may be subsequent to the first time. In some implementations, the processor can determine whether the following two conditions are met: (i) the current commanded insertion with respect to the reference commanded insertion is less than or equal to a first threshold distance (e.g., ⇐0.5 mm), and (ii) the current commanded articulation with respect to the commanded articulation is less than or equal to a threshold articulation (e.g., ⇐0.1 rad). In response to both of these conditions being met, the processor can determine that the distal end of the instrument at the second time is static.

In response to determining that the instrument is static, at block 3006, the processor determines that the EM location data at the second time is indicative of a position of the distal end of the instrument having changed from the reference position by greater than a threshold distance or amount. For example, the processor can determine that the distance between the position of the instrument at the second time and the reference position is greater than a second threshold distance (e.g., >20 mm) along any axis.

In response to determining that the distance between the position at the second time and the reference position is greater than the threshold distance, at block 3006, the processor determines an offset based on the distance between the position at the second time and the reference position at the first time. As previously described, the offset may be a vector that, when applied to the EM data, compensates for distortions in the EM data (e.g., due to introduction of an object, such as a C-arm, that can distort the EM field).

In some implementations, if the distance between the position at the second time and the reference position is not greater than the threshold distance and a current offset was previously calculated, the processor may re-calculate the current offset with respect to position of the instrument at the second time.

At block 3010, the processor may determine a compensated position of the distal end of the instrument based on the EM location data and the current offset. For example, the processor may determine the current distortion compensated EM data according to the following calculation: the current distortion compensated EM data is equal to the current EM data minus the current offset minus the reference offset. The method 3000 may repeat blocks 3002-3010 for each point in time as the instrument is maneuvered through a luminal network during the procedure.

Figure 30B:
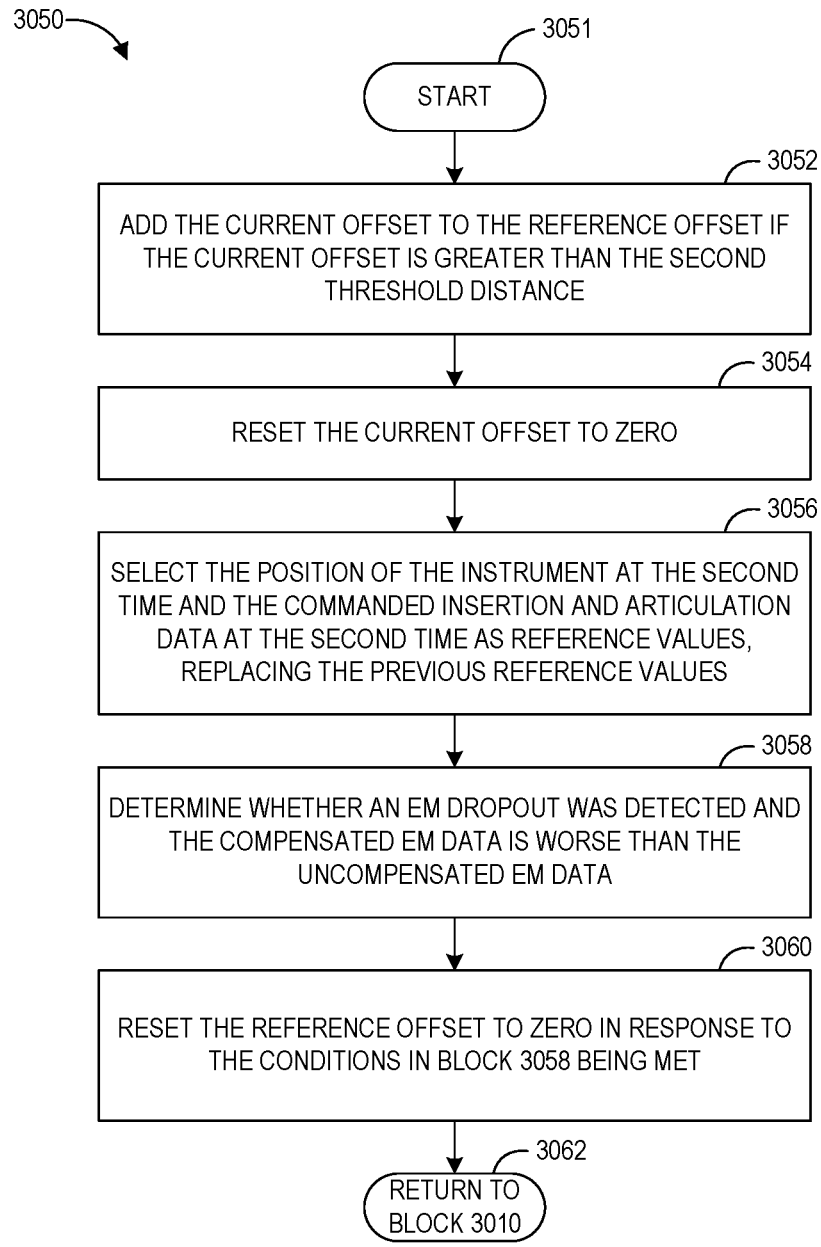
FIG. 30B is a flowchart illustrating an example method operable by an EM tracking system, or component(s) thereof, for compensating for EM distortion in accordance with aspects of this disclosure.

In response to determining that the instrument is not static, the processor may perform the method 3050 as shown in FIG. 30B. FIG. 30B is a flowchart illustrating an example method 3050 operable by an EM tracking system 500, or component(s) thereof, for compensating for EM distortion in accordance with aspects of this disclosure. At block 3052, the processor may add the current offset to the reference offset if the current offset is greater than the second threshold distance. At block 3054, the processor may reset the current offset to zero. At block 3056, the processor may select the position of the instrument at the second time and the commanded insertion and articulation data at the second time as reference values, replacing the previous reference values. At block 3058, the processor may determine whether the following two conditions are met: (i) an EM dropout was detected and (ii) the compensated EM data is worse or less reliable than the uncompensated EM data. At block 3060, the processor may reset the reference offset to zero, in response to the two conditions of block 3058 being met. The method 3050 may then return to block 3010 of the method 3000 of FIG. 30A.

Figure 31A:
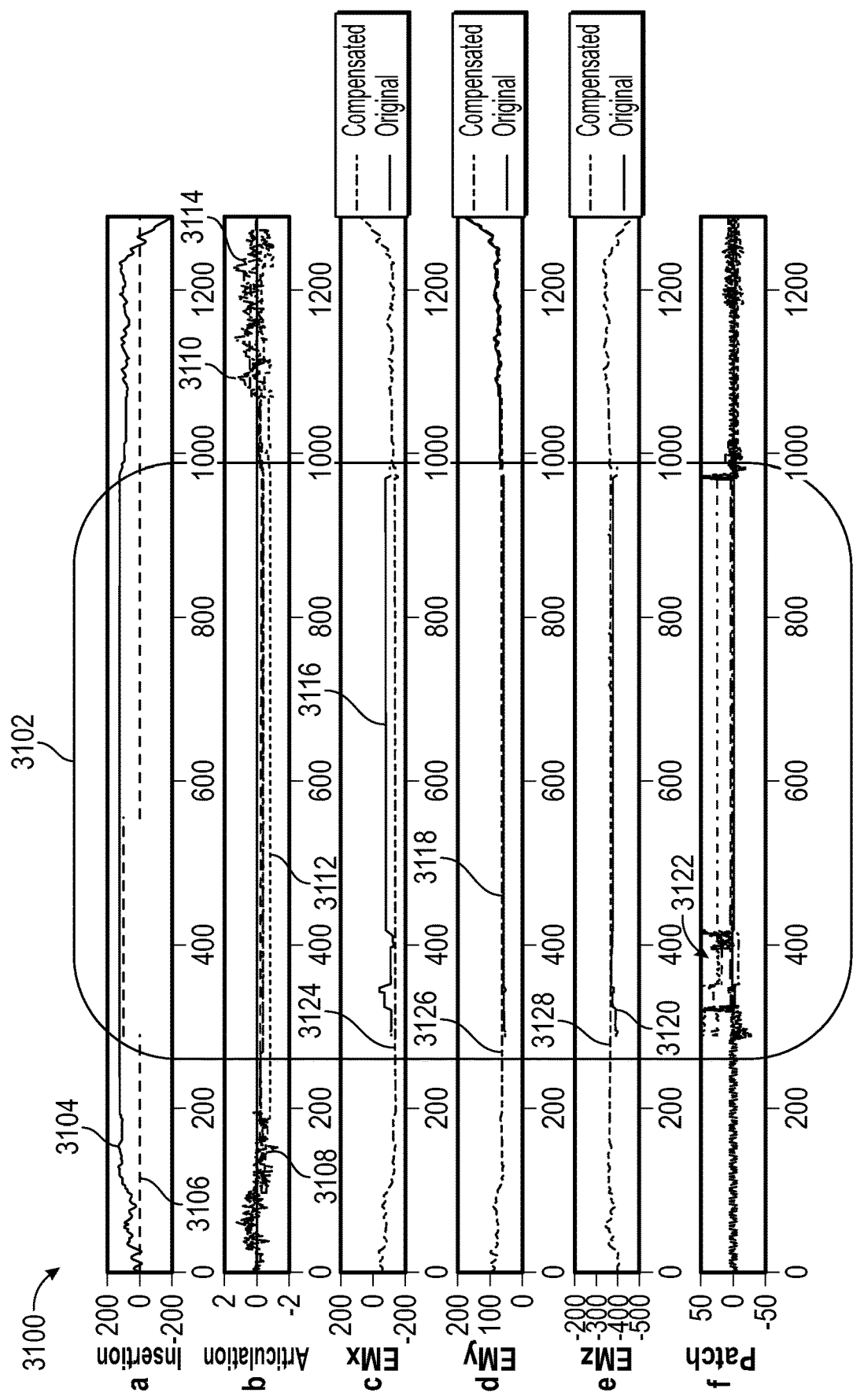
FIG. 31A is an example plot showing a number of tracked values associated with EM localization over time.
Figure 31B:
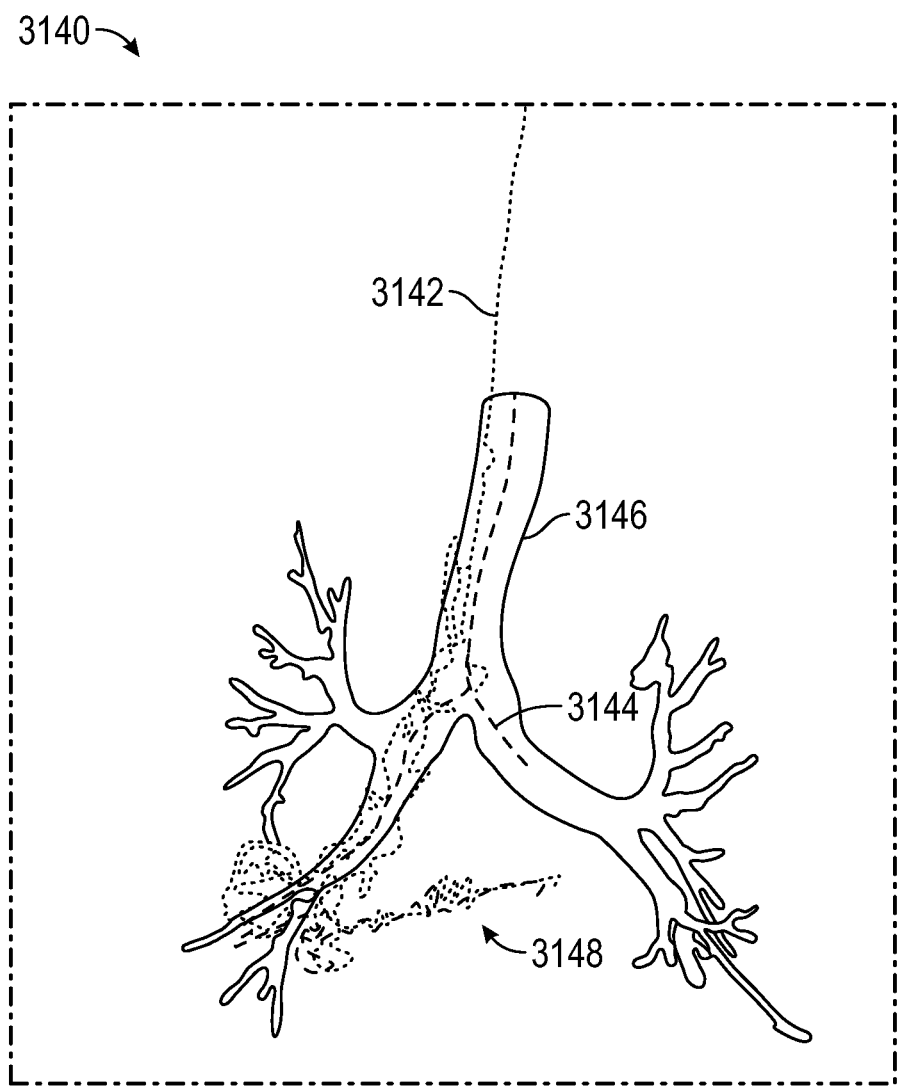
FIG. 31B provides a visualization of the position of the distal end of a medical instrument determined based on EM data without EM distortion compensation.
Figure 31C:
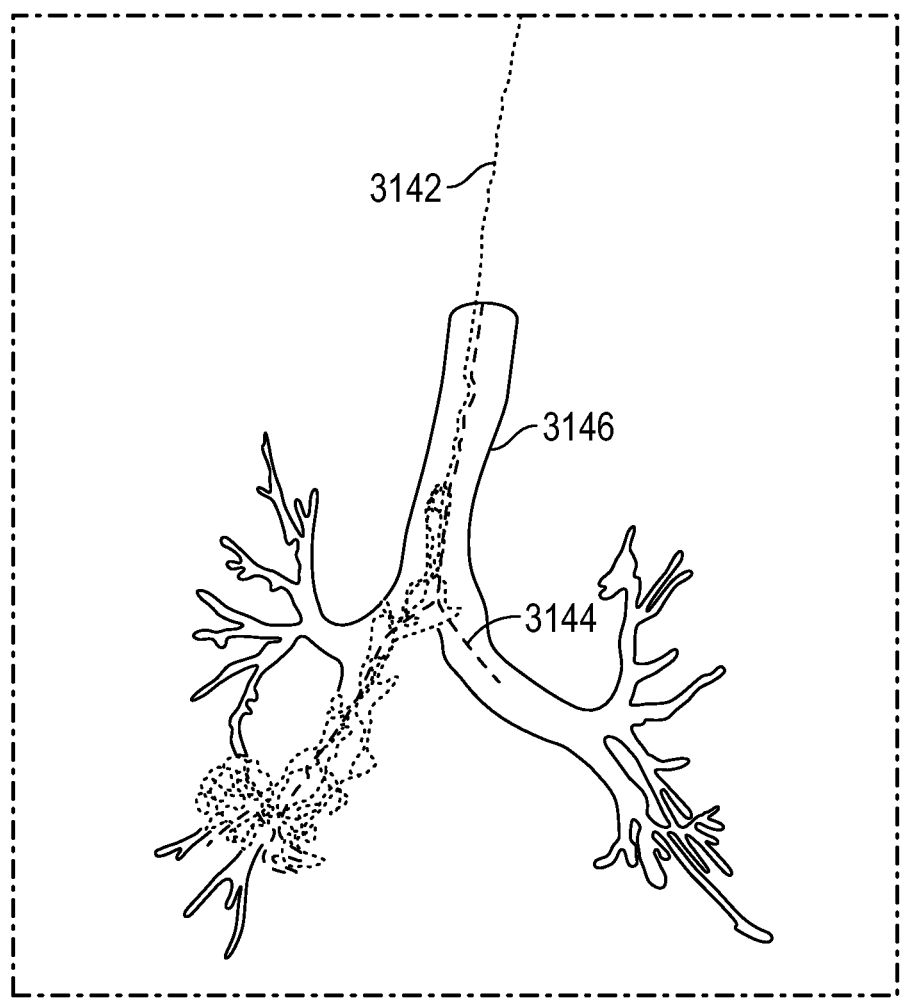
FIG. 31C provides a visualization of the position of the distal end of a medical instrument determined based on EM data with EM distortion compensation.

FIG. 31A is an example plot 3100 showing a number of tracked values associated with EM localization over time, FIG. 31B provides a visualization 3140 of the position of the distal end of a medical instrument determined based on EM data without EM distortion compensation, and FIG. 31C provides a visualization 3140 of the position of the distal end of a medical instrument determined based on EM data with EM distortion compensation.

With reference to FIG. 31A, the distortion event occurs within a box 3102. Line 3104 illustrates the commanded insertion during a navigation procedure within the portion of the plot 3100 labeled (a), while line 3106 illustrates whether the distal end of the instrument is determined to be static, for example, as determined in block 3004 of FIG. 30A (for example line 3016 has a value of 0 when non-static and a positive value when static). As shown in FIG. 31A, within the box 3102 illustrating the distortion event, the commanded insertion is substantially constant.

The second plot (b) includes lines 3108 and 3110 illustrating the commanded scope pitch and yaw articulations, respectively, and also includes lines 3112 and 3114 illustrating the commanded sheath pitch and yaw articulations, respectively. The second plot (b) shows that all the commanded articulations 3108-3114 (e.g., the scope pitch 3108 and yaw 3110 and the sheath pitch 3112 and yaw 3114) are substantially constant as well within the box 3102 illustrating the distortion event. Hence the region within the box 3102 can be determined to be static, for example, using the method 3000 of FIG. 30.

However, during the time period indicated by the box 3102, the EM distortion results in distortions in the $EM_{x,y,z}$ plots in the third, fourth and fifth plots (c, d, e) as indicated by lines 3116, 3118, and 3120, respectively. The EM distortion can also be seen from the three patch data in the plot (f) shown by the lines 3122. The distortion compensated $EM_{x,y,z}$ are shown in the lines 3124, 3216, and 3218 in plots (c, d, e).

In each of FIGS. 31B and 31C, the registered EM position 3142 and fusion position 3144 are plotted within the segmentation surface 3146. In addition, the distorted EM position 3148 is shown in FIG. 31B, which is compensated in FIG. 31C.

Figure 32A:
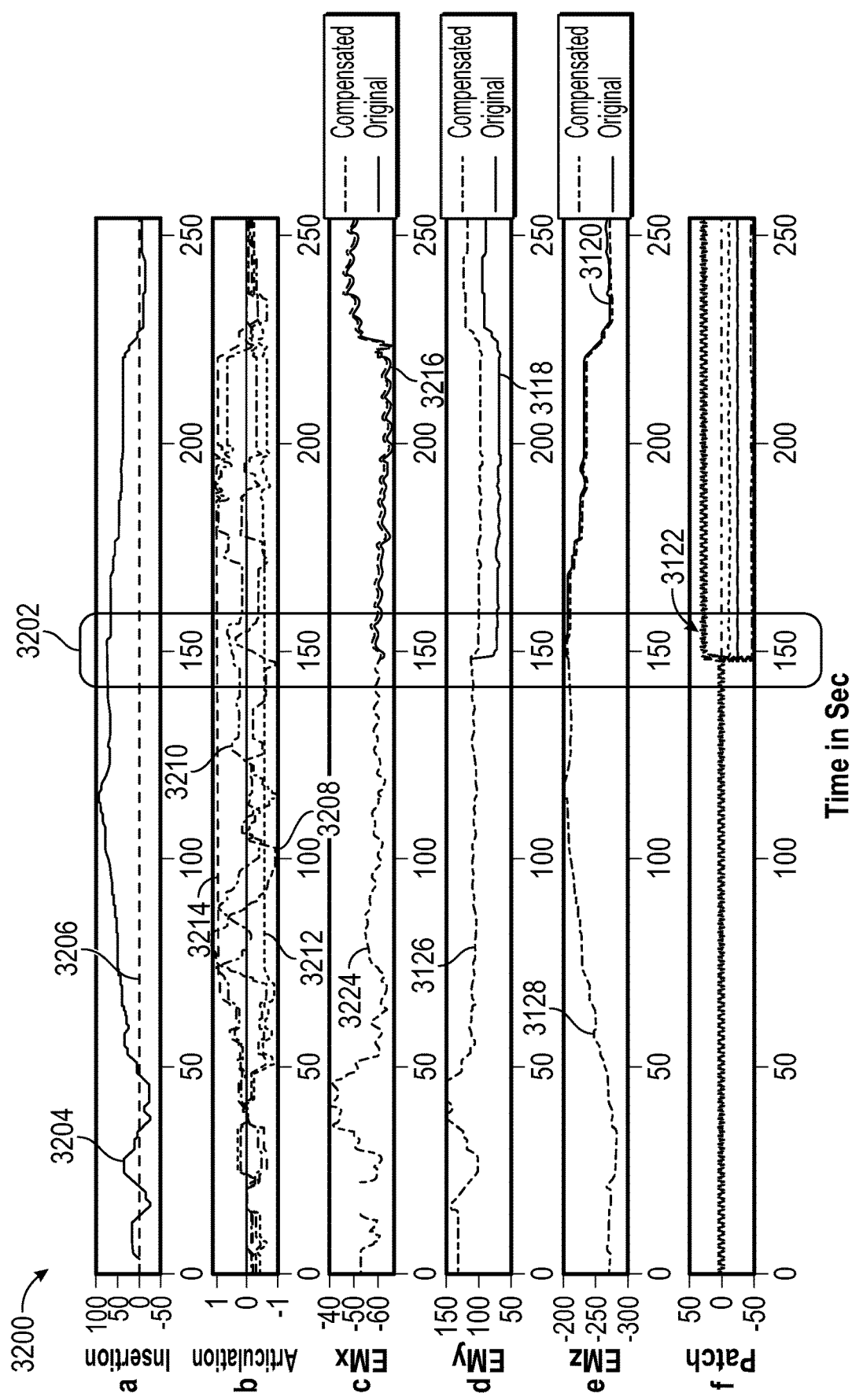
FIG. 32A illustrates another example plot showing a number of tracked values associated with EM localization over time.
Figure 32B:
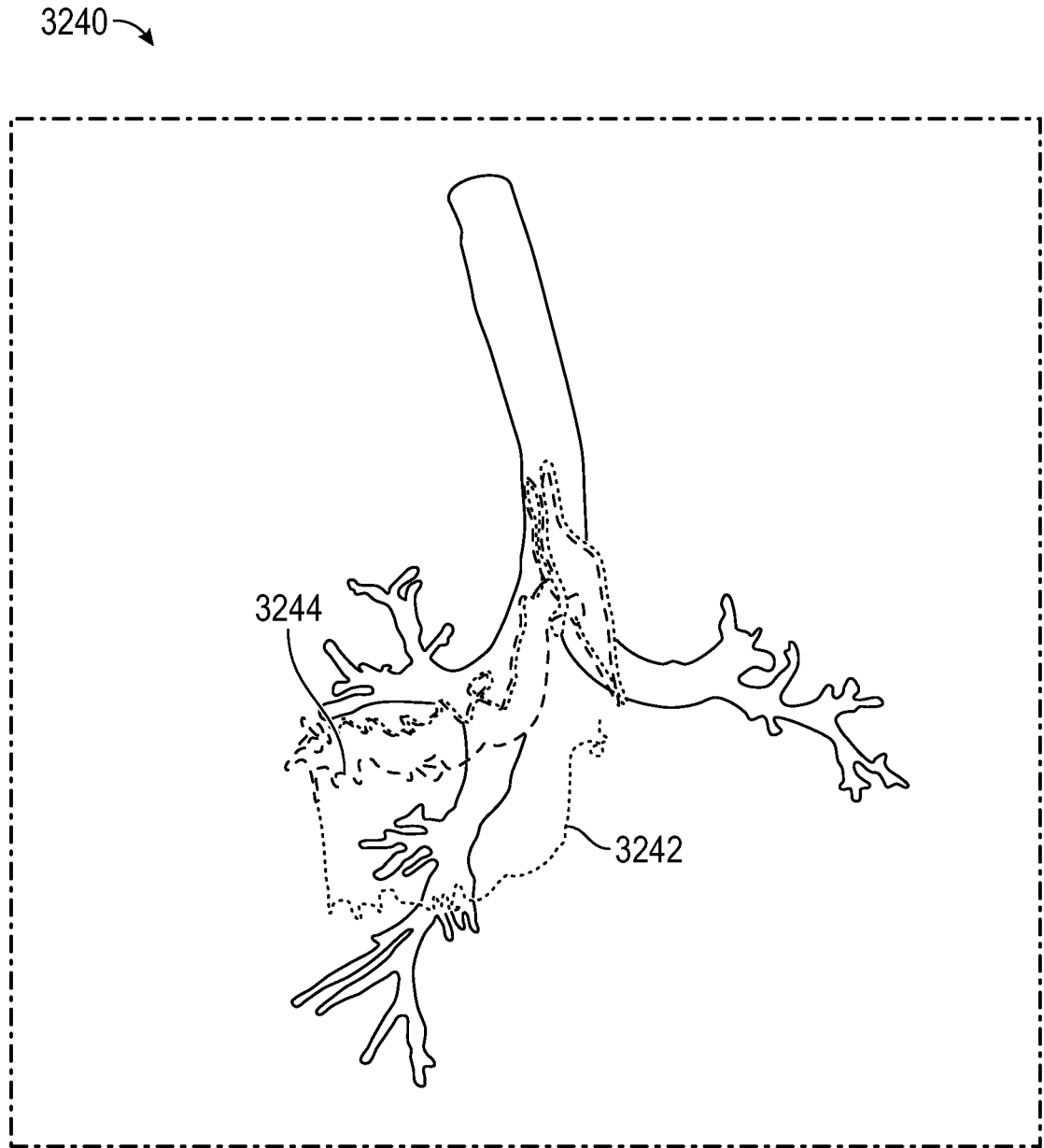
FIG. 32B provides a visualization of the position of the distal end of a medical instrument determined based on EM data without EM distortion compensation and with EM distortion compensation.

FIG. 32A illustrates another example including a number of tracked values associated with EM localization over time, and FIG. 32B provides a visualization 3240 of the position of the distal end of a medical instrument determined based on EM data without EM distortion compensation and with EM distortion compensation. Specifically, FIG. 32A provides another example showing distortion compensation while the user is driving slowly, in order to compensate for the distortion event represented by box 3202. Each of the lines 3204-3230 illustrated in FIG. 32A illustrate substantially the same tracked values as those illustrated by the lines 3104-3130 of FIG. 31A. In FIG. 32B, the line 3242 illustrates the registered EM trace including the distortion due to the distortion event 3202 which is compensated for in the line 3244.

In certain implementations, additional data sources in addition to and/or in lieu of EM distortion compensated EM data can be used by the fusion algorithm to aid in localizing the position of the distal end of the medical instrument. For example, shape sensing technology can be used to determine the position of the distal end of the instrument. Shape sensing technology is not sensitive to metallic objects, and thus, can be used to mitigate the effects of EM distortion. However, shape sensing may have a number of challenges, such as propagation of errors, cost of goods (COGs), etc.

One advantage of certain aspects of the EM distortion compensation technique disclosed herein include allowing the medical instrument to be used while moving the C-arm, without introducing the challenges associated with shape sensing technology.

EM distortion compensation may not be as accurate when the user is driving fast (e.g., at a speed greater than a threshold speed) and is inducing distortion at the same time (e.g., via C-arm movement). In some implementations, the system can use a predictive modeling approach, such as, for example, a Kalman filter, to estimate where the distal end of the instrument is expected to have moved given the user commands. The predictive modeling approach can identify when the instrument is deviating from the predicted position by more than a threshold distance (e.g., by comparing the difference between the predicted position and the position determined using EM data to the threshold distance). During periods of distortion (e.g., deviation from the predicted position by greater than the threshold distance), the system can use the model prediction as an input for the fusion algorithm and update a distortion offset used to compensate the EM data.

One exemplary technique for EM distortion compensation may involve analyzing numerous cases of EM distortion and comparing these cases to a standard driving of an instrument. Distortion patterns may be identifiable by constructing a custom filter, or based on a machine learning approach. Such techniques may be limited in the ability to distinguish between distortion events and "flicks," where the scope suddenly loses some anatomical support and straightens out substantially instantaneously. Aspects of this disclosure described herein can handle these flicks because flicks typically happen during dynamic driving (e.g., the non-static case).

In some implementations, the system may enable the user to actively "freeze" the navigation via a manual command before a C-arm or other metallic object is moved. For example, the system may include some UI context menu or button on the pendant controller to allow the user to freeze navigation. Such manual freezing implementations may rely on the user to remember to freeze navigation before performing any possible distortion actions such as moving the C-arm. The user can resume navigation upon inputting motion commands for driving the instrument. After each motion command, however, the user would have to remember to reactivate the freezing of navigation before performing further potentially EM distortion causing actions. In some implementations, the system may combine a manual freeze option along with one or more of the "auto freeze" approaches described herein (e.g., the EM distortion algorithms described above).

In some implementations, camera feedback (e.g., from a camera at the distal end of the instrument) can be used to detect the absence of relative motion in the body. However, the accuracy of using camera feedback to detect motion may be limited by the visibility of the airways in the view captured by the camera. The visibility may vary depending on the target and the patient.

Implementing Systems and Terminology

Implementations disclosed herein provide systems, methods and apparatus for the detection of EM distortion.

It should be noted that the terms "couple," "coupling," "coupled" or other variations of the word couple as used herein may indicate either an indirect connection or a direct connection. For example, if a first component is "coupled" to a second component, the first component may be either indirectly connected to the second component via another component or directly connected to the second component.

The robotic motion actuation functions described herein may be stored as one or more instructions on a processor-readable or computer-readable medium. The term "computer-readable medium" refers to any available medium that can be accessed by a computer or processor. By way of example, and not limitation, such a medium may comprise random access memory (RAM), read-only memory (ROM), electrically erasable programmable read-only memory (EEPROM), flash memory, compact disc read-only memory (CD-ROM) or other optical disk storage, magnetic disk storage or other magnetic storage devices, or any other medium that can be used to store desired program code in the form of instructions or data structures and that can be accessed by a computer. It should be noted that a computer-readable medium may be tangible and non-transitory. As used herein, the term "code" may refer to software, instructions, code or data that is/are executable by a computing device or processor.

The methods disclosed herein comprise one or more steps or actions for achieving the described method. The method steps and/or actions may be interchanged with one another without departing from the scope of the claims. In other words, unless a specific order of steps or actions is required for proper operation of the method that is being described, the order and/or use of specific steps and/or actions may be modified without departing from the scope of the claims.

As used herein, the term "plurality" denotes two or more. For example, a plurality of components indicates two or more components. The term "determining" encompasses a wide variety of actions and, therefore, "determining" can include calculating, computing, processing, deriving, investigating, looking up (e.g., looking up in a table, a database or another data structure), ascertaining and the like. Also, "determining" can include receiving (e.g., receiving information), accessing (e.g., accessing data in a memory) and the like. Also, "determining" can include resolving, selecting, choosing, establishing and the like.

The phrase "based on" does not mean "based only on," unless expressly specified otherwise. In other words, the phrase "based on" describes both "based only on" and "based at least on."

The previous description of the disclosed implementations is provided to enable any person skilled in the art to make or use the present invention. Various modifications to these implementations will be readily apparent to those skilled in the art, and the generic principles defined herein may be applied to other implementations without departing from the scope of the invention. For example, it will be appreciated that one of ordinary skill in the art will be able to employ a number corresponding alternative and equivalent structural details, such as equivalent ways of fastening, mounting, coupling, or engaging tool components, equivalent mechanisms for producing particular actuation motions, and equivalent mechanisms for delivering electrical energy. Thus, the present invention is not intended to be limited to the implementations shown herein but is to be accorded the widest scope consistent with the principles and novel features disclosed herein.

What is claimed is:

1. A system, comprising:
    an instrument comprising a set of one or more electromagnetic (EM) sensors, the EM sensors configured to generate EM location data indicative of a position of a distal end of the instrument;
    one or more processors; and
    at least one computer-readable memory in communication with the one or more processors and having stored thereon computer-executable instructions to cause the one or more processors to:
        determine a reference position of the distal end of the instrument at a first time based on the EM location data,
        determine that the distal end of the instrument at a second time is static, the second time being subsequent to the first time,
        determine that the EM location data corresponding to the second time is indicative of the position of the distal end of the instrument at the second time having changed from the reference position by greater than a threshold distance,
        determine a current offset based on the distance between the position of the distal end of the instrument indicated by the EM location data corresponding to the second time and the reference position at the first time, and
        determine a compensated position of the distal end of the instrument based on the EM location data and the current offset.

2. The system of claim 1, wherein the current offset comprises a distortion vector proportional to an amount of EM distortion caused by movement of a source of the EM distortion or a change in electrical current flow within the source of the EM distortion.

3. The system of claim 1, wherein the computer-executable instructions further cause the one or more processors to:
    determine that the distal end of the instrument at a third time is non-static, the third time being subsequent to the second time,
    determine that the current offset is greater than the threshold distance,
    in response to determining that the distal end of the instrument at the third time is non-static and that the current offset is greater than the threshold distance, generate a reference offset based on the current offset, and
    determine a compensated position of the distal end of the instrument at the third time based on the EM location data and the reference offset.

4. The system of claim 3, wherein the computer-executable instructions further cause the one or more processors to:
    determine that the compensated position at the third time is less accurate than an uncompensated position determined based on the EM location data without compensation, and
    in response to determining that the compensated position at the third time is less accurate than the uncompensated position, reset the reference offset.

5. The system of claim 1, wherein the computer-executable instructions further cause the one or more processors to:
    estimate the position of the distal end of the instrument at the second time using predictive modeling, and
    determine that the position of the distal end of the instrument at the second time deviates from the estimated position of the distal end of the instrument by more than a threshold distance,
    wherein the determining of the current offset is further based on the estimated position of the distal end of the instrument in response to determining that the position of the distal end of the instrument at the second time deviates from the estimated position of the distal end of the instrument by more than a threshold distance.

6. The system of claim 1, wherein the computer-executable instructions further cause the one or more processors to:
    filter distortion patterns from the EM data using a custom filter or machine learning.

7. The system of claim 6, wherein the distortion patterns are identified based on an analysis of a plurality of EM distortion cases and a plurality of standard instrument driving cases.

8. The system of claim 1, wherein the computer-executable instructions further cause the one or more processors to:
    receive a user instruction to freeze navigation prior to movement of a source of EM distortion,
    freeze movement of the determined location of the distal end of the instrument based on the EM location data in response to receiving the user instruction to freeze navigation, and
    receive a user instruction to unfreeze navigation.

9. The system of claim 8, wherein determining the current offset is further based on a difference in the determined position of the distal end of the instrument prior to receiving the user instruction to freeze navigation and after receiving the user instruction to unfreeze navigation.

10. A method of compensating for electromagnetic (EM) distortion, comprising:
    determining a reference position of a distal end of an instrument at a first time based on EM location data, the instrument comprising one or more EM sensors configured to generate the EM location data indicative of a position of the distal end of the instrument;
    determining that the distal end of the instrument at a second time is static, the second time being subsequent to the first time;
    determining that the EM location data corresponding to the second time is indicative of the position of the distal end of the instrument at the second time having changed from the reference position by greater than a threshold distance;
    determining a current offset based on the distance between the position of the distal end of the instrument indicated by the EM location data corresponding to the second time and the reference position at the first time; and
    determining a compensated position of the distal end of the instrument based on the EM location data and the current offset.

11. The method of claim 10, wherein the current offset comprises a distortion vector proportional to an amount of EM distortion caused by movement of a source of the EM distortion.

12. The method of claim 10, further comprising:
    determining that the distal end of the instrument at a third time is non-static, the third time being subsequent to the second time;
    determining that the current offset is greater than the threshold distance;
    in response to determining that the distal end of the instrument at the third time is non-static and that the current offset is greater than the threshold distance, generating a reference offset based on the current offset; and
    determining a compensated position of the distal end of the instrument at the third time based on the EM location data and the reference offset.

13. The method of claim 12, further comprising:
    determining that the compensated position at the third time is less accurate than an uncompensated position determined based on the EM location data without compensation; and
    in response to determining that the compensated position at the third time is less accurate than the uncompensated position, resetting the reference offset.

14. The method of claim 10, further comprising:
    estimating the position of the distal end of the instrument at the second time using predictive modeling; and
    determining that the position of the distal end of the instrument at the second time deviates from the estimated position of the distal end of the instrument by more than a threshold distance,
    wherein the determining of the current offset is further based on the estimated position of the distal end of the instrument in response to determining that the position of the distal end of the instrument at the second time deviates from the estimated position of the distal end of the instrument by more than a threshold distance.

15. The method of claim 10, further comprising:
    filtering distortion patterns from the EM data using a custom filter or machine learning.

16. The method of claim 15, wherein the distortion patterns are identified based on an analysis of a plurality of EM distortion cases and a plurality of standard instrument driving cases.

17. The method of claim 10, further comprising:
    receiving a user instruction to freeze navigation prior to movement of a source of EM distortion;
    freezing movement of the determined location of the distal end of the instrument based on the EM location data in response to receiving the user instruction to freeze navigation; and
    receiving a user instruction to unfreeze navigation.

18. The method of claim 17, wherein determining the current offset is further based on a difference in the determined position of the distal end of the instrument prior to receiving the user instruction to freeze navigation and after receiving the user instruction to unfreeze navigation.

19. A non-transitory computer readable storage medium having stored thereon instructions that, when executed, cause at least one computing device to:
    determine a reference position of a distal end of an instrument at a first time based on EM location data, the instrument comprising one or more EM sensors configured to generate the EM location data indicative of a position of the distal end of the instrument;
    determine that the distal end of the instrument at a second time is static, the second time being subsequent to the first time;
    determine that the EM location data corresponding to the second time is indicative of the position of the distal end of the instrument at the second time having changed from the reference position by greater than a threshold distance;
    determine a current offset based on the distance between the position of the distal end of the instrument indicated by the EM location data corresponding to the second time and the reference position at the first time; and
    determine a compensated position of the distal end of the instrument based on the EM location data and the current offset.

20. The non-transitory computer readable storage medium of claim 19, wherein the current offset comprises a distortion vector proportional to an amount of EM distortion caused by movement of a source of the EM distortion.

21. The non-transitory computer readable storage medium of claim 19, further having stored thereon instructions that, when executed, cause the at least one computing device to:
    determine that the distal end of the instrument at a third time is non-static, the third time being subsequent to the second time;
    determine that the current offset is greater than the threshold distance;
    in response to determining that the distal end of the instrument at the third time is non-static and that the current offset is greater than the threshold distance, generate a reference offset based on the current offset; and
    determine a compensated position of the distal end of the instrument at the third time based on the EM location data and the reference offset.

22. The non-transitory computer readable storage medium of claim 21, further having stored thereon instructions that, when executed, cause the at least one computing device to:
determine that the compensated position at the third time is less accurate than an uncompensated position determined based on the EM location data without compensation; and
in response to determining that the compensated position at the third time is less accurate than the uncompensated position, reset the reference offset.

23. The non-transitory computer readable storage medium of claim 19, further having stored thereon instructions that, when executed, cause the at least one computing device to:
estimate the position of the distal end of the instrument at the second time using predictive modeling; and
determine that the position of the distal end of the instrument at the second time deviates from the estimated position of the distal end of the instrument by more than a threshold distance,
wherein the determining of the current offset is further based on the estimated position of the distal end of the instrument in response to determining that the position of the distal end of the instrument at the second time deviates from the estimated position of the distal end of the instrument by more than a threshold distance.

24. The non-transitory computer readable storage medium of claim 19, further having stored thereon instructions that, when executed, cause the at least one computing device to:
filter distortion patterns from the EM data using a custom filter or machine learning.

25. The non-transitory computer readable storage medium of claim 24, wherein the distortion patterns are identified based on an analysis of a plurality of EM distortion cases and a plurality of standard instrument driving cases.

26. The non-transitory computer readable storage medium of claim 19, further having stored thereon instructions that, when executed, cause the at least one computing device to:
receive a user instruction to freeze navigation prior to movement of a source of EM distortion;
freeze movement of the determined location of the distal end of the instrument based on the EM location data in response to receiving the user instruction to freeze navigation; and
receive a user instruction to unfreeze navigation.

27. A system, comprising:
an instrument comprising a set of one or more electromagnetic (EM) sensors, the EM sensors configured to generate EM location data indicative of a position of a distal end of the instrument;
one or more processors; and
at least one computer-readable memory in communication with the one or more processors and having stored thereon computer-executable instructions to cause the one or more processors to:
determine a reference position of the distal end of the instrument at a first time based on the EM location data,
determine that the distal end of the instrument at a second time is static, the second time being subsequent to the first time,
determine that the EM location data corresponding to the second time is indicative of the position of the distal end of the instrument at the second time having changed from the reference position by greater than a threshold distance, and
determine a compensated position of the distal end of the instrument based on the EM location data and the determination that the position of the distal end of the instrument at the second time has changed from the reference position by greater than a threshold distance.

28. The system of claim 27, wherein the computer-executable instructions further cause the one or more processors to:
determine a distortion vector proportional to an amount of EM distortion caused by movement of a source of the EM distortion,
wherein the determination of the compensated position is further based on the distortion vector.

29. The system of claim 28, wherein the computer-executable instructions further cause the one or more processors to:
determine that the distal end of the instrument at a third time is non-static, the third time being subsequent to the second time,
determine that the distortion vector is greater than the threshold distance,
in response to determining that the distal end of the instrument at the third time is non-static and that the distortion vector is greater than the threshold distance, generate a reference offset based on the distortion vector, and
determine a compensated position of the distal end of the instrument at the third time based on the EM location data and the reference offset.

30. The system of claim 29, wherein the computer-executable instructions further cause the one or more processors to:
determine that the compensated position at the third time is less accurate than an uncompensated position determined based on the EM location data without compensation, and
in response to determining that the compensated position at the third time is less accurate than the uncompensated position, reset the reference offset.

* * * * *